United States Patent
Yamamoto

(10) Patent No.: US 10,588,598 B2
(45) Date of Patent: Mar. 17, 2020

(54) ULTRASONIC INSPECTION APPARATUS

(71) Applicant: FUJIFILM CORPORATION, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 571 days.

(21) Appl. No.: 14/594,889

(22) Filed: Jan. 12, 2015

(65) Prior Publication Data

US 2015/0141831 A1 May 21, 2015

Related U.S. Application Data

(63) Continuation of application No. PCT/JP2013/069010, filed on Jul. 11, 2013.

(30) Foreign Application Priority Data

Jul. 13, 2012 (JP) ................................ 2012-158009
Jul. 10, 2013 (JP) ................................ 2013-144809

(51) Int. Cl.
*A61B 8/14* (2006.01)
*A61B 8/00* (2006.01)
(Continued)

(52) U.S. Cl.
CPC .............. *A61B 8/14* (2013.01); *A61B 8/4488* (2013.01); *A61B 8/5207* (2013.01); *A61B 8/54* (2013.01);
(Continued)

(58) Field of Classification Search
None
See application file for complete search history.

(56) References Cited

U.S. PATENT DOCUMENTS 4,817,614 A * 4/1989 Hassler .................. G01H 17/00
600/441
2006/0004287 A1 * 1/2006 Rigby ................. G01S 7/52025
600/437
(Continued)

FOREIGN PATENT DOCUMENTS

JP 2003-180688 A 7/2003
JP 2009-240700 A 10/2009
(Continued)

OTHER PUBLICATIONS

Powers et al., "Medical Ultrasound Systems", Interface Focus (2011) 1, 477-489.*
(Continued)

*Primary Examiner* — Katherine L Fernandez
*Assistant Examiner* — Yi-Shan Yang
(74) *Attorney, Agent, or Firm* — Birch, Stewart, Kolasch & Birch, LLP

(57) ABSTRACT

An ultrasonic inspection apparatus includes: a probe; a transmission unit configured to cause the probe to transmit a ultrasonic beam; a reception unit configured to receive analog element signals output by the probe; an A/D conversion unit configured to perform A/D conversion on the analog element signal to obtain first element data; and a data processing unit configured to generate second element data from a plurality of the pieces of first element data, wherein the data processing unit changes conditions of acquisition of two or more of the pieces of first element data for generating the second element data depending on a depth of a position in which the second element data is obtained.

26 Claims, 24 Drawing Sheets

(51) Int. Cl.
*G01S 15/89* (2006.01)
*G01S 7/52* (2006.01)
*G10K 11/34* (2006.01)
*A61B 8/08* (2006.01)

(52) U.S. Cl.
CPC ...... *G01S 7/52046* (2013.01); *G01S 15/8915* (2013.01); *G10K 11/346* (2013.01); *A61B 8/4483* (2013.01); *A61B 8/463* (2013.01); *A61B 8/469* (2013.01)

(56) References Cited

U.S. PATENT DOCUMENTS

| | | | |
|---|---|---|---|
| 2009/0069692 A1* | 3/2009 | Cooley | G01S 7/52028 600/459 |
| 2009/0069693 A1* | 3/2009 | Burcher | G01S 7/52028 600/459 |
| 2009/0326377 A1 | 12/2009 | Hirama | |
| 2010/0312114 A1 | 12/2010 | Karasawa | |
| 2012/0281902 A1 | 11/2012 | Oikawa et al. | |
| 2012/0323121 A1* | 12/2012 | Miller | A61B 8/4488 600/443 |
| 2013/0338944 A1* | 12/2013 | Nagae | A61B 8/14 702/56 |
| 2014/0140600 A1* | 5/2014 | Daigle | G06T 5/001 382/131 |
| 2014/0343422 A1* | 11/2014 | Waki | A61B 8/4494 600/438 |

FOREIGN PATENT DOCUMENTS

| | | |
|---|---|---|
| JP | 2011-11045 A | 1/2011 |
| JP | 2011-172611 A | 9/2011 |
| WO | WO 2011105593 A1 * | 9/2011 ......... G01S 7/52034 |

OTHER PUBLICATIONS

International Search Report issued in PCT/JP2013/069010, dated Aug. 6, 2013.

International Preliminary Report on Patentability and English translation of the Written Opinion of the International Searching Authority (Forms PCT/IB/338, PCT/IB/373 and PCT/ISA/237), dated Jan. 22, 2015, for International Application No. PCT/JP2013/069010.

Japanese Office Action, dated Oct. 20, 2015, for corresponding Japanese Application No. 2013-144809, with a partial English translation.

* cited by examiner

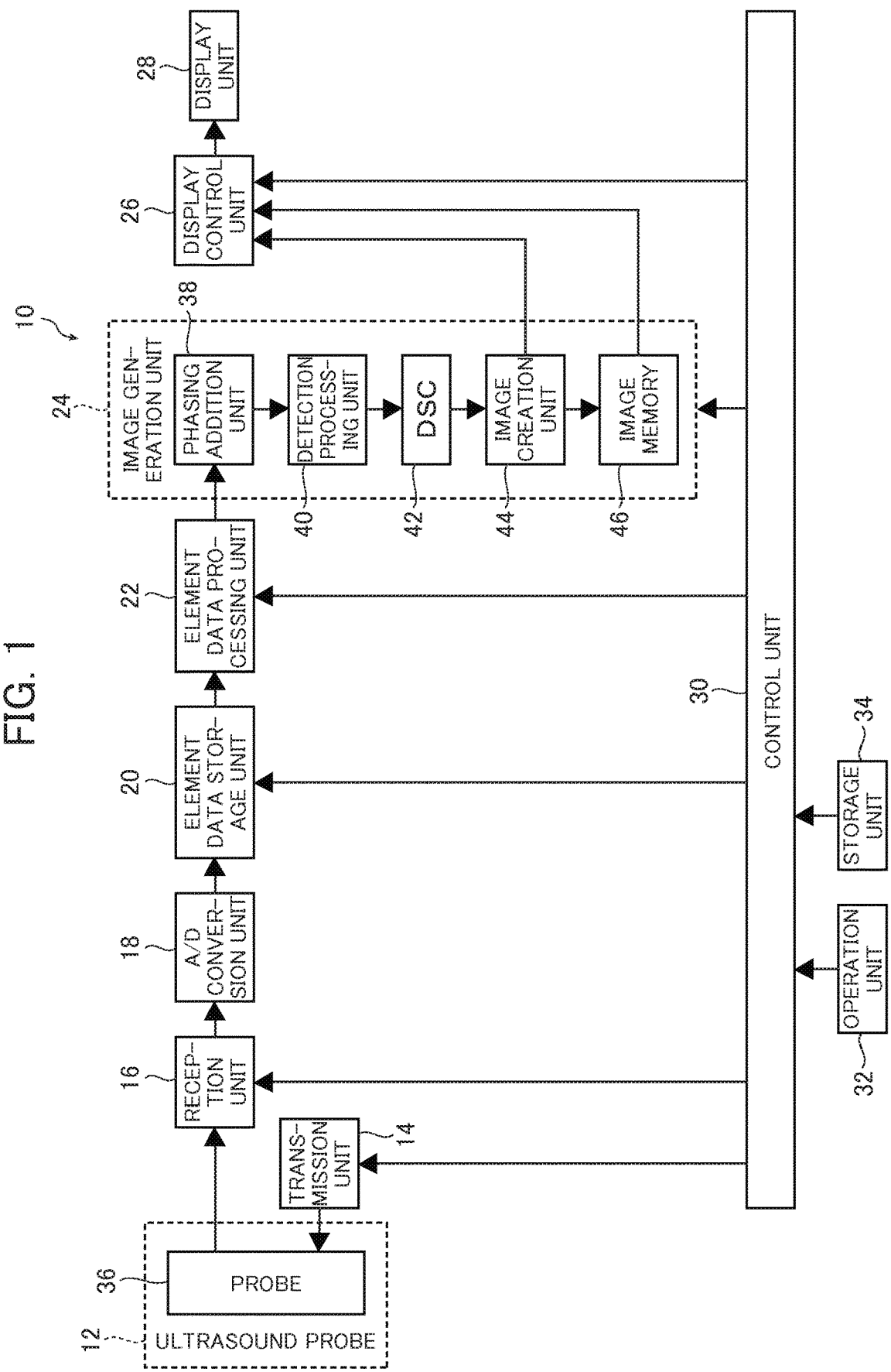

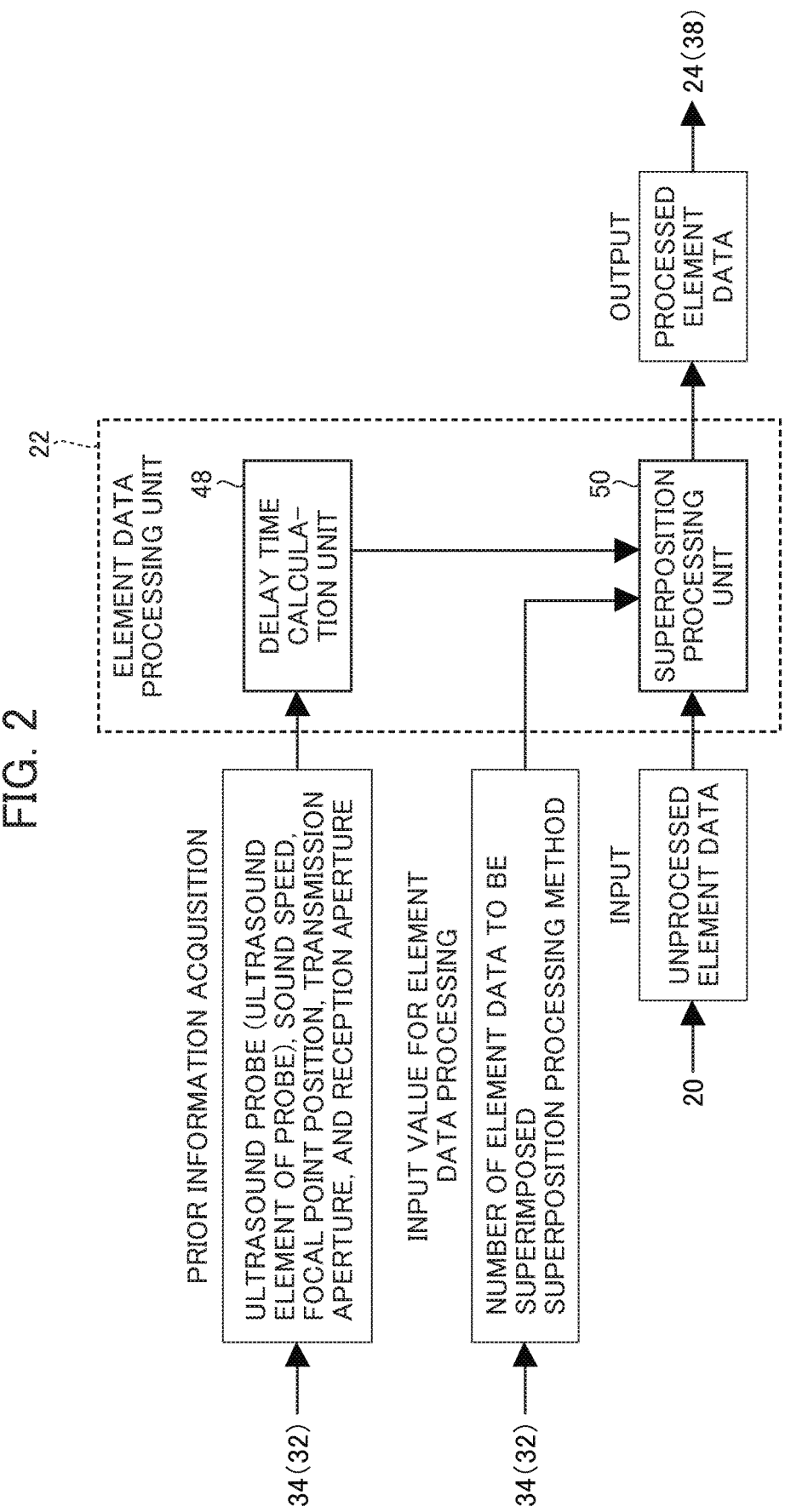

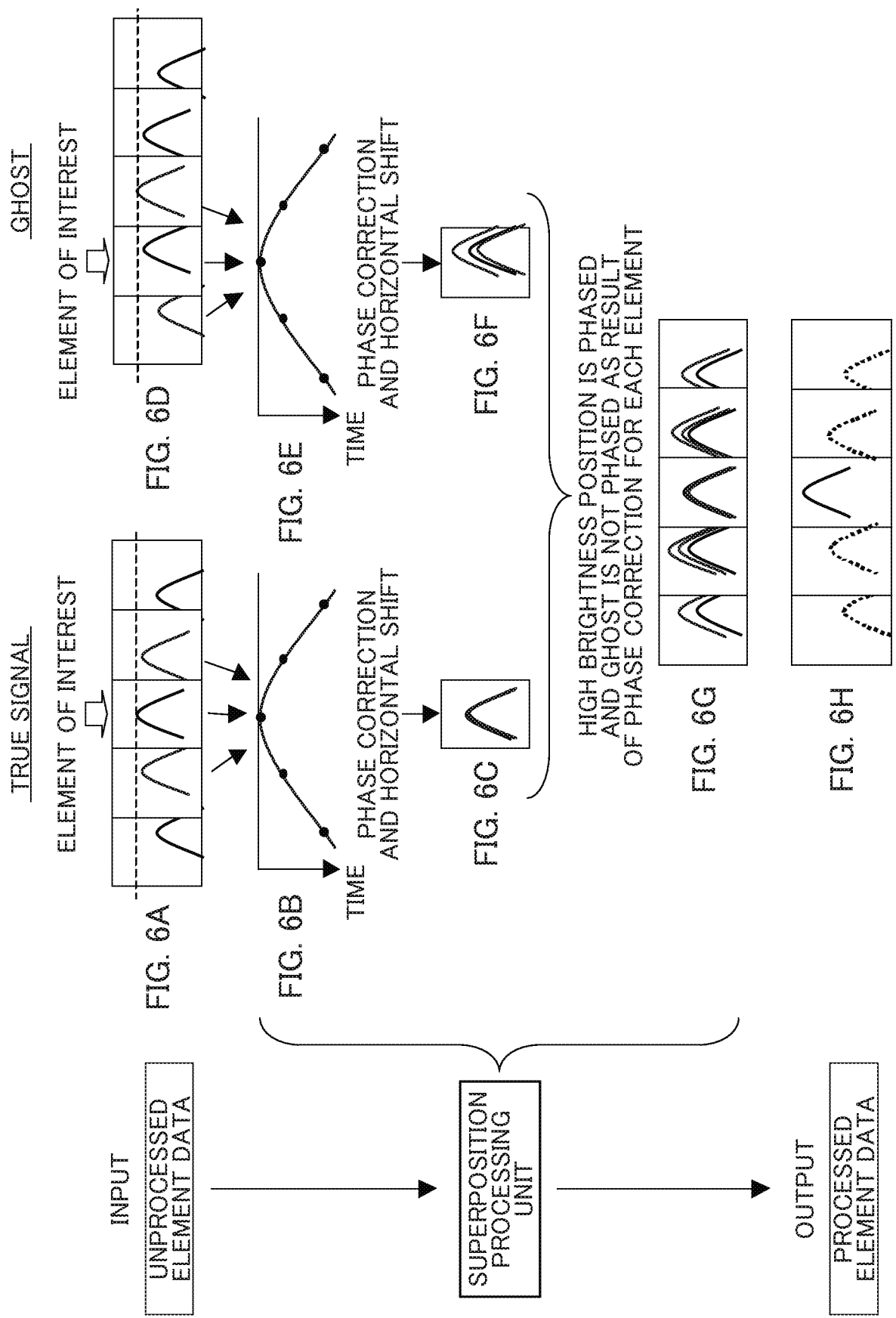

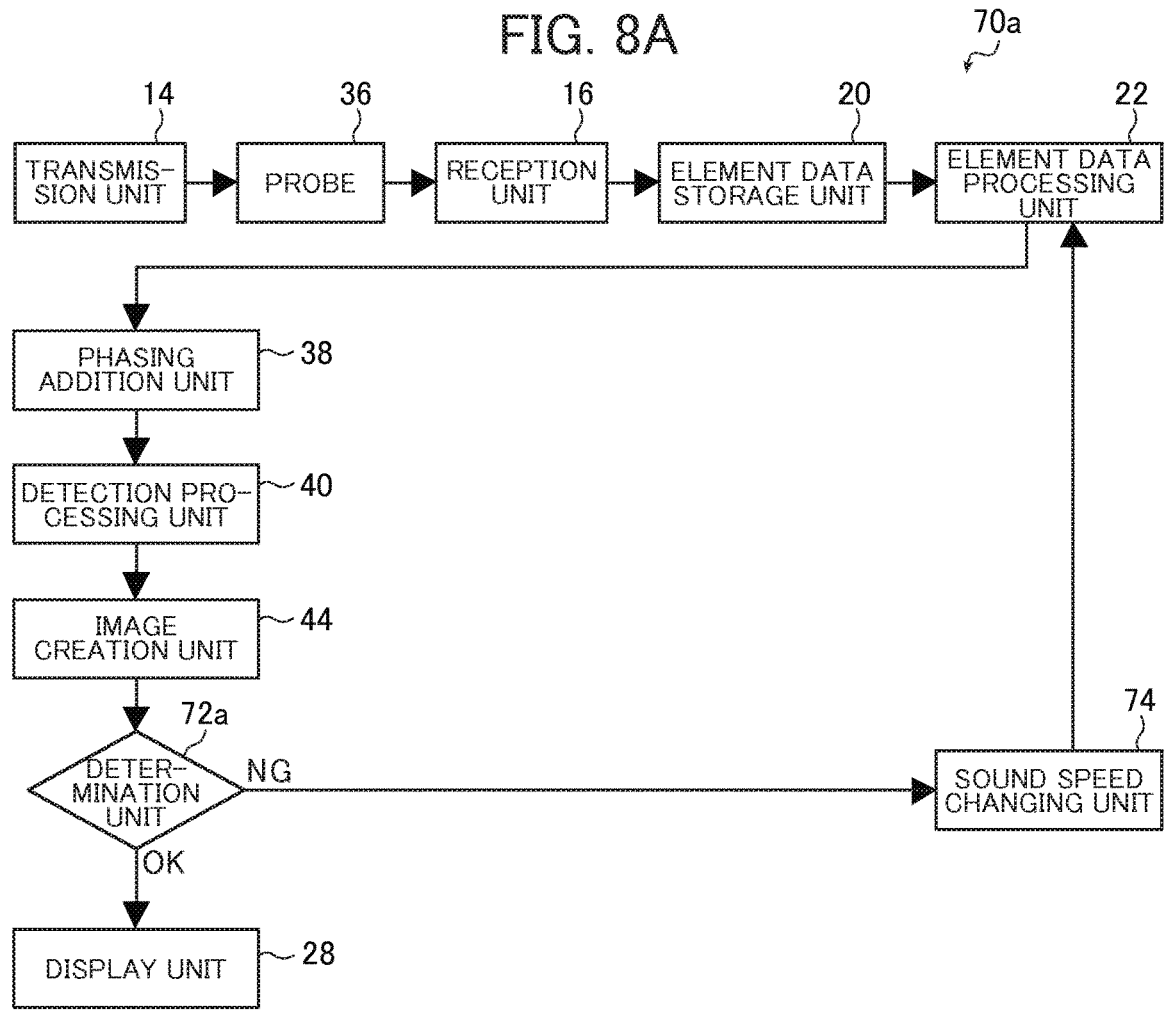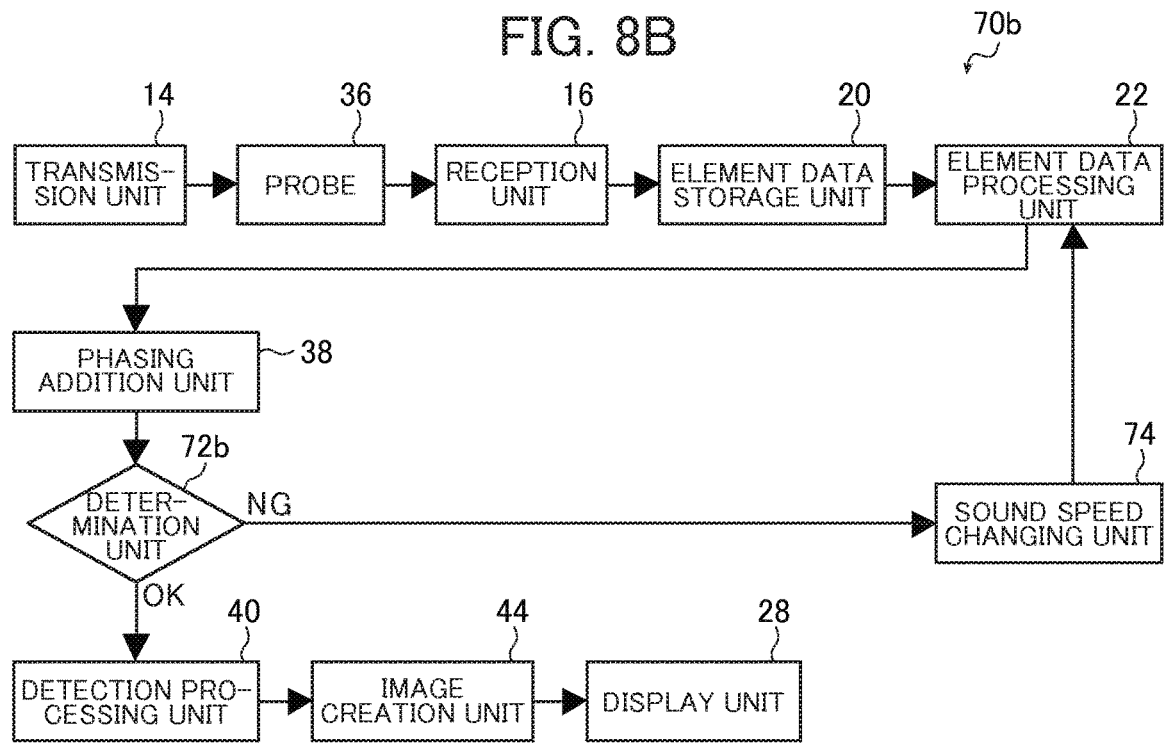

ULTRASONIC INSPECTION APPARATUS

CROSS-REFERENCE TO RELATED APPLICATIONS

This application is a Continuation of PCT International Application No. PCT/JP2013/069010 filed on Jul. 11, 2013, which claims priority under 35 U.S.C. § 119(a) to Japanese Application No. 2012-158009 filed on Jul. 13, 2012 and Japanese Application No. 2013-144809 filed on Jul. 10, 2013. Each of the above application(s) is hereby expressly incorporated by reference, in its entirety, into the present application.

BACKGROUND OF THE INVENTION

The present invention relates to an ultrasonic inspection apparatus for generating an ultrasound image to be used for inspection or diagnosis of an inspection target by imaging an inspection target such as organ in a living body by transmitting and receiving an ultrasonic beam.

An ultrasonic inspection apparatus using an ultrasound image such as an ultrasound diagnostic apparatus has hitherto been put into practical use in the field of medicine. In general, this kind of ultrasonic inspection apparatus has an ultrasound probe in which a plurality of elements (transducers) is installed, and an apparatus body connected to the ultrasound probe. In the ultrasonic inspection apparatus, an ultrasonic beam is transmitted from the plurality of elements of the ultrasound probe toward an inspection target (subject), an ultrasonic echo from the subject is received by the ultrasound probe, and a signal of the received ultrasonic echo is electrically processed in the apparatus body to generate an ultrasound image.

In an ultrasonic inspection apparatus, when an ultrasound image is generated, the ultrasonic beam is transmitted from the plurality of elements of the probe to an inspection target region of the subject, such as an organ in a living body or a lesion of the organ in a state of being focused thereon, and the ultrasonic echo from a reflector of the inspection target region such as a surface or an interface of the organ or the lesion is received through the plurality of elements. At this time, since ultrasonic echoes reflected by the same reflector are received by the plurality of elements, compared with an ultrasonic echo signal obtained by transmitting an ultrasonic beam from a transmission element and receiving an ultrasonic echo from a reflector located in a focal position of the ultrasonic beam transmitted with the transmission element, an ultrasonic echo signal obtained by receiving an ultrasonic echo reflected by the same reflector with another element different from the transmission element is delayed. Therefore, after an analog/digital (A/D) conversion is performed on the ultrasonic echo signals received by the plurality of elements to obtain element data, reception focus processing, that is, delay correction, phase matching, and phasing addition are performed on the element data to generate a sound ray signal, and an ultrasound image is generated based on the sound ray signal obtained in this way.

In the ultrasonic inspection technology, when the inspection target region of the subject is large, a large number of transmission ultrasonic beams are necessary, and the time required for image generation becomes long. Therefore, in order to improve the conventional technology in which the resolution of an ultrasound image generated depends on the width of the transmission ultrasonic beam, JP 2003-180688 A (Patent document 1) discloses a technology in which an ultrasound image is generated by using a system for generating an ultrasonic beam having a large width and an algorithm for converting a reception ultrasonic echo into image information.

In Patent document 1, first, an ultrasonic beam that is wider than a normal ultrasonic beam (see FIG. 12B in Patent document 1) is designed and transmitted and reception data is obtained (see FIG. 4 therein). In Patent document 1, a polar coordinate (radius R and angle θ) is assigned to a wide beam, and an ultrasound image is generated based on the relationship between the reception data and the geometric coordinate. In the ultrasound image generated in this way, the frame rate of the image increases in comparison with the conventional technology, and the resolution of the image can be improved with respect to the image forming time.

Further, JP 2011-011045 A (Patent document 2) discloses an ultrasound diagnostic apparatus in which a wide ultrasonic beam covering an area of a tissue of a subject is transmitted from a plurality of elements (ultrasound transducers) while performing element shifting of more than one element; parallel raw data (element data) including information of the area of the tissue generated based on a plurality of reception signals due to the ultrasonic echo from the area of the tissue is converted into serial raw data; reception focus processing is performed on the converted raw data to generate an image signal (sound ray signal); and an ultrasound image is generated based on the obtained sound ray signal.

Patent document 2 discloses that when the sound ray signal is generated, one sound ray signal can be generated by transmitting the ultrasonic beam so that two adjacent areas overlap each other and performing signal processing (for example, reception focus processing) using the raw data (element data) obtained through a plurality of transmissions on one sampling point in the overlapped area, thereby a resolution which is degraded due to a widened SN ratio or aperture can be improved. Patent document 2 also discloses that one sound ray signal of which a resolution which is degraded due to the widened SN ratio or aperture is improved can be obtained by generating a plurality of sound ray signals for one sampling point based on the raw data obtained through the plurality of transmissions, and then obtaining an average value of the sound ray signals.

JP 2009-240700 A (Patent document 3) discloses an ultrasound diagnostic apparatus in which transmission ultrasonic waves emitted from a plurality of vibrator constituting a vibrator group for transmission are focused on a transmission focusing point to form a virtual point sound source; reception ultrasonic waves reflected from a plurality of continuous observation points due to the transmission ultrasonic waves emitted from the point sound source are received by a plurality of vibrators constituting a vibrator group for reception; reception phasing addition is performed on each of the reception signals of the channels obtained so that the observation point forms a reception focusing point; further, the same reception phasing addition is performed on the reception signal obtained using each of the vibrator group for reception and the vibrator group for transmission sequentially shifted in an arrangement direction of the vibrator; and transmission phasing addition of correcting a transmission delay caused by a difference in a propagation distance from each transmission focusing point to the observation point on the reception signal after the reception phasing addition.

In Patent document 3, a transmission beam and a reception beam having a narrow beam width that is approximately uniform in a depth direction of a subject can be formed with high precision and high sensitivity by performing the reception phasing addition and the transmission phasing addition on the reception signals obtained from the plurality of vibrators. Accordingly, Patent document 3 discloses that image data having excellent spatial resolution, contrast resolution and S/N can be generated and displayed.

SUMMARY OF THE INVENTION

However, in the technology disclosed in Patent document 1, since a wide ultrasonic beam is used, the strength of the ultrasonic beam decreases in comparison with the conventional technology, and accordingly, there are problems in that an SN ratio (S/N) is degraded, and a dedicated ultrasound probe for generating a wide ultrasonic beam is necessary.

Further, in the technology disclosed in Patent document 2, deterioration of the SN ratio or the resolution due to the wide ultrasonic beam is improved by overlapping adjacent areas of the wide ultrasonic beam from a plurality of elements. However, this merely obtains one sound ray signal by performing reception focus processing on a plurality of pieces of raw data with respect to one sampling point of the overlapped adjacent area, or obtains one sound ray signal by performing reception focus processing on a plurality of pieces of raw data to obtain the respective sound ray signals and calculating an average value thereof. Therefore, improvement of deterioration of the SN ratio or the resolution caused by the use of wide ultrasonic beam is limited, and accordingly, there are problems in that further improvement of the SN ratio cannot be achieved, and an ultrasound image of a sufficient SN ratio cannot be obtained.

In contrast, in the technology disclosed in Patent document 3, an image having higher quality than that in the conventional technology is obtained, but in order to creating data of one line, it is necessary to generate a plurality of transmission beams while changing a transmission position, and thus the number of transmissions increases in comparison with the conventional technology. Therefore, there are problems in that the frame rate is decreased and real-time properties are deteriorated.

The present invention has been made in order to solve the problems in the above-described prior art, and an object thereof is to provide an ultrasonic inspection apparatus capable of reducing influence of the spread of a transmission ultrasonic beam, increasing an SN ratio, increasing a resolution, and thus obtaining a sharp ultrasound image having an optimal spatial resolution with high resolution that does not depend on a width of a transmission ultrasonic beam, without using a dedicated ultrasound probe for generating a wide transmission ultrasonic beam and at a frame rate that is not different from the conventional frame rate, by superimposing pieces of element data acquired through transmission from two or more different elements when ultrasonic beams are transmitted from a plurality of elements of a ultrasound probe.

In order to achieve the aforementioned object, the present invention provides an ultrasonic inspection apparatus that inspects an inspection target using an ultrasonic beam, the ultrasonic inspection apparatus comprising:

a probe that transmits the ultrasonic beam, receives an ultrasonic echo reflected by the inspection target, and outputs an analog element signal according to the received ultrasonic echo, a plurality of elements being arranged in the probe;

a transmission unit configured to perform, a plurality of times, to cause the probe to transmit the ultrasonic beam so as to form a predetermined transmission focal point using the plurality of elements;

a reception unit configured to receive analog element signals output by the plurality of elements corresponding to the transmission of individual ultrasonic beams and perform predetermined processing;

an A/D conversion unit configured to perform A/D conversion on the analog element signal processed by the reception unit to obtain first element data that is a digital element signal; and a data processing unit configured to generate second element data corresponding to any one of the pieces of first element data from a plurality of the pieces of first element data, wherein the data processing unit changes conditions of acquisition of two or more of the pieces of first element data for generating the second element data depending on a depth of a position in which the second element data is obtained.

In the ultrasonic inspection apparatus, it is preferable for the transmission unit to perform at least one of changing of a central element and changing of a transmission direction of the ultrasonic beam and cause the probe to perform a plurality of transmissions of the ultrasonic beam.

Further, it is preferable for the data processing unit to generate the second element data using at least one of the plurality of pieces of first element data obtained through transmissions of the ultrasonic beam in which central elements are different from each other and the plurality of pieces of first element data obtained through transmissions of the ultrasonic beams in which transmission directions differ from each other.

It is preferable for the data processing unit to generate the second element data from the plurality of pieces of first element data obtained through transmissions of the ultrasonic beam in which transmission areas overlap.

It is preferable for the data processing unit to superimpose the plurality of pieces of first element data based on a reception time at which the element receives the ultrasonic echo and a position of the element to generate the second element data.

It is preferable for the data processing unit to include a delay time calculation unit configured to calculate a delay time of two or more pieces of the first element data, and a superposition processing unit configured to superimpose the two or more pieces of first element data based on the calculated delay time and a reception position of the element of the probe to generate the second element data.

It is preferable that the delay time calculation unit calculates the delay time of the two or more pieces of first element data based on at least one piece of information acquired in advance regarding the probe, a sound speed of the inspection target, a focal point position of the ultrasonic beam, a transmission aperture of the probe by the transmission unit, and a reception aperture of the probe by the reception unit, and the superposition processing unit superimposes the two or more pieces of first element data based on the number of pieces of first element data to be superimposed on a reception time among the two or more pieces of first element data and a superposition processing method, that are set in advance, to generate at least one piece of second element data.

It is preferable for the data processing unit to generate the second element data from element data of only a superimposed portion when the two or more pieces of first element data are superimposed by the superposition processing unit.

It is preferable for the data processing unit to superimpose the two or more pieces of first element data after multiplying each of the pieces of first element data by a weighting coefficient.

It is preferable for the data processing unit to change the number of pieces of the first element data to be selected depending on the depth of the position in which the second element data is obtained.

It is preferable for the data processing unit adaptively superimposes the two or more pieces of first element data based on at least two or more different points on a time axis on a reception time of each piece of element data.

It is preferable for the different point on the time axis to be based on each transmission aperture of the probe by the transmission unit, and more preferable to be based on each transmission aperture when transmission is performed in at least two or more transmission apertures for each of the two or more pieces of first element data, or it is preferable for the different point on the time axis to be based on the sound speed of the inspection target.

It is preferable that when the transmission unit transmits the ultrasonic beams forming a transmission focal point of a different depth on the same transmission line for each transmission line, the reception unit acquires the plurality of pieces of first element data corresponding to the same transmission line, and the data processing unit generates the second element data from the plurality of pieces of first element data obtained through transmission and reception of the ultrasonic beam of the transmission focal point of the same depth for each depth of the transmission focal point.

It is preferable for the data processing unit to change the number of pieces of the first element data to be selected depending on the depth of the position in which the corresponding second element data is obtained based on a spatial spread of the ultrasonic beam within the inspection target, or it is preferable for the data processing unit to change the number of pieces of the first element data to be selected depending on the depth of the position in which the corresponding second element data is obtained based on a signal in a spatial position within the inspection target.

It is preferable for the data processing unit to change the number of pieces of the first element data to be selected depending on the depth of the position in which corresponding second element data is obtained based on a result of waveform analysis of the first element data.

It is preferable for the waveform analysis to include analyzing of relevance or a coherence characteristic of a waveform regarding a candidate of the first element data to be selected.

It is preferable for the data processing unit to obtain the optimal number of pieces of element data based on a signal in the plurality of pieces of second element data created by changing the number of pieces of the first element data to be selected.

It is preferable that the transmission unit determines a transmission focal point depth depending on the depth of the position in which the second element data is obtained, and causes the probe to perform transmission of the ultrasonic beam a plurality of times at the determined transmission focal point depth to acquire the plurality of pieces of first element data, and the data processing unit selects two or more pieces of the first element data for generating the second element data from among the plurality of pieces of first element data obtained through the transmission of the ultrasonic beam of the determined transmission focal point depth.

It is preferable that the transmission unit determines a transmission numerical aperture depending on the depth of the position in which the second element data is obtained, and causes the probe to perform the transmission of the ultrasonic beam using the determined transmission numerical aperture a plurality of times to acquire the plurality of pieces of first element data, and the data processing unit selects two or more pieces of the first element data for generating the second element data from among the plurality of pieces of first element data obtained through the transmission of the ultrasonic beam using the determined transmission numerical aperture.

It is preferable for the transmission unit to cause the probe to perform steering transmission.

It is preferable for the element data to include phase information and amplitude information.

It is preferable for the ultrasonic inspection apparatus to further include an element data storage unit configured to store at least one of the first element data and the second element data.

It is preferable for the data processing unit to perform phasing addition of each of the plurality of pieces of first element data to generate a plurality of pieces of first reception data directly before generating the second element data from the plurality of pieces of first element data, and generate second reception data corresponding to any one of the pieces of first reception data from the plurality of pieces of first reception data.

Further, in order to achieve the aforementioned object, the present invention provides an ultrasonic inspection apparatus that inspects an inspection target using an ultrasonic beam, the ultrasonic inspection apparatus comprising:

a probe that transmits the ultrasonic beam, receives an ultrasonic echo reflected by the inspection target, and outputs an analog element signal according to the received ultrasonic echo, a plurality of elements being arranged in the probe;

a transmission unit configured to perform, a plurality of times, to cause the probe to transmit the ultrasonic beam so as to form a predetermined transmission focal point using the plurality of elements;

a reception unit configured to receive analog element signals output by the plurality of elements corresponding to transmission of the individual ultrasonic beams and perform a predetermined processing;

an A/D conversion unit configured to perform A/D conversion on the analog element signal processed by the reception unit to obtain first element data that is a digital element signal;

a phasing addition unit configured to perform phasing addition on the plurality of pieces of first element data around a line corresponding to the same element to generate a plurality of pieces of first reception data; and a data processing unit configured to generate second reception data corresponding to any one of the pieces of first reception data from a plurality of the pieces of first reception data, wherein the data processing unit changes conditions of acquisition of two or more of the pieces of first reception data for generating the second reception data depending on a depth of a position in which the second reception data is obtained.

Moreover, in order to achieve the aforementioned object, the present invention provides an ultrasonic inspection apparatus that inspects an inspection target using an ultrasonic beam, the ultrasonic inspection apparatus comprising:

a probe that transmits the ultrasonic beam, receives an ultrasonic echo reflected by the inspection target, and outputs an analog element signal according to the received ultrasonic echo, a plurality of elements being arranged in the probe;

a transmission unit configured to perform, a plurality of times, to cause the probe to transmit the ultrasonic beam so as to form a predetermined transmission focal point using the plurality of elements;

a reception unit configured to receive analog element signals output by the plurality of elements corresponding to transmission of the individual ultrasonic beams and perform a predetermined processing;

an A/D conversion unit configured to perform A/D conversion on the analog element signal processed by the reception unit to obtain first element data that is a digital element signal;

a data processing unit configured to generate second element data corresponding to any one of the pieces of first element data from a plurality of the pieces of first element data; and a mode switching unit configured to switch a first mode in which an ultrasound image is generated using the first element data and a second mode in which an ultrasound image is generated using the second element data generated by the data processing unit, wherein an F value when the transmission unit causes the probe to transmit the ultrasonic beam is switched in response to switching of mode by the mode switching unit, and the data processing unit generates the second element data corresponding to any one of the pieces of first element data from a plurality of the pieces of first element data obtained based on the F value that is switched when the mode switching unit performs the switching of mode.

In the ultrasonic inspection apparatus, it is preferable for the data processing unit to generate the second element data corresponding to any one of the pieces of first element data from a plurality of the pieces of first element data obtained based on the F value that is switched when the mode switching unit performs the switching of mode.

Further, it is preferable for the F value when the second mode is selected to be smaller than the F value when the first mode is selected.

It is preferable for the first element data to be acquired by transmitting the ultrasonic beam so that the F value is constant regardless of the depth of the focal point position of the ultrasonic beam.

Furthermore, in order to achieve the aforementioned object, the present invention provides an ultrasonic inspection apparatus that inspects an inspection target using an ultrasonic beam, the ultrasonic inspection apparatus comprising:

a probe that transmits the ultrasonic beam, receives an ultrasonic echo reflected by the inspection target, and outputs an analog element signal according to the received ultrasonic echo, a plurality of elements being arranged in the probe;

a transmission unit configured to perform, a plurality of times, to cause the probe to transmit the ultrasonic beam so as to form a predetermined transmission focal point using the plurality of elements;

a reception unit configured to receive analog element signals output by the plurality of elements corresponding to transmission of the individual ultrasonic beams and perform a predetermined processing;

an A/D conversion unit configured to perform A/D conversion on the analog element signal processed by the reception unit to obtain first element data that is a digital element signal;

a data processing unit configured to generate second element data corresponding to any one of the pieces of first element data from a plurality of the pieces of first element data; and at least one sound speed setting unit configured to determine a sound speed in the inspection target, wherein the data processing unit generates the second element data based on the sound speed obtained in the sound speed setting unit.

In the ultrasonic inspection apparatus, it is preferable that the data processing unit calculates the delay time of two or more of the pieces of first element data using the sound speed within the inspection target, and superimposes the two or more of pieces of first element data based on the calculated delay time to generate second element data; that the at least one sound speed setting unit includes a first sound speed setting unit that sets sound speed of the inspection target to be used for delay time calculation in the data processing unit, and a phasing addition unit that performs phasing addition of the second element data, which is obtained by the data processing unit using the sound speed set in the first sound speed setting unit, to generate a sound ray signal, a first determination unit that determines the suitability of the sound ray signal obtained by the phasing addition unit, and an image generation unit that generates an ultrasound image based on the sound ray signal generated by the phasing addition unit are included; and that when a determination result of the first determination unit is "unsuitable", the first sound speed setting unit newly sets another sound speed again, the data processing unit calculates the delay time again using the sound speed set again and obtains the second element data based on the delay time calculated again, the phasing addition unit generates the sound ray signal again using the second element data obtained again, and the aforementioned processing in the first sound speed setting unit, the data processing unit and the phasing addition unit are repeated until the determination result of the first determination unit based on the sound ray signal generated again is "suitable", and when the determination result of the first determination unit is "suitable", the image generation unit generates an ultrasound image based on the sound ray signal.

Further, it is preferable for the first sound speed setting unit to set the sound speed in at least one point on the reception time for each element data.

It is preferable that a second sound speed setting unit that obtains an optimal sound speed of a reception side based on second element data generated when a determination result of the first determination unit is "suitable", a phasing addition unit that performs phasing addition of the second element data using the optimal sound speed obtained by the second sound speed setting unit to generate a sound ray signal, and a second determination unit that determines the suitability of the sound ray signal obtained by the phasing addition unit are included; and that when the determination result of the second determination unit is "unsuitable", the second sound speed setting unit obtains the optimal sound speed again based on the second element data, the phasing addition unit generates the sound ray signal again using the optimal sound speed obtained again, and the aforementioned processing in the second sound speed setting unit and the phasing addition unit are repeated until the determination result of the second determination unit based on the sound ray signal generated again is "suitable", and when the determination result of the second determination unit is "suitable", the image generation unit generates the ultrasound image based on the sound ray signal.

Further, it is preferable for the second sound speed setting unit to set the sound speed in at least one point on the reception time for each element data.

It is preferable that a third sound speed setting unit that obtains an optimal sound speed of a reception side based on the first element data, a phasing addition unit that performs phasing addition of the first element data using the optimal sound speed obtained by the third sound speed setting unit to generate a sound ray signal, and a third determination unit that determines the suitability of the sound ray signal obtained by the phasing addition unit are included; and that when the determination result of the third determination unit is "unsuitable", the third sound speed setting unit obtains the optimal sound speed again based on the first element data, the phasing addition unit generates the sound ray signal again using the optimal sound speed obtained again, and the aforementioned processing in the third sound speed setting unit and the phasing addition unit are repeated until the determination result of the third determination unit based on the sound ray signal generated again is "suitable", and when the determination result of the third determination unit is "suitable", the delay time calculation unit sets the obtained optimal sound speed as the sound speed of the inspection target.

It is preferable for the third sound speed setting unit to set the sound speed in at least one point on the reception time for each element data.

It is preferable for the third sound speed setting unit to be the same as the second sound speed setting unit.

It is preferable for the third determination unit to be the same as the second determination unit.

Further, it is preferable that the at least one sound speed setting unit includes a fourth sound speed setting unit that obtains an optimal sound speed of a reception side based on the second element data generated using the predetermined sound speed in the data processing unit, and a phasing addition unit that generates a sound ray signal by performing phasing addition of the second element data using the optimal sound speed obtained by the fourth sound speed, a fourth determination unit that determines the suitability of the sound ray signal obtained by the phasing addition unit, and an image generation unit that generates an ultrasound image based on the sound ray signal generated by the phasing addition unit are included; and that when the determination result of the fourth determination unit is "unsuitable", the data processing unit performs processing of generating the second element data again using the optimal sound speed obtained by the fourth sound speed setting unit, the fourth sound speed setting unit obtains the optimal sound speed again based on the second element data generated again, the phasing addition unit generates the sound ray signal using the optimal sound speed obtained again, and the aforementioned processing in the data processing unit, the fourth sound speed setting unit and the phasing addition unit are repeated until the determination result of the fourth determination unit based on the sound ray signal generated again is "suitable", and when the determination result of the fourth determination unit is "suitable", the image generation unit generates the ultrasound image based on the sound ray signal.

Further, it is preferable for the fourth sound speed setting unit to set the sound speed in at least one point on the reception time of each element data.

It is preferable for the fourth sound speed setting unit to be the same as the second sound speed setting unit and third sound speed setting unit.

It is preferable for the fourth determination unit to be the same as the second determination unit and the third determination unit.

In addition, in order to achieve the aforementioned object, the present invention provides an ultrasonic inspection apparatus that inspects an inspection target using an ultrasonic beam, the ultrasonic inspection apparatus comprising:

a probe that transmits the ultrasonic beam, receives an ultrasonic echo reflected by the inspection target, and outputs an analog element signal according to the received ultrasonic echo, a plurality of elements being arranged in the probe;

a transmission unit configured to perform, a plurality of times, to cause the probe to transmit the ultrasonic beam so as to form a predetermined transmission focal point using the plurality of elements;

a reception unit configured to receive analog element signals output by the plurality of elements corresponding to transmission of the individual ultrasonic beams and perform a predetermined processing;

an A/D conversion unit configured to perform A/D conversion on the analog element signal processed by the reception unit to obtain first element data that is a digital element signal;

a data processing unit configured to generate second element data corresponding to any one of the pieces of first element data from a plurality of the pieces of first element data;

a first image generation unit configured to generate a first ultrasound image based on the first element data;

a second image generation unit configured to generate a second ultrasound image based on the second element data;

an image quality determination unit configured to compare image quality of the first ultrasound image generated by the first image generation unit with image quality of the second ultrasound image generated by the second image generation unit; and a third image generation unit configured to generate a third ultrasound image for being used in an ultrasonic inspection from the first ultrasound image and the second ultrasound image based on a result of an image quality determination performed by the image quality determination unit.

In the ultrasonic inspection apparatus, it is preferable for the image quality determination unit to perform the image quality determination using any one of a brightness value, contrast and graininess of the first ultrasound image and second ultrasound image, or using a combination of two or more of them.

Further, it is preferable for the third image generation unit to adopt any one of the first ultrasound image and the second ultrasound image as the ultrasound image for being used in the ultrasonic inspection based on a result of the image quality determination of the image quality determination unit.

It is preferable that a region division unit configured to divide the first ultrasound image and the second ultrasound image into a plurality of regions is further included; the image quality determination unit performs the image quality determination of the first ultrasound image and second ultrasound image for each of the regions divided by the region division unit; and the third image generation unit selects any one of the first ultrasound image and the second ultrasound image for each of the regions, as an ultrasound image of the corresponding region, based on a result of the image quality determination of the image quality determination unit, and combine the images selected in the respective regions to generate the third ultrasound image.

According to the present invention, when ultrasonic beams are transmitted from the plurality of elements of the ultrasound probe, by superimposing the pieces of element data acquired through the transmission from two or more different elements, it is possible to reduce the influence of the spread of the transmission ultrasonic beam, to increase an SN ratio, to increase resolution, and thus to obtain a sharp ultrasound image having an optimal spatial resolution with high resolution that does not depend on the width of the transmission beam, without using a dedicated ultrasound probe for generating a wide transmission ultrasonic beam and at a frame rate that is not different from the conventional frame rate.

BRIEF DESCRIPTION OF THE DRAWINGS

FIG. 1 is a block diagram conceptually illustrating an example of a configuration of an ultrasonic inspection apparatus of Embodiment 1 according to the present invention.

FIG. 2 is a block diagram conceptually illustrating an example of a configuration of an element data processing unit of the ultrasonic inspection apparatus illustrated in FIG. 1.

FIGS. 6A, 6B and 6C, as well as 6D, 6E and 6F are illustrative diagrams illustrating pieces of element data obtained by a plurality of elements, a delay time thereof, and a superposition state of pieces of element data in the case of a true signal and a ghost, respectively, and FIGS. 6G and 6H are illustrative diagrams illustrating a superposition state of pieces of element data corresponding to the plurality of elements, and a result of superposition processing thereof, respectively.

FIGS. 8A and 8B are block diagrams conceptually illustrating, along a process flow, an example of primary units of an ultrasonic inspection apparatus of Embodiment 2 of the present invention.

DETAILED DESCRIPTION OF THE INVENTION

Figure 3B:
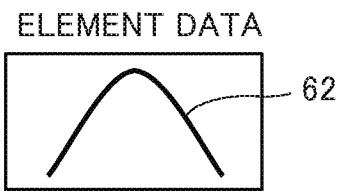
FIGS. 3B and 3D are illustrative diagrams illustrating respective pieces of element data obtained.

Hereinafter, an ultrasonic inspection apparatus according to the present invention will be described in detail based on preferred embodiments shown in the accompanying drawings.

Embodiment 1

FIG. 1 is a block diagram conceptually illustrating an example of a configuration of an ultrasonic inspection apparatus of Embodiment 1 according to the present invention.

An ultrasonic inspection apparatus 10 includes an ultrasound probe 12, a transmission unit 14 and a reception unit 16 that are connected to the ultrasound probe 12, an A/D conversion unit 18, an element data storage unit 20, an element data processing unit 22, an image generation unit 24, a display control unit 26, a display unit 28, a control unit 30, an operation unit 32, and a storage unit 34, as illustrated in FIG. 1.

The ultrasound probe 12 includes a probe 36 used in an ordinary ultrasonic inspection apparatus.

The probe 36 has a plurality of elements, that is, transducers which are one-dimensionally or two-dimensionally arranged. When an ultrasound image of an inspection target (hereinafter referred to as a subject) is imaged, each of the plurality of ultrasound transducers transmits an ultrasonic beam toward the subject in accordance with a driving signal supplied from the transmission unit 14, receives an ultrasonic echo from the subject, and outputs a reception signal. In the present embodiment, each of a predetermined number of ultrasound transducers constituting one group among the plurality of ultrasound transducers of the probe 36 generates each component of one ultrasonic beam, and the one group of the predetermined number of ultrasound transducers generates one ultrasonic beam to be transmitted to the subject.

Each ultrasound transducer is constituted by an element, that is, a vibrator in which electrodes are formed at both ends of a piezoelectric substance formed of, for example, a piezoelectric ceramic represented by PZT (lead zirconate titanate), a polymer piezoelectric element represented by PVDF (polyvinylidene fluoride), a piezoelectric single crystal represented by PMN-PT (lead magnesium niobate-lead titanate solid solution), or the like. Namely, it can be said that the probe 36 is a vibrator array in which a plurality of vibrators are one-dimensionally or two-dimensionally arranged as a plurality of ultrasound element.

If a pulsed or continuous-wave voltage is applied across the electrodes of the vibrator, the piezoelectric substance expands and contracts, whereby pulsed or continuous-wave ultrasonic waves are generated from the vibrator, and the generated ultrasonic waves are synthesized to form an ultrasonic beam. When receiving propagating ultrasonic wave, each vibrator expands and contracts to generate an electric signal and the electric signal is output as a reception signal of the ultrasonic wave.

The transmission unit 14 includes a plurality of pulsers, for example. The transmission unit 14 adjusts the amount of delay of each driving signal so that ultrasonic beam components transmitted from the one group of the predetermined number of ultrasound transducers (hereinafter, ultrasound transducer is referred to as a ultrasound element) of the probe 36 forms one ultrasonic beam, depending on a sound speed or a distribution of sound speed set based on a transmission delay pattern selected according to a control signal from the control unit 30, and supplies the adjusted driving signals to the plurality of ultrasound elements constituting the group.

The reception unit 16 receives the ultrasonic echo, which is generated by an interaction between the ultrasonic beam and the subject, from the subject by each ultrasound element of the probe 36 according to a control signal from the control unit 30 to generate a reception signal, amplifies and outputs the reception signal, that is, an analog element signal for each ultrasound element, and supplies the amplified analog element signal to the A/D conversion unit 18.

The element data storage unit 20 sequentially stores digital element data (hereinafter referred to simply as element data) output from the A/D conversion unit 18. The element data is data indicating a relationship between position (element position) and reception time, and signal strength, and includes phase information and amplitude information.

Further, the element data storage unit 20 stores information (for example, a depth of a reflection position of the ultrasound waves, a density of scanning lines, or a parameter indicating a width of a field of view) regarding a frame rate input from the control unit 30 in association with the digital element data.

When at least two or more target regions overlapping each other in a target region on a position coordinate of two or more dimension, are inspected according to a control signal from the control unit 30, the element data storage unit 20 stores and holds two or more pieces of element data which are respectively generated for the two or more target regions from the ultrasonic echoes respectively received by the reception unit 16 for the two or more target regions. The element data stored and held in the element data storage unit 20 includes two or more pieces of element data, each of which includes reception data at every reception time.

The element data processing unit 22 is a characteristic unit in the present invention, and superimposes two or more pieces of element data respectively generated for two or more target regions (hereinafter referred to as unprocessed element data), which have been stored and held in the element data storage unit 20, while matching time on the reception time, based on control of the control unit 30 to generate element data subjected to this superposition processing (hereinafter, element data having been subjected to the superposition processing is referred to as processed element data).

Specifically, based on control of the control unit 30, the element data processing unit 22 superimposes pieces of element data obtained through transmission of a predetermined number of (a plurality of) ultrasonic beams in which central ultrasound transducers (central element) are different and transmission areas of the ultrasonic beams overlap among the pieces of element data stored in the element data storage unit 20, based on the time at which the ultrasound transducer receives the ultrasonic echo and a position of the ultrasound transducer to generate the processed element data corresponding to the element data (element data of an element of interest to be described below).

Details of the element data processing unit 22 will be described below.

The image generation unit 24 generates a sound ray signal (reception data) from the processed element data supplied from the element data processing unit 22 under the control of the control unit 30.

The image generation unit 24 includes a phasing addition unit 38, a detection processing unit 40, a DSC 42, an image creation unit 44, and an image memory 46.

The phasing addition unit 38 selects a reception delay pattern from among a plurality of reception delay patterns stored in advance according to a reception direction set in the control unit 30, gives a delay to each piece of the element data depending on a sound speed or a distribution of sound speed set based on the selected reception delay pattern, and adds pieces of the element data together to thereby perform reception focus processing. Reception data (sound ray signal) in which the focus of the ultrasonic echo is narrowed down is generated by this reception focus processing.

The phasing addition unit 38 supplies the reception data to the detection processing unit 40.

The detection processing unit 40 performs correction of attenuation due to distance on the reception data generated in the phasing addition unit 38 depending on the depth of the reflection position of the ultrasonic beam, and then performs envelope detection processing to generate B-mode image data that is tomographic image information regarding a tissue of the subject.

The DSC (digital scan converter) 42 converts (raster-converts) the B-mode image data generated in the detection processing unit 40 into image data corresponding to a scanning system of a normal television signal.

The image creation unit 44 performs various necessary image processing such as gradation processing on the B-mode image data input from the DSC 42 to create B-mode image data to be subjected to an inspection or a display, and then outputs the created B-mode image data for inspection or for display to the display control unit 46 for the purpose of displaying, or stores the B-mode image data in the image memory 46.

The image memory 46 temporarily stores the B-mode image data for inspection created in the image creation unit 44. The B-mode image data for inspection stored in the image memory 46 is read by the display control unit 26 to be displayed on the display unit 28 as necessary.

The display control unit 26 causes the display unit 28 to display an ultrasound image based on the B-mode image data for inspection subjected to the image processing by the image creation unit 44.

The display unit 28 includes, for example, a display device such as an LCD and displays an ultrasound image under the control of the display control unit 26.

The control unit 30 controls the respective units of the ultrasonic inspection apparatus 10 based on an instruction input from the operation unit 32 by an operator.

Here, when various information, in particular, information necessary for delay time calculation used in the element data processing unit 22 and the phasing addition unit 38 of the image generation unit 24 and information necessary for the element data processing in the element data processing unit 22 are input by the operator through the operation unit 32, the control unit 30 supplies, as necessary, the various information input from the operation unit 32 to the respective units such as the transmission unit 14, the reception unit 16, the element data storage unit 20, the element data processing unit 22, the image generation unit 24, and the display control unit 26.

The operation unit 32 is used when the operator performs input operation, and may be constituted by a keyboard, a mouse, a trackball, a touch panel, or the like.

The operation unit 32 includes an input device in which the operator performs, as necessary, the input operation for inputting various information, in particular, information used in the aforementioned delay time calculation such as information on the plurality of ultrasound elements of the probe 36 of the ultrasound probe 12, a sound speed in the inspection target region of the subject, a focal position of the ultrasonic beam, and a transmission aperture and a reception aperture of the probe 36 and information on the element data processing such as the number of pieces of the element data to be superimposed and a superposition processing method.

The storage unit 34 stores various information input from the operation unit 32, in particular, stores aforementioned information on the probe 12, the sound speed, the focal position, the transmission aperture, and the reception aperture; the aforementioned information on the element data processing such as the number of pieces of the element data to be superimposed and a superposition processing method; or information necessary for the processing or operation of the respective units controlled by the control unit 30 such as the transmission unit 14, the reception unit 16, the element data storage unit 20, the element data processing unit 22, the image generation unit 24, and the display control unit 26, and an operation program or a processing program for causing the respective units to execute the processing or operation as well. The storage unit 34 may be constituted by a recording medium such as a hard disk, a flexible disk, an MO, an MT, a RAM, a CD-ROM a DVD-ROM, or the like.

The element data processing unit 22, the phasing addition unit 38, the detection processing unit 40, the DCS 42, the image creation unit 44, and the display control unit 26 are constituted by a CPU and an operation program for causing the CPU to execute various processing, but these may be constituted by digital circuits.

Here, the element data processing unit 22 will be described in detail based on FIG. 2.

The element data processing unit 22 includes a delay time calculation unit 48 and a superposition processing unit 50, as illustrated in FIG. 2.

The delay time calculation unit 48 acquires, in advance, information on the plurality of ultrasound elements of the probe 36 of the ultrasound probe 12, the sound speed in the inspection target region of the subject, the focal position of the ultrasonic beam, the transmission aperture and the reception aperture of the probe 36, and the like, which is input from the operation unit 32 or input from the operation unit 32 and stored in the storage unit 34, and calculates the delay time of the element data received by each of the ultrasound elements of the reception aperture based on a geometric arrangement of the ultrasound element (transmission element) of the transmission aperture which forms and transmits an ultrasonic beam and the ultrasound element of the reception aperture which receives the ultrasonic echo caused by the ultrasonic beam from the subject.

The superposition processing unit 50 reads two or more pieces of unprocessed element data respectively generated for two or more target regions stored and held in the element data storage unit 20 based on information on element data processing such as the number of pieces of element data to be superimposed and a superposition processing method, which is input from the operation unit 32 or input from the operation unit 32 and stored in the storage unit 34, and superimposes the two or more pieces of unprocessed element data while matching the reception time and matching absolute positions of the element of the probe which receives an ultrasonic echo based on the respective delay time calculated by the delay time calculation unit 48 to generate the processed element data.

Next, element data processing performed in the element data processing unit 22 will be described in detail.

First, a relationship between an ultrasonic beam (hereinafter referred to simply as a transmission beam) transmitted from an ultrasound element for transmission of the probe 36 of the ultrasound probe 12 (hereinafter referred to simply as a transmission element) and element data obtained by an ultrasound element for reception of the probe 36 (hereinafter referred to simply as a reception element) when the transmission beam is transmitted from the transmission element to a subject and an ultrasonic echo generated by interaction of the transmission beam with the subject is received by the reception element to obtain element data will be described.

Figure 3D:
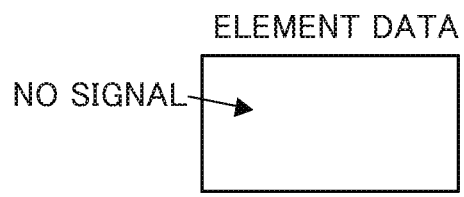
Figure 3A:
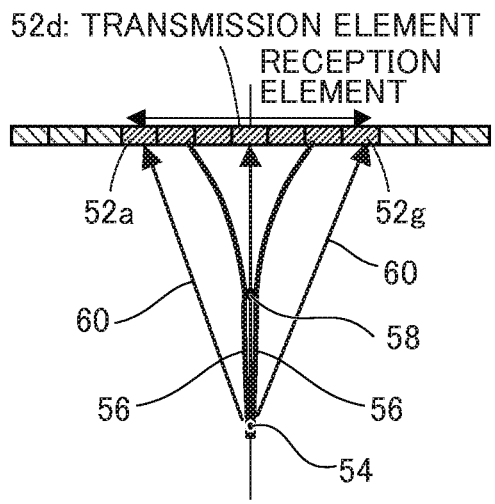
FIGS. 3A and 3C are illustrative diagrams when ideal ultrasonic beams are transmitted from an element just above a reflection point of a subject and an element that is not just above the reflection point, respectively.

When the ultrasonic echo is received using seven ultrasound elements (hereinafter also referred to simply as elements) 52a to 52g and seven ultrasound elements 52b to 52h as reception elements to acquire element data as respectively illustrated in FIGS. 3A and 3C, in an ideal case in which a transmission beam 56 transmitted to an inspection target region including a reflection point 54 is ideally narrowed down to be smaller than an element interval, if the central element 52d just above the reflection point 54 in the inspection target region among the elements 52a to 52g is used as the transmission element to transmit the transmission beam 56, and the ultrasonic echo is received using the reception elements 52a to 52g to acquire the element data, as illustrated in FIG. 3A, a focal point 58 of the transmission beam 56 is on a straight line that connects the element 52d with the reflection point 54, the transmission beam 56 is transmitted up to the reflection point 54, and accordingly, the ultrasonic echo reflected from the reflection point 54 is generated. The ultrasonic echo from the reflection point 54 is received by the reception elements 52a to 52g via the reception path 60 spreading at a predetermined angle, and element data 62 as illustrated in FIG. 3B is obtained by the reception elements 52a to 52g.

Figure 3C:
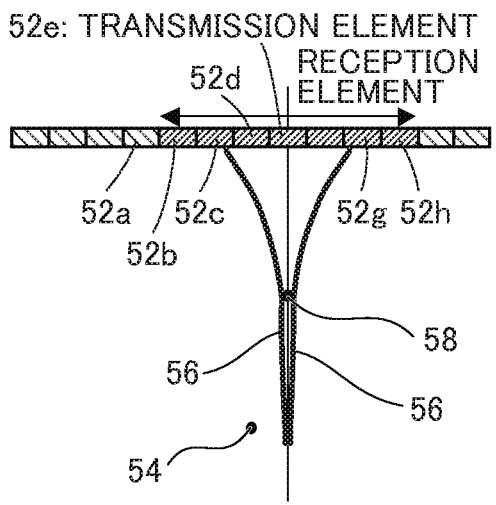

In contrast, in a case in which the center of the transmission elements is shifted by one element in an element direction (a right direction in FIG. 3C) relative to the reflection point 54, the transmission beam 56 is transmitted using the element 52e adjacent to the element 52d just above the reflection point 54 as the transmission element, and the ultrasonic echo is received by the reception elements 52b to 52h, as illustrated in FIG. 3C, since the reflection point 54 is not on the transmission direction of the transmission beam 56, that is, on a straight line that connects the transmission element 52e with the focal point 58, the transmission beam 56 is not transmitted to the reflection point 54. Therefore, the ultrasonic echo reflected from the reflection point 54 is not generated, the reception elements 52b to 52h do not receive the ultrasonic echo, and accordingly, a reflected signal from the reflection point is not obtained as illustrated in FIG. 3D (signal strength of the element data becomes "0").

Figure 4B:
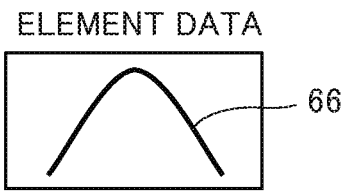
FIGS. 4B and 4D are illustrative diagrams illustrating respective pieces of element data obtained.
Figure 4D:
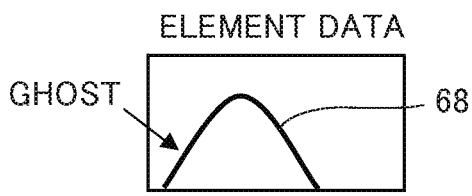
Figure 4A:
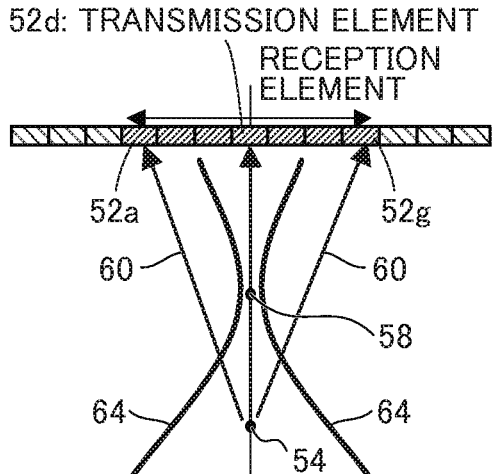
FIGS. 4A and 4C are illustrative diagrams when actual ultrasonic beams are transmitted from an element just above a reflection point of a subject and an element that is not just above the reflection point, respectively.
Figure 4C:
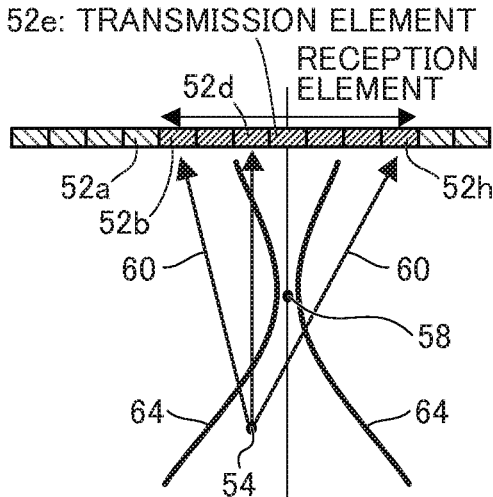

However, an actual transmission beam 64 is wider than the element interval, as illustrated in FIGS. 4A and 4C.

Here, in a case in which the transmission beam 64 is transmitted using the element 52d just above the reflection point 54 as a transmission element as illustrated in FIG. 4A, the focal point 58 is on a straight line that connects the element 52d and the reflection point 54 even when the transmission beam 56 is wide, and thus, the transmission beam 64 is reflected from the reflection point 54 and the ultrasonic echo is generated, similarly to the case illustrated in FIG. 3A. As a result, the ultrasonic echo from the reflection point 54 is received by the reception elements 52a to 52g via the reception path 60 spreading at a predetermined angle, and true element data 66 as illustrated in FIG. 4B is obtained by the reception elements 52a to 52g, similarly to the case illustrated in FIG. 3A.

In contrast, in a case in which similarly to the case illustrated in FIG. 3C, the center of the transmission elements is shifted by one element in an element direction (a right direction in FIG. 4C) relative to the reflection point 54, the transmission beam 64 is transmitted using the element 52e adjacent to the element 52d just above the reflection point 54 as the transmission element, and the ultrasonic echo is received by the reception elements 52b to 52h, as illustrated in FIG. 4C, since the transmission beam 64 is wide, the transmission beam 64 is transmitted to the reflection point 54 even when the reflection point 54 is not on the transmission direction, that is, on a straight line that connects the transmission element 52e with the focal point 58. Therefore, an ultrasonic echo that does not originally exist, that is, a so-called reflection signal of a ghost is generated from the reflection point 54, the reflection signal of the ghost from the reflection point 54 is received by the reception elements 52b to 52h via the reception path 60 spreading at a predetermined angle, and element data 68 of the ghost as illustrated in FIG. 4D is obtained by the reception elements 52b to 52h.

Such element data 68 of the ghost becomes a cause of a decrease in precision of the ultrasound image generated from the element data.

The element data processing unit 22 calculates the delay time corresponding to the element data in the delay time calculation unit 48 and superimposes two or more pieces of element data based on this delay time and an absolute position of the element in the superposition processing unit 50 to thereby generate processed element data that is highly precise element data in which the true element data is emphasized and the element data of the ghost is attenuated.

Here, since the total (propagation distance) of a transmission path of the transmission beam 64 from the transmission element 52e to the reflection point 54 via the focal point 58 and a reception path of the reflection signal of the ghost from the reflection point 54 to the respective reception elements 52b to 52h illustrated in FIG. 4C is longer than the total (propagation distance) of a transmission path of the transmission beam 64 from the transmission element 52d to the reflection point 54 via the focal point 58 and a reception path of the true reflection ultrasonic echo from the reflection point 54 to the respective reception elements 52a to 52g illustrated in FIG. 4A, the element data 68 of the ghost as illustrated in FIG. 4D is delayed relative to the true element data 66 as illustrated in FIG. 4B.

In the delay time calculation unit 48 of the element data processing unit 22 of the present invention, a time difference, that is, a delay time between the true element data and the element data of the ghost is calculated from a geometric arrangement of the transmission element, the focal point of the ultrasonic beam, the reflection point of the subject, and the reception elements. Therefore, information such as the shape of the ultrasound probe 12 (element interval, linear, convex or the like), the sound speed in the inspection target region of the subject, the focal position, the transmission aperture, and the reception aperture is necessary for calculation of the delay time. In the delay time calculation unit 48, these pieces of information input by the operation unit 32 or stored in the storage unit 34 is acquired to calculate the delay time. The delay time can be calculated, for example, from a difference of a propagation time which is calculated from the total length (propagation distance) of the transmission path of the transmission beam from the transmission element to the reflection point via the focal point and the reception path of the true reflection ultrasonic echo or the reflection signal of the ghost from the reflection point to the reception elements, which is calculated from the geometric arrangement of the transmission element, the focal point of the ultrasonic beam, the reflection point of the subject, and the reception elements, and the sound speed thereof.

Figure 5A:
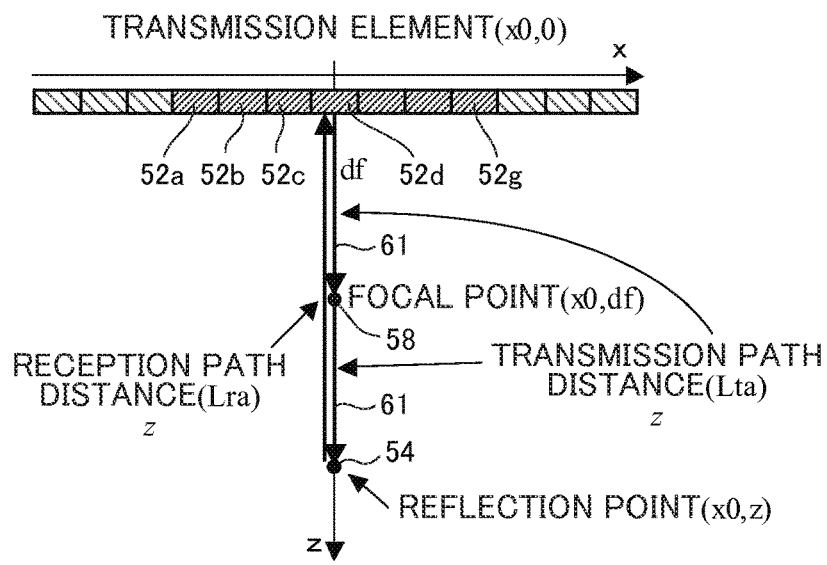
FIGS. 5A and 5B are illustrative diagrams illustrating the distance of a transmission path and a reception path of an ultrasonic beam in the case of a true reflection ultrasonic echo and a reflection signal of a ghost, respectively.
Figure 5B:
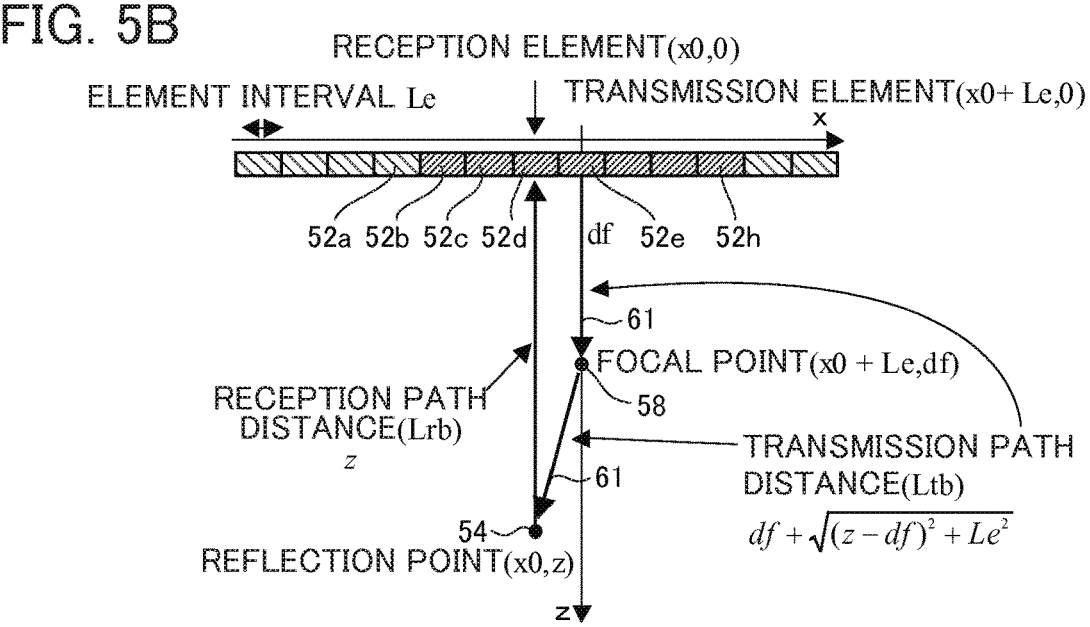

In the present invention, for example, the lengths of the transmission path of the transmission beam and the reception path in the case of the true reflection ultrasonic echo and the reflection signal of the ghost can be obtained, as illustrated in FIGS. 5A and 5B.

In the case of the true reflection ultrasonic echo, as illustrated in FIG. 5A, the transmission element 52$d$ agrees with the reception element 52$d$ (the center of reception elements 52$a$ to 52$g$), and the focal point 58 and the reflection point 54 are arranged just under the element. Accordingly, if it is assumed that a position of the element 52$d$ just above the reflection point 54 is a coordinate (x0, 0) in an two-dimensional xy coordinate, an element interval is Le, a position of the focal point 58 is a coordinate (x0, df), and a position of the reflection point 54 is a coordinate (x0, z), the coordinate of the position of the transmission element 52$d$ is the same as the coordinate (x0, 0) of the element 52$d$ just above the reflection point 54, and a length (transmission path distance) Lta of the transmission path 61 of the transmission beam from the transmission element 52$d$ to the reflection point 54 via the focal point 58 and a length (reception path distance) Lra of the reception path 60 of the true reflection ultrasonic echo from the reflection point 54 to the reception element 52$d$ can be calculated as Lta=Lra=z.

Therefore, the propagation distance Lua of the ultrasound waves in the case of the true reflection ultrasonic echo becomes Lua=Lta+Lra=2z.

In the case of the reflection signal of the ghost, as illustrated in FIG. 5B, the position of the transmission element 52$e$ is shifted by one element in a horizontal direction (x direction: right direction in FIG. 5B) relative to the reflection point 54, and the focal point 58 is arranged just under the transmission element 52$e$ unlike in the case of FIG. 5A. However, the reflection point 54 is arranged directly under the reception element 52$d$. If it is assumed that the position of the reception element 52$d$ just above the reflection point 54 is a coordinate (x0, 0) in a two-dimensional xy coordinate as in the case of FIG. 5A, an element interval is Le, and a position of the reflection point 54 is a coordinate (x0, z), the position of the transmission element 52$e$ is a coordinate (x0+Le, 0) and the position of the focal point 58 is a coordinate (x0+Le, df). Accordingly, a length (transmission path distance) Ltb of the transmission path 61 of the transmission beam from the transmission element 52$e$ to the reflection point 54 via the focal point 58 can be calculated as Ltb=df+$\sqrt{(z-df)^2+Le^2}$, and a length (reception path distance) Lrb of the reception path 60 of the reflection signal of the ghost from the reflection point 54 to the reception element 52$d$ can be calculated as Lrb=z.

Therefore, the propagation distance Lub of the ultrasound waves in the case of the reflection signal of the ghost becomes Lub=Ltb+Lrb=df+$\sqrt{(z-df)^2+Le^2}$+z.

Thus, a value obtained by dividing the propagation distance Lua of the ultrasound waves that is a total of the distance Lta of the transmission path 61 and the distance Lra of the reception path 60 obtained in the geometric arrangement illustrated in FIG. 5A by the sound speed becomes a propagation time of the true reflection ultrasonic echo, and a value obtained by dividing the propagation distance Lub of the ultrasound waves that is a total of the distance Ltb of the transmission path 61 and the distance Lrb of the reception path 60 obtained in the geometric arrangement illustrated in FIG. 5B by the sound speed becomes a propagation time of the reflection signal of the ghost. The delay time is obtained from a difference between the propagation time of the true ultrasonic echo when x coordinate of the reflection point 54 agrees with that of the transmission element 52 (52$d$) and the propagation time of the reflection signal of the ghost when the x coordinates of the reflection point 54 and the transmission element 52 (52$e$) are respectively shifted by one element interval.

While the geometrical model of FIGS. 5A and 5B is a model in which the transmission path 61 passes through the focal point 58, the present invention is not limited thereto and, for example, the transmission path may be a path directly reaching the reflection point 54 without passing through the focal point 58.

Further, while the geometrical model of FIGS. 5A and 5B corresponds to the linear probe, the present invention is not limited thereto and, in other probes, the same geometrical calculation can also be performed using the shape of the probe. For example, in the case of a convex probe, a geometrical model can be set using the radius of the probe and an angle of an element interval, and the calculation can be performed in the same way.

Further, in the case of steering transmission, the delay time of the element data of the true ultrasonic echo and the element data of a neighboring ghost can be calculated based on a positional relationship between the transmission element and the reflection point using a geometrical model (not illustrated) that considers information such as a transmission angle.

Further, the present invention is not limited to a method of calculating the delay time based on the geometrical model, and the delay time may be obtained by a method in which a high brightness reflection point corresponding to each of measurement conditions of the device is measured in advance, from the measurement result thereof, the delay time of the respective measurement conditions are calculated and stored in the device, and the delay time of the same measurement condition as a selected measurement condition is read therefrom.

Figure 5C:
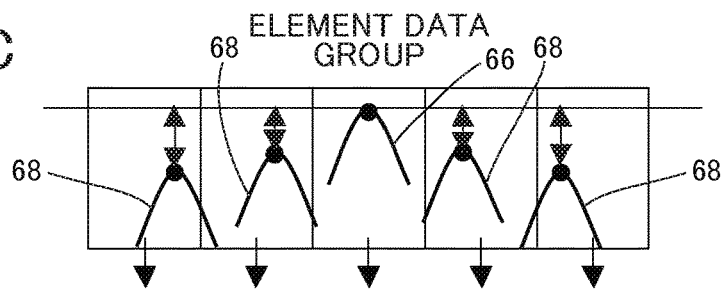
FIGS. 5C and 5D are illustrative diagrams illustrating element data obtained by a plurality of elements and respective delay times thereof.
Figure 5D:
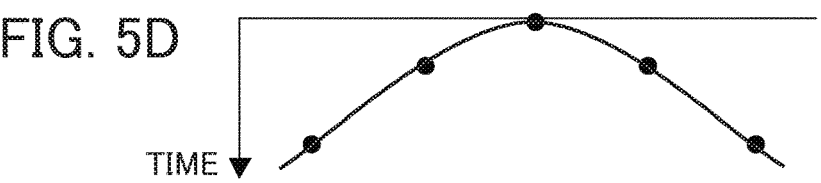

Element data 66 of the true signal at the center and element data 68 of the ghost near the true signal are illustrated in FIG. 5C, and an example of the delay time of the element data 68 of the ghost relative to the element data 66 obtained from the above-described geometrical calculation is illustrated in FIG. 5D. The element data 68 of the ghost signal is symmetrically delayed in terms of time, round the element data 66 of the true signal, as illustrated in FIG. 5D.

The delay time calculated by the delay time calculation unit 48 of the element data processing unit 22 in this way can also be used for delay correction in the phasing addition unit 38.

Although described below in detail, in the present invention, on the element data obtained through the transmission of the ultrasonic beam in which a certain element of interest is the central element (transmission and reception of the element of interest), the element data obtained through the transmission of the ultrasonic beam in which the central element is different and at least a part of the ultrasonic beam is overlapped with the ultrasonic beam for the element of interest, is superimposed, while matching the reception time of the ultrasonic echo and the position of the element, to thereby generate processed element data (second element data) of the element of interest (rebuild the element data of the element of interest).

In FIG. 5, the reflection point 54 indicates a position of a certain sampling point (output position of the element data)

located just under the element of interest (in the same position in an azimuth direction/on a straight line that connects the element of interest with the focal point). In the present invention, a transmission and reception path to and from the sampling point just under the element of interest in the transmission and reception of the element of interest is regarded as a transmission and reception path of true element data, and a transmission and reception path to and from the same sampling point in the transmission and reception of ultrasound wave (transmission and reception of a neighboring element) in which the central element is different is regarded as a transmission and reception path of the ghost. The delay time is calculated from a difference between both transmission and reception paths, and the superposition is performed using this delay time, while matching the time of the element data. In other words, the delay time is calculated on the assumption that the element data obtained through the transmission and reception of the element of interest is true element data and the element data obtained through the transmission and reception in which the central element is different is the element data of the ghost, and the superposition of the element data is performed.

In the present invention, the delay time is calculated in the same way for all samplings points (output positions of all the pieces of element data), and superposition of the element data is performed to generate the processed element data of each element. At this time, it is preferable for a plurality of sampling points to also be set in a depth direction (y direction) on the same line.

Here, actually, even when the position of the sampling point (reflection point) is shifted in the azimuth direction (x direction), the length of the reception path (reception path distance Lrb) does not change. Therefore, for each element of interest, the delay time with respect to the element data due to transmission and reception in which the central element is different may be calculated for each sampling point of the depth direction (y direction).

Further, in this superposition processing, it is not necessary to recognize which element data is the true element data. That is, as described in detail below using FIG. 6, in this superposition process, if the element data of the element of interest is true element data, the element data is emphasized automatically and remains, and if it is element data of the ghost, the element data is canceled. That is, when the element data of the element of interest is true element data, the processing using the delay time matches and the signal is emphasized, and when the element data of the element of interest is element data of the ghost, the processing using the delay time does not match and the signal is canceled.

Then, in the superposition processing unit 50 of the element data processing unit 22 of the present invention, processing of superimposing the element data of the true ultrasonic echo and the element data of the neighboring ghost is performed using the delay time calculated by the delay time calculation unit 48 as described above.

While the number of pieces of element data to be superimposed and information on superposition processing method are necessary in the superposition processing in the superposition processing unit 50, these may be input by the operation unit 32 in advance or may be stored in the storage unit 34.

FIGS. 6A to 6H illustrate a specific example of the superposition processing when the number of pieces of element data is 5 and the number of pieces of superimposed element data is 3, which is performed by the superposition processing unit 50.

FIG. 6A illustrates a state in which five pieces of element data are displayed side by side and an ultrasonic beam is transmitted and a reflection signal is received for each piece of element data. A horizontal axis of each piece of element data indicates the reception element, and a central element at the time of transmission of the ultrasonic beam is at the center in each piece of element data. The vertical axis indicates reception time.

In the central element data among the five pieces of element data, the reflection point is just under the central element of the element data (a central element among the reception elements), that is, a central element at the time of transmission (transmission element), and a reflection signal from the reflection point is received. That is, this reflection signal is a true signal, and the central element data indicates a true signal.

For two pieces of element data on both sides other than the central element data, there is not a reflection point just under the central element at the time of transmission. However, an ultrasonic beam hits the reflection point just under the transmission element of the central element data due to the spread of the transmission ultrasonic beam, and thus, a reflection signal, that is, a ghost is generated and reflected. Since propagation time of ultrasound wave to the reflection point becomes longer as the ghost becomes farther away from the true signal, the reception time of the ghost becomes later than that of the true signal. Further, the reception element by which the reflection signal from the reflection point is first received is an element just above the reflection point. However, since the center of the horizontal axis of the element data is a central element at the time of transmission of the ultrasonic beam, and the transmission is performed while shifting this central element by one element for each piece of element data, an absolute position of the element is shifted by one element in each piece of element data. That is, in the central element data, the reception element by which the reflection signal from the reflection point is first received is the central element, whereas in the two pieces of element data on both sides of the central element data, it is shifted by one element relative to the central element data. That is, in the element data on the right side, it is shifted by one element to the left, and in the element data on the left side, it is shifted by one element to the right. Further, in the two pieces of element data at both ends, the reception element by which the reflection signal from the reflection point is first received is shifted by two elements relative to the central element data. That is, in the element data at a right end, it is shifted by two elements to the left, and in the element data at a left end, it is shifted by two elements to the right. Thus, the reception time of the ghost signal is not only delayed relative to the true signal, but also shifted relative to the direction of the reception elements.

In FIG. 6B, an example of the delay of the reception time relative to the central element data among five pieces of element data illustrated in FIG. 6A is illustrated.

When the central element data is the element data of the element of interest, the superposition processing unit 50 performs delay time correction by the number of pieces of element data to be superimposed including the element data of the element of interest as the center (in the illustrated example, three pieces of element data) using the delay time illustrated in FIG. 6B, and horizontally shifts each piece of element data by the difference in element position between the element data to be shifted and the element data of the element of interest (difference between the positions of the central element) (in the illustrated example, by one element toward both sides), that is, performs phase matching, and then, the superposition processing unit 50 superimposes pieces of unprocessed element data corresponding to the pieces of element data to be superimposed (in the illustrated example, three pieces of element data) to obtain one piece of processed element data of the element of interest.

The processed element data of the element data of the element of interest obtained in this way is illustrated in FIG. 6C.

Element data of the element of interest illustrated in FIG. 6A is the element data of the true signal. Accordingly, when the delay time correction and the horizontal shift are performed on the unprocessed element data of adjacent element data on both sides of the element data of the element of interest for phasing, unprocessed element data of the adjacent element data and unprocessed element data of the element of interest are phased and overlapped each other in a high brightness position, as illustrated in FIG. 6C. Therefore, for example, when these pieces of element data are added together, obtained element data has a great value (high brightness value) and, for example, even when an average value is calculated, an emphasized value (high brightness value) is obtained.

In contrast, FIG. 6D illustrates the same element data as that in FIG. 6A, but illustrates an example of a case in which adjacent element data on the left side of the central element data, that is, a ghost, is assumed to be element data of the element of interest.

FIG. 6E is the same as FIG. 6B, and illustrates an example of the delay of the reception time relative to the central element data among the five pieces of element data illustrated in FIG. 6A. That is, since FIGS. 6A and 6D illustrate the same element data, the delay of the reception time relative to the central element data among the five pieces of element data illustrated in FIG. 6D is equivalent.

In the superposition processing unit 50, the delay time correction is performed by the number of pieces of element data to be superimposed including the element data of the element of interest as the center (in the illustrated example, three pieces of element data) using the delay time illustrated in FIG. 6E (that is, the same as FIG. 6B), each piece of element data is horizontally shifted by the difference in element position between the element data to be shifted and the element data of the element of interest (difference between the positions of the central element) (in the illustrated example, by one element toward both sides), and then, pieces of unprocessed element data corresponding to the pieces of element data to be superimposed (in the illustrated example, three pieces of element data) are superimposed to obtain one piece of processed element data of the element of interest.

The processed element data of the element data of the element of interest obtained in this way is illustrated in FIG. 6F.

The element data of the element of interest illustrated in FIG. 6D is element data of the ghost. Accordingly, even when the delay time correction and the horizontal shift are performed on the unprocessed element data of the adjacent element data on both sides of the element data of the element of interest for phasing, the unprocessed element data of the adjacent element data and the unprocessed element data of the element of interest are not phased and overlapped each other as illustrated in FIG. 6F. Therefore, for example, when the three pieces of element data are added together, the pieces of element data are not phased, and thus, signals of which the phase are inverted, or the like are cancelled each other. Accordingly, an adding value is not great, and for example, when an average value is calculated, only a small value is obtained.

For the other element data, a superposition state of adjacent three pieces of element data with respect to each of the five pieces of element data in the illustrated example, which has been subjected to the above delay time correction and the above horizontal shift as element data of the element of interest, is illustrated in FIG. 6G. A result of performing the superposition processing, such as addition processing or averaging processing, on the element data, is illustrated in FIG. 6H.

As illustrated in FIG. 6H, in the element data of the element of interest when the coordinates of the transmission element and the reflection point match as illustrated in FIG. 6A, the element data of the true signal is obtained as processed element data having a high brightness value. In contrast, in four pieces of element data, including two pieces of element data on both sides, pieces of element data of the ghost that are not phased are added together or averaged, and accordingly, the pieces of element data are cancelled each other. Thus, a value of the processed element data of the ghost becomes smaller than a value of the processed element data having a high brightness value that is the element data of the true signal. Therefore, it is possible to reduce the influence of the element data of the ghost on the element data of the true signal or to cause the influence to be small such that the influence is negligible.

Therefore, influence of the ghost can be similarly eliminated by performing the phasing addition or the detection processing on the processed element data to generate the reception data and generate the ultrasound image. That is, the ultrasound image can be generated using element data that is equivalent to element data in which a focal point is formed at all points of the sound ray. Accordingly, it is possible to generate a high-resolution ultrasound image having excellent sharpness and high brightness.

In the following description, the generation of the processed element data is also referred to as multiline processing.

In the present invention, the central element is a central element in an azimuth direction when a numerical aperture of transmission (the number of elements that perform transmission of ultrasonic wave) is an odd number.

On the other hand, when the numerical aperture is an even number, any one of central elements in the azimuth direction is the central element, or it is assumed that an element exists at the center in the azimuth direction, and the hypothetical element is the central element. That is, when the numerical aperture is the even number, the calculation may be performed on the assumption that a focal point is on a line at the center of the apertures.

Further, in a superposition processing method in the superposition processing unit 50, as well as addition, an average value or a median value may be calculated or a coefficient may be multiplied (weighted) and then addition may be performed. Further, calculation of the average value or the median value is considered to be equivalent to the application of an averaging filter or a median filter at an element data level, but an inverse filter performed in normal image processing may be applied in place of the averaging filter or the median filter. Alternatively, pieces of element data to be superimposed may be compared. When the pieces of element data are similar, a maximum value may be taken. When the pieces of element data are not similar, an average value may be taken. When there is a deviation of a distribution, a middle value may be taken. The present invention is not limited to these, and superposition processing may be changed based on the feature amount of each piece of element data to be superimposed.

Further, the number of pieces of element data to be superimposed on the element data of the element of interest is not limited to 2 in the illustrated example, and the number thereof may be 1 or may be 3 or more. That is, the number of pieces of element data to be superimposed on the element data of the element of interest may be appropriately set according to the required processing speed (for example, a frame rate) or image quality.

It is preferable for the number of pieces of element data to be superimposed to be set based on the degree of the beam width of the ultrasonic beam. Therefore, when the beam width is changed depending on the depth, the number of pieces of element data to be superimposed may be changed depending on the depth. Further, since the beam width depends on the transmission numerical aperture, the number of pieces of element data to be superimposed may be changed depending on the transmission numerical aperture. Alternatively, the number of pieces of element data to be superimposed may be changed based on a feature amount such as a brightness value of the image, or may be changed based on a result of performing waveform analysis of the element data and evaluating a correlation or coherence between the pieces of element data. Otherwise, the optimal number of pieces of element data to be superimposed may be selected from a plurality of images created by changing the number of pieces of element data to be superimposed.

Further, the present invention is not limited to changing the number of pieces of element data to be superimposed depending on the depth. The depth of the transmission focal point, the transmission numerical aperture, or the like may be changed depending on a spatial depth of a superposition position (sampling point), and multiline processing may be performed using first element data obtained by performing transmission of the ultrasonic beam under the changed transmission condition.

For example, multiline processing is performed using the first element data obtained by setting a transmission focal point in a position depending on the depth of the sampling point so that the sampling point and the focal point become a predetermined distance from one another. Accordingly, precision of the multiline processing can be uniform regardless of the depth of the sampling point. Further, it is more preferable to set the position of the transmission focal point and the numerical aperture depending on the depth of the sampling point so that the F value is constant regardless of the depth of the transmission focal point (see FIGS. 22A and 22B). Accordingly, the precision of the multiline processing can be more uniform regardless of the depth of the sampling point.

Further, ultrasonic beams forming transmission focal points of a different depth on the same transmission line may be transmitted to each transmission line, a plurality of pieces of first element data corresponding to the same transmission line may be acquired, and the element data processing unit 22 may perform multiline processing using the first element data of the same focal point depth in different transmission lines for each depth of the transmission focal point. In this case, the calculation of the delay time may be performed based on each depth of the transmission focal point (reception time of element data).

While in the above-described multiline processing, the processed element data of the element data of the element of interest is generated by superimposing the pieces of element data obtained through the transmission of the plurality of ultrasonic beams in which the central elements are different and the transmission directions of the ultrasonic beams are parallel (the angles are the same), the present invention is not limited thereto.

For example, the processed element data may be generated by superimposing the pieces of element data obtained through the transmission of the plurality of ultrasonic beams in which the central elements are the same and the transmission directions (angles) are different. In this case, selection of a ultrasonic beam by which the element data to generate the processed data is obtained (that is, selection of a direction of the sound ray by which the processed data is generated) may be set as default depending on, for example, a diagnosis portion, a type of the probe, or the like, or may be performed by an operator.

Further, the processed element data may be generated using both element data obtained through transmission of the parallel ultrasonic beams in which the central elements are different and element data obtained through transmission of ultrasonic beams in which the central elements are the same and the transmission directions are different.

As a result of the superposition, as described above, signals are phased in the element data of the true signal, whereas signals are not phased in the ghost, and thus, signals of various phases are cancelled each other and weakened as a result of the superposition processing, such as addition. Accordingly, the true signal remains as element data having a valid value such as, for example, element data having high brightness, and the ghost signal can be obtained as element data having an attenuated value such as, for example, element data having low brightness.

An operation and action of the ultrasonic inspection apparatus of the present invention, and a method of creating an ultrasound image will be described.

Figure 7:
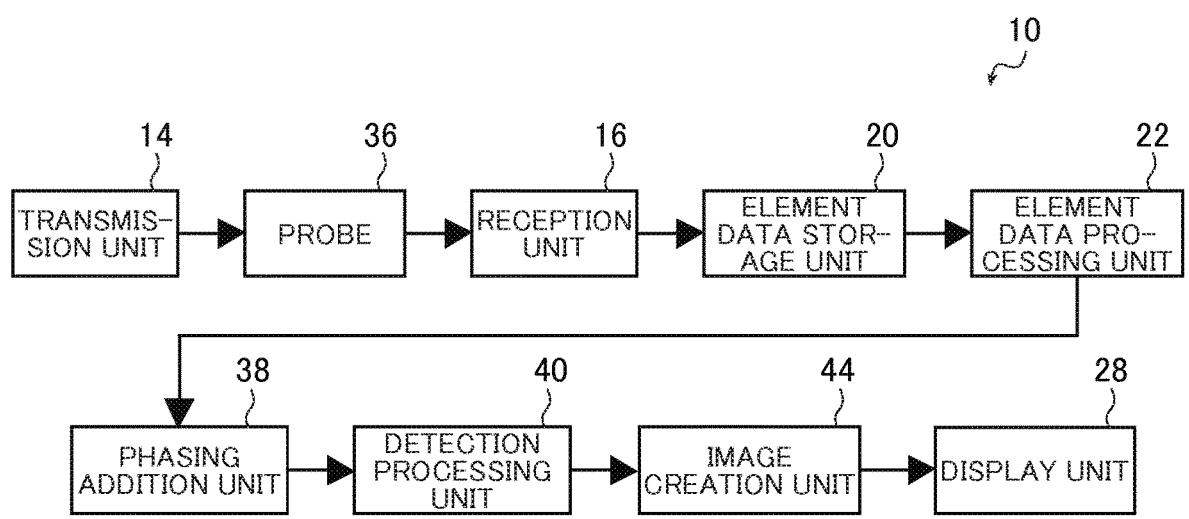
FIG. 7 is a block diagram illustrating, along a process flow, primary units of the ultrasonic inspection apparatus of Embodiment 1 of the present invention illustrated in FIG. 1.

FIG. 7 is a block diagram illustrating, along a process flow, primary units of an ultrasonic inspection apparatus of Embodiment 1 illustrated in FIG. 1.

When an operator causes the ultrasound probe 12 to come in contact with a surface of a subject and starts measurement, as illustrated in FIG. 1, an ultrasonic beam is transmitted from the probe 36 according to a driving signal supplied from the transmission unit 14, and an ultrasonic echo from the subject is received by the probe 36 and an analog element signal is output therefrom as a reception signal, as illustrated in FIG. 7.

The reception unit 16 amplifies the analog element signal and supplies the amplified analog element signal to the A/D conversion unit 18. The A/D conversion unit 18 converts the amplified analog element signal into digital element data, and supplies the digital element data to the element data storage unit 20 to cause the element data storage unit 20 to store and hold the digital element data.

The delay time calculation unit 48 (FIG. 2) of the element data processing unit 22 calculates a delay time (for example, FIGS. 6B and 6E which are the same) of unprocessed element data of the signal of the neighboring ghost relative to the unprocessed element data of the true signal based on, for example, the geometric arrangement of the transmission element, the focal point, the reflection point, and the reception element, and the sound speed of the inspection target region of the subject that is input and set in advance (for example, calculates the delay time using the geometrical model illustrated in FIG. 5).

Then, the element data processing unit 22 reads unprocessed element data from the element data storage unit 20, and sets the element data to be processed as element data of the element of interest, and in the superposition processing unit 50 (FIG. 2), phases and superimposes the element data of the element of interest and neighboring unprocessed element data using the delay time calculated by the delay time calculation unit 48 to obtain the processed element data. Accordingly, if the element data is unprocessed element data including the true signal, emphasized processed element data is obtained, and if the element data is unprocessed element data of the ghost, the attenuated processed element data is obtained.

The element data processing unit 22 supplies the processed element data obtained in this way to the phasing addition unit 38 of the image generation unit 24.

The phasing addition unit 38 of the image generation unit 24 performs the reception focus processing on the element data to generate reception data (sound ray signal), and supplies the reception data to the detection processing unit 40. The detection processing unit 40 processes the sound ray signal to generate a B-mode image signal. The DSC 42 raster-converts the B-mode image signal, and then, the image creation unit 44 performs image processing on the raster-converted B-mode image signal to create an ultrasound image. The created ultrasound image is stored in the image memory 46, and displayed on the display unit 28 by the display controller 26.

Thus, since the ultrasonic inspection apparatus 10 of Embodiment 1 of the present invention creates an ultrasound image using the processed element data in which the ghost signal is attenuated and the true signal is emphasized in the element data processing unit 22, it is possible to obtain a sharp ultrasound image having a high SN ratio and an optimal spatial resolution with high resolution that does not depend on the width of the transmission beam, without using a dedicated ultrasound probe for generating a wide transmission ultrasonic beam and at a frame rate that is not different from the conventional frame rate.

The ultrasonic inspection apparatus of Embodiment 1 of the present invention is basically configured as described above.

In the ultrasonic inspection apparatus 10 of Embodiment 1 of the present invention, the sound speed within the inspection target, that is, the inspection target region of the subject which is necessary when the delay time is calculated by the delay time calculation unit 48 of the element data processing unit 22 and when delay time used in the phasing addition unit 38 is calculated is given. However, the present invention is not limited thereto, and when the sound speed within the inspection target is not known, an optimal sound speed may be set in the ultrasonic inspection apparatus as described below.

Embodiment 2

Next, an ultrasonic inspection apparatus of Embodiment 2 of the present invention will be described based on FIGS. 8A and 8B.

Each of FIGS. 8A and 8B is a block diagram conceptually illustrating, along a process flow, an example of primary units of an ultrasonic inspection apparatus of Embodiment 2 of the present invention.

Since ultrasonic inspection apparatuses 70a and 70b illustrated in FIGS. 8A and 8B have the same configuration as the ultrasonic inspection apparatus 10 illustrated in FIGS. 1 and 7 except that determination units 72a and 72b and a sound speed changing unit 74 are included, the same components are denoted with the same reference signs and detailed description thereof will be omitted.

First, the ultrasonic inspection apparatus 70a illustrated in FIG. 8A will be described. FIG. 8A illustrates, along a process flow, the primary units of the ultrasonic inspection apparatus 70a, as in FIG. 7.

The ultrasonic inspection apparatus 70a includes the transmission unit 14, the probe 36, the reception unit 16, the element data storage unit 20, the element data processing unit 22, the phasing addition unit 38, the detection processing unit 40, the image creation unit 44, a determination unit 72a, a sound speed changing unit 74, and the display unit 28, as illustrated in FIG. 8A.

Here, since the processing in the probe 36, the transmission unit 14, the reception unit 16, and the element data storage unit 20 and the first time processing in the element data processing unit 22, the phasing addition unit 38, the detection processing unit 40 and the image creation unit 44 are performed as in the ultrasonic inspection apparatus 10 illustrated in FIGS. 1 and 7, description thereof will be omitted.

In the first time processing, the element data processing unit 22 performs processing on the element data using an initial value of the sound speed set in advance, and then, sends the processed element data to the phasing addition unit 38. The phasing addition unit 38 performs reception focus processing, that is, phasing addition using an appropriate sound speed value such as a sound speed value close to a living body to generate a sound ray signal (reception data). The detection processing unit 40 performs detection processing on the generated sound ray signal to generate a B-mode image signal. The image creation unit 44 performs image processing on the generated B-mode image signal to generate an ultrasound image.

The determination unit 72a is provided between the image creation unit 44 and the display unit 28, and performs a determination based on the ultrasound image created by the image creation unit 44, for example, based on the image quality index such as a brightness value or sharpness of the ultrasound image, or sharpness of the brightness value, or a degree of convergence of the sound speed, using the created ultrasound image. The determination unit 72a, for example, determines "suitable" or OK when the image quality index such as the brightness value or the sharpness of the ultrasound image, or the sharpness of the brightness value is higher than a predetermined value and preferably, is highest or when the sound speed is converged in a predetermined range, and otherwise determines "unsuitable" or NG.

When the determination unit 72a determines OK, the ultrasound image created by the image creation unit 44 is sent to the display unit 28 and displayed on the display screen.

On the other hand, when the determination unit 72a determines NG, the process proceeds to the sound speed changing unit 74.

The sound speed changing unit 74 sets the optimal sound speed when the sound speed in the inspection target necessary for delay time calculation in the delay time calculation unit 48 of the element data processing unit 22 is not known. The sound speed changing unit 74 initially changes an initial value of the sound speed set in advance into a new sound speed value and sets the new sound speed value, and from the second time, changes a previously set sound speed value into a new sound speed value and sets the new sound speed value.

Here, while any method may be used to change the sound speed value as long as the method is capable of obtaining an optimal sound speed value to which the determination unit 72a gives the determination of OK, it is preferable to increase or decrease the sound speed at predetermined intervals from the initial value of the sound speed. The change of the sound speed value may be sequentially performed at predetermined speed intervals over a predetermined sound speed range. For example, when a living body such as a human body is a target, the sound speed can be sequentially changed from 1400 m/s to 1700 m/s in a predetermined step of 1 m/s to 50 m/s, such as a step of 10 m/s.

When the sound speed changing unit 74 changes the sound speed into a new sound speed value, the process returns from the sound speed changing unit 74 to the element data processing unit 22. In the second time and subsequent processing, the delay time calculation unit 48 of the element data processing unit 22 calculates the delay time again using the new sound speed value. Thereafter, the superposition processing unit 50 performs the superposition processing on two or more pieces of unprocessed element data using the delay time calculated by the delay time calculation unit 48 to obtain processed element data.

After the processed element data is obtained in the element data processing unit 22, the phasing addition unit 38 performs reception focus processing on the processed element data obtained in the element data processing unit 22 based on the new sound speed value changed by the sound speed changing unit 74 to generate a sound ray signal. As in the first time processing, the detection processing unit 40 performs the detection processing and the image creation unit 44 performs the image processing to create an ultrasound image. The determination unit 72*a* performs the determination with respect to the ultrasound image.

Here, if the determination of the determination unit 72*a* is OK, the ultrasound image created by the image creation unit 44 is displayed on the display unit 28.

On the other hand, if the determination of the determination unit 72*a* is NG, the changing into a new sound speed value in the sound speed changing unit 74, the calculation of the delay time in the delay time calculation unit 48 of the element data processing unit 22 using the new sound speed value, the generation of the processed element data in the superposition unit 50, the generation of the sound ray signal based on the new sound speed value in the phasing addition unit 38, the detection processing in the detection processing unit 40, and the creation of the ultrasound image in the image creation unit 44 are repeated until the determination of the determination unit 72*a* is OK, that is, until an optimal sound speed is set.

Even when the changing into the new sound speed value in the sound speed changing unit 74 is all performed in a predetermined sound speed range, for example, even when the changing is performed at predetermined intervals in the predetermined entire sound speed range, if the determination of the determination unit 72*a* is not OK, for example, a sound speed value when a determination closest to a determination criteria is obtained may be adopted as the optimal sound speed.

A method of changing the sound speed value and a method of setting the sound speed in the sound speed changing unit 74 is not particularly limited in the present invention. As described above, the changing of the sound speed value may be sequentially performed at predetermined intervals in a predetermined sound speed range, and the determination unit 72*a* may perform the determination each time the above-described processing is performed using the changed sound speed value, or the changing of the sound speed value may be cyclopedically performed at predetermined intervals in the predetermined entire sound speed range, the above-described processing may be performed using all sound speed values in the predetermined entire sound speed range, and then, the determination unit 72*a* may perform the determination. Alternatively, the changing of the sound speed value and the setting of the optimal sound speed may be exploratorily performed. For example, when the changing and the setting are exploratorily performed, an initial value of the set sound speed starts from a value close to the living body as far as possible. For example, if the image quality index such as the sharpness of the image increases as a result of the determination when the sound speed value is changed toward a positive side, the sound speed value may be further changed, and this operation may be repeated until the image quality index such as the sharpness of the image decreases. Or, when the sound speed value is first changed toward a negative side, if the image quality index such as the sharpness of the image decreases as a result of the determination, the sound speed value may be changed toward the positive side. In this way, a next sound speed value may be appropriately changed through a comparison with a previous sound speed value so that the sound speed value is converged on a predetermined sound speed value, and the converged sound speed value may be set as an optimal sound speed.

When the changing of the sound speed value and the setting of the optimal sound speed in the sound speed changing unit 74 are performed, the region in which the sound speed value is set is not particularly limited. The same sound speed value may be set for the entire subject or the entire inspection target area, the subject or the inspection target region may be divided into small areas and the sound speed value may be set for each small region, or the sound speed value may be set point by point in units of pixels. Further, the sound speed value may be set for a region of interest of the subject or the inspection target region, and the sound speed value set in the region of interest may be used as an optimal sound speed.

Even in these cases, since the sound speed value in the position of the reflection point to be calculated may be adopted as the sound speed value used for calculation of the delay time, it is understood that there is no difference between calculation methods.

In the ultrasonic inspection apparatus 70*a* illustrated in FIG. 8A, the determination unit 72*a* is provided between the image creation unit 44 and the display unit 28, but the present invention is not limited thereto, and the determination unit 72*b* may be provided between the phasing addition unit 38 and the detection processing 40, as in the ultrasonic inspection apparatus 70*b* illustrated in FIG. 8B.

In the ultrasonic inspection apparatus 70*b* illustrated in FIG. 8B, since the processing in the probe 36, the transmission unit 14, the reception unit 16, and the element data storage unit 20, the processing in the detection processing unit 40, the image creation unit 44, and the display unit 28, and the first time processing in the element data processing unit 22 and the phasing addition unit 38 are performed as in the ultrasonic inspection apparatus 70*a* illustrated in FIG. 8A, description thereof will be omitted.

The determination unit 72*b* is provided between the phasing addition unit 38 and the detection processing unit 40. The determination unit 72*b* performs the determination based on the sound ray signal generated by the phasing addition unit 38 performing the reception focal point processing, for example, based on the image quality index such as a brightness value or sharpness of the image, or the sharpness of the brightness value obtained using the sound ray signal, or sharpness of the brightness value, or a degree of convergence of the sound speed. Similarly to the determination unit 72a, the determination unit 72b, for example, determines OK when the image quality index such as the brightness value or the sharpness of the image, or the sharpness of the brightness value is higher than a predetermined value and preferably, is highest or when the sound speed is converged in a predetermined range, and determines NG when the image quality index such as the brightness value or the sharpness do not reach the predetermined value or the highest value, or when the sound speed is not converged in the predetermined range.

When the determination unit 72b determines OK, the sound ray signal generated in the phasing addition unit 38 is subjected to the detection processing in the detection processing unit 40, and then, the creation of the ultrasound image in the image creation unit 44, and the display of the ultrasound image in the display unit 28 are performed.

On the other hand, when the determination unit 72b determines NG, the process proceeds to the second time and subsequent processing. The sound speed changing unit 74 changes the sound speed value into a new sound speed value, and the process proceeds to the element data processing unit 22. The delay time calculation unit 48 of the element data processing unit 22 calculates the delay time again using the new sound speed value changed by the sound speed changing unit 74. Thereafter, the superposition processing unit 50 performs the superposition processing on two or more pieces of unprocessed element data using the delay time calculated using the new sound speed value to obtain processed element data.

After the processed element data is obtained in the element data processing unit 22, the phasing addition unit 38 performs reception focus processing on the processed element data obtained by the element data processing unit 22 based on the new sound speed value changed by the sound speed changing unit 74 to generate a sound ray signal (reception data), and the determination unit 72b performs the determination based on the sound ray signal generated by the phasing addition unit 38, as in the first time processing.

Thus, in the second time and subsequent processing, the respective processing in the sound speed changing unit 74, the element data processing unit 22, the phasing addition unit 38 and the determination unit 72b are repeated until the determination of the determination unit 72b is OK. After the determination unit 72b determines OK, the ultrasound image is displayed on the display unit 28 through the respective processing in the detection processing unit 40 and the image creation unit 44.

Thus, in the ultrasonic inspection apparatuses 70a and 70b of Embodiment 2 of the present invention, an ultrasound image is created using the processed element data in which the ghost signal is attenuated and the true signal is emphasized in the element data processing unit 22. Accordingly, it is possible to obtain a sharp ultrasound image having a high SN ratio and an optimal spatial resolution with high resolution that does not depend on the width of the transmission beam, without using a dedicated ultrasound probe for generating a wide transmission ultrasonic beam and at a frame rate that is not different from the conventional frame rate.

The ultrasonic inspection apparatuses of Embodiment 2 of the present invention are basically configured as described above.

In the ultrasonic inspection apparatuses 70a and 70b of Embodiment 2 of the present invention, when the determination result in the determination units 72a and 72b is OK, an ultrasound image created by the image creation unit 44 is directly displayed on the display unit 28 (70a), or an ultrasound image created through the detection processing in the detection processing unit 40 and the image processing in the image creation unit 44 is displayed on the display unit 28 (70b). However, the present invention is not limited thereto, and after the determination result of the determination unit is OK, an optimal sound speed of the reception side may be obtained, and the reception focus processing (phasing addition processing), the detection processing, and the image processing may be performed using the obtained optimal sound speed to create and display an ultrasound image.

Embodiment 3

Next, an ultrasonic inspection apparatus of Embodiment 3 of the present invention will be described based on FIGS. 9 to 12.

Figure 9:
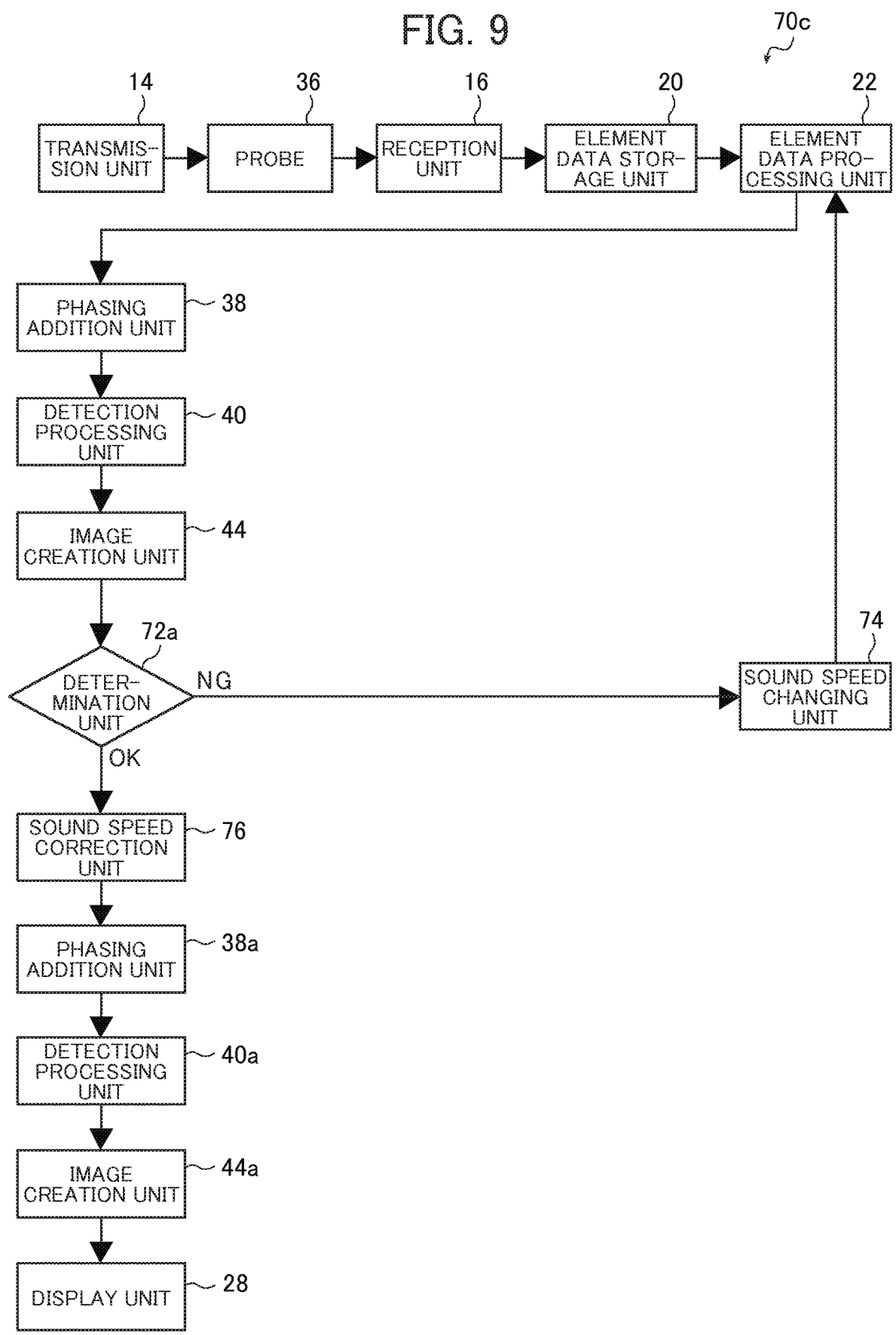
FIG. 9 is a block diagram conceptually illustrating, along a process flow, an example of primary units of the ultrasonic inspection apparatus of Embodiment 3 of the present invention.
Figure 10A:
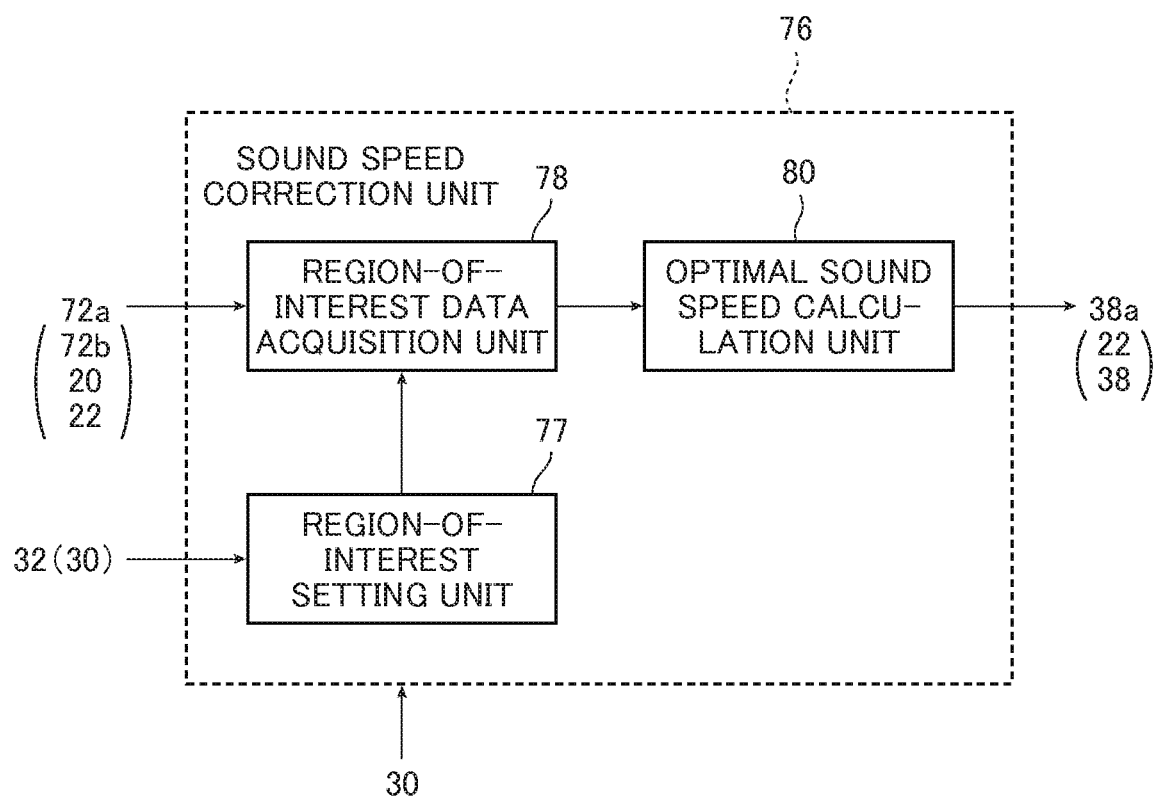
FIG. 10A is a block diagram conceptually illustrating an example of a configuration of a sound speed correction unit of the ultrasonic inspection apparatus illustrated in FIG. 9.
Figure 10B:
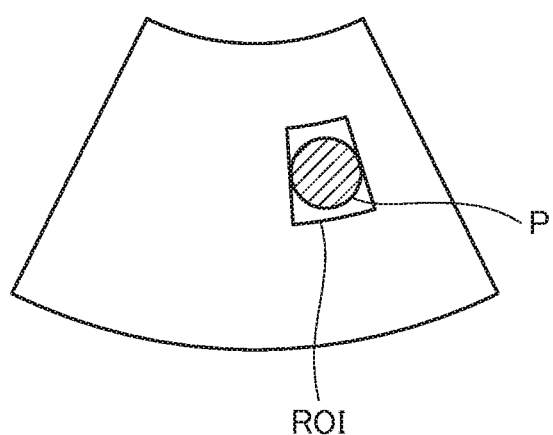
FIG. 10B is a diagram schematically illustrating an example of an ultrasound image in which a region of interest is set in a region-of-interest setting unit of the sound speed correction unit illustrated in FIG. 10A.
Figure 11:
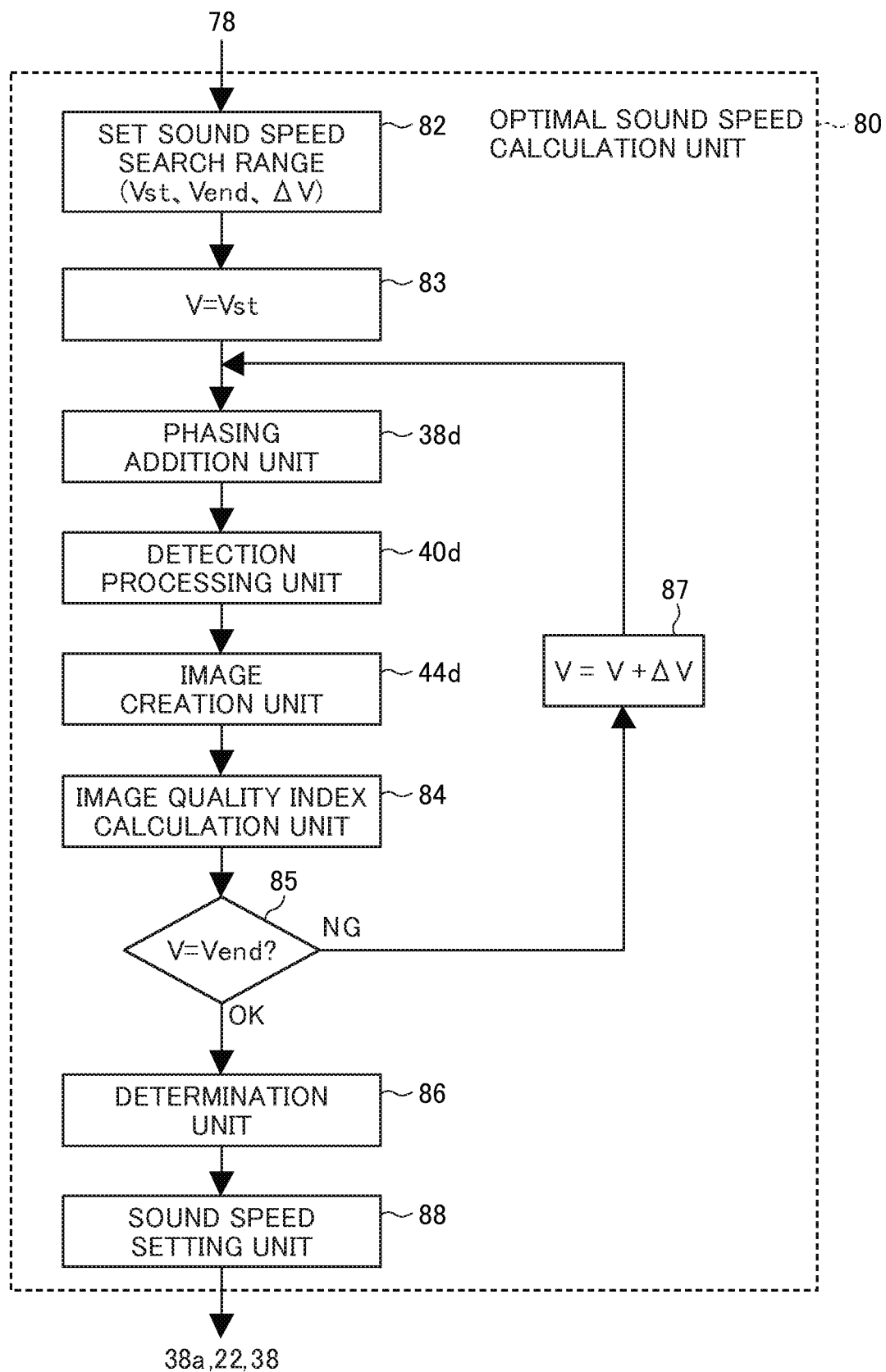
FIG. 11 is a block diagram illustrating, along a process flow, details of an example of an optimal sound speed calculation unit of the sound speed correction unit illustrated in FIG. 10A.
Figure 12:
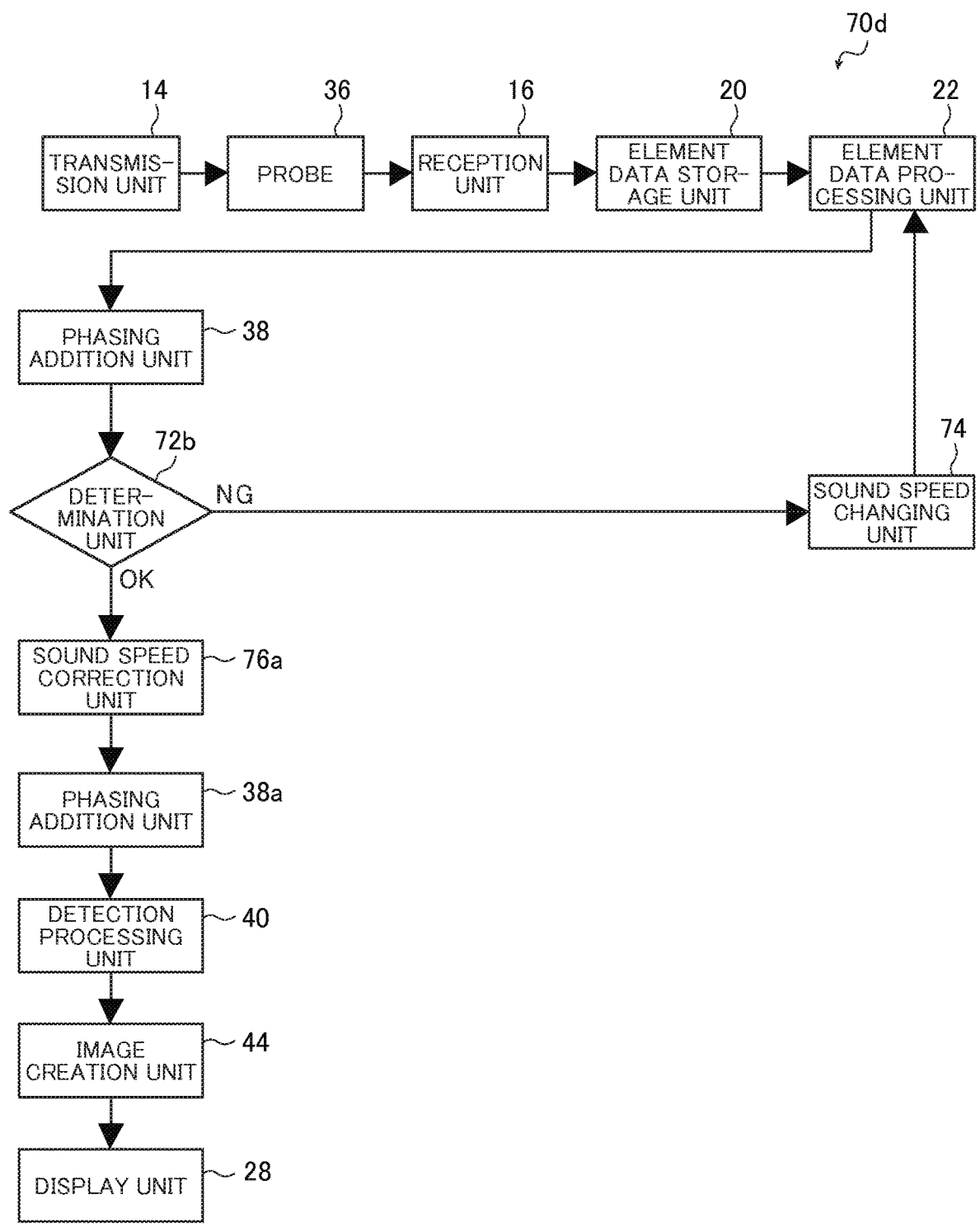
FIG. 12 is a block diagram conceptually illustrating, along a process flow, another example of primary units of an ultrasonic inspection apparatus of Embodiment 3 of the present invention.

Each of FIG. 9 and FIG. 12 is a block diagram conceptually illustrating, along a process flow, an example of primary units of the ultrasonic inspection apparatus of Embodiment 3 of the present invention. FIG. 10A is a block diagram conceptually illustrating an example of a configuration of a sound speed correction unit of the ultrasonic inspection apparatus illustrated in FIG. 9. FIG. 10B is a diagram schematically illustrating an example of an ultrasound image in which a region of interest is set in a region-of-interest setting unit of the sound speed correction unit illustrated in FIG. 10A. FIG. 11 is a block diagram illustrating, along a process flow, details of an example of an optimal sound speed calculation unit of the sound speed correction unit illustrated in FIG. 10A.

The ultrasonic inspection apparatuses 70c and 70d illustrated in FIGS. 9 and 12 respectively have exactly the same configuration as the ultrasonic inspection apparatuses 70a and 70b illustrated in FIGS. 8A and 8B except that sound speed correction units 76 and 76a are respectively provided in subsequent stages of the determination units 72a and 72b, and the reception focus processing (phasing addition processing), the detection processing, the image processing, and the displaying of the ultrasound image are performed using an optimal sound speed set by the sound speed correction units 76 and 76a. Accordingly, the same components are denoted with the same reference signs and detailed description thereof will be omitted.

First, an ultrasonic inspection apparatus 70c illustrated in FIG. 9 will be described. FIG. 9 is a block diagram illustrating, along a process flow, the primary units of the ultrasonic inspection apparatus 70c, as in FIG. 8A.

The ultrasonic inspection apparatus 70c includes the transmission unit 14, the probe 36, the reception unit 16, the element data storage unit 20, the element data processing unit 22, the phasing addition unit 38, the detection processing unit 40, the image creation unit 44, the determination unit 72a, the sound speed changing unit 74, a sound speed correction unit 76, a phasing addition unit 38a, a detection processing unit 40a, an image creation unit 44a, and the display unit 28, as illustrated in FIG. 9.

Here, since the processing in the probe 36, the transmission unit 14, the reception unit 16 and the element data storage unit 20, and the processing in the element data processing unit 22, the phasing addition unit 38, the detection processing unit 40, the image creation unit 44, the determination unit 72a, and the sound speed changing unit 74 until the determination unit 72a determinates OK are performed as in the ultrasonic inspection apparatus 70a illustrated in FIG. 8A, description thereof will be omitted.

The sound speed correction unit 76 is provided between the determination unit 72a and the phasing addition unit 38a, and is intended to obtain an optimal sound speed of the reception side, that is, a sound speed optimal for the inspection target region of the subject, and accordingly, a sound speed optimal for ultrasound image thereof, to be used in the phasing addition unit 38a. For example, the sound speed correction unit 76 changes the set sound speed v over a predetermined entire sound speed range, which is estimated as a sound speed range in the inspection target region, at predetermined sound speed intervals, and cyclopedically obtains an optimal sound speed based on an image quality index such as a brightness value or a sharpness of the image in the inspection target region, or a degree of convergence of the sound speed. Specifically, for example, when a living body such as a human body is a target, the set sound speed v is changed from 1400 m/s to 1650 m/s or 1700 m/s with a predetermined increment (step) of 1 m/s to 50 m/s, such as an increment of 10 m/s.

For example, a sound speed correction method disclosed in JP 2011-92686 A may be used as a sound speed correction method in the sound speed correction unit 76. In the sound speed correction method disclosed in this publication, it is necessary to form transmission focal point in each region of interest. However, in the present invention, since element data enabling the transmission focal point to be artificially formed even in any depth is obtained through the superposition processing of the superposition processing unit in the element data processing unit 22, it is not necessary to set the transmission focal point for each region of interest. However, even in the present invention, it is understood that the transmission focal point may be set for each region of interest, as in the sound speed correction method disclosed in the publication.

For example, as will be described below in detail, the sound speed correction unit 76 changes the set sound speed v in the inspection target region, a phasing addition unit 38d of an optimal sound speed calculation unit 80 performs reception focus processing (phasing addition processing) using the element data such as the unprocessed element data supplied without being processed from the element data storage unit 20 directly or via the element data processing unit 22 or the processed element data supplied from the element data processing unit 22 based on the setting speed v in each setting speed v to generate a sound ray signal, and an image creation unit 44d forms an ultrasound image from this sound ray signal, and calculates an image quality index such as a brightness value or sharpness of the image in the inspection target region in each set sound speed v, as illustrated in FIG. 11.

A comparison determination unit 86 compares the image quality indexes such as the brightness values or the sharpness of the image in the respective set sound speeds v, and determines, for example, the set sound speed v at which the obtained value of image quality index such as the brightness value or the sharpness is greatest. A sound speed setting unit 88 sets the determined set sound speed v as an optimal sound speed value.

That is, the sound speed correction unit 76 may perform the changing of the sound speed value and the setting of the optimal sound speed cyclopedically or exploratorily, similar to the sound speed changing unit 74.

When the sound speed correction unit 76 performs the changing of the sound speed value and the setting of the optimal sound speed, the region in which the sound speed value is set is not particularly limited. The same sound speed value may be set for the entire subject or the entire inspection target area, the subject or the inspection target region may be divided into small areas and the sound speed value may be set for each small region, or the sound speed value may be set point by point in units of pixels. Further, the sound speed value may be set for the region of interest of the subject or the inspection target region, and the sound speed value set in the region of interest may be used as an optimal sound speed, as will be described below.

Even in these cases, since the sound speed value in the position of the reflection point to be calculated may be adopted as the sound speed value used for calculation of the delay time, it is understood that there is no difference between calculation methods.

Further, it is understood that the sound speed correction unit 76 may merely use, as an optimal sound speed, the sound speed value set by the sound speed changing unit 74 and used in the phasing addition unit 38 when the determination result in the determination unit 72a is OK.

In Embodiment 3, after the determination result in the determination unit 72a is OK, the optimal sound speed of the reception side is lastly set by the sound speed correction unit 76.

The phasing addition unit 38a has exactly the same configuration and function as the phasing addition unit 38, and performs reception focus processing in which a delay is given to the processed element data obtained by the element data processing unit 22 based on the optimal sound speed set by the sound speed correction unit 76 and addition is performed to generate a sound ray signal.

The detection processing unit 40a has exactly the same configuration and function as the detection processing unit 40, and performs processing such as envelope detection processing on the sound ray signal generated by the phasing addition unit 38a to thereby generate B-mode image data that is tomographic image information regarding a tissue of the subject.

The image creation unit 44a has exactly the same configuration and function as the image creation unit 44, and performs image processing on the B-mode image data generated by the detection processing unit 40a to generate an ultrasound image.

Thereafter, the ultrasound image generated in this way is displayed on the display unit 28.

While the sound speed correction unit 76 may set the optimal sound speed used in the phasing addition unit 38a based on the ultrasound image in the inspection target region of the subject as described above, a sound speed optimal for the region of interest of the inspection target region of the subject, that is, a sound speed optimal for the region of interest of the ultrasound image may be set based on the region of interest of the ultrasound image.

This sound speed correction unit is illustrated in FIG. 10A.

The sound speed correction unit 76 calculates the optimal sound speed of the region of interest under the control of the control unit 30 (see FIG. 1), and includes a region-of-interest setting unit 77, a region-of-interest data acquisition unit 78, and the optimal sound speed calculation unit 80, as illustrated in FIG. 10A.

The region-of-interest setting unit 77 sets the region of interest ROI in response to input from the operation unit 32 (see FIG. 1) by an operator.

FIG. 10B is a diagram schematically illustrating an example of the ultrasound image in which the region of interest ROI is set. In the ultrasound image illustrated in FIG. 10B, a target portion P such as a tissue (organ) or a lesion desired to be observed is imaged, and the region of interest ROI is set to surround the target portion P.

The region-of-interest setting unit 77 supplies information on the set region of interest ROI to the region-of-interest data acquisition unit 78.

The region-of-interest setting unit 77 is not limited to a configuration in which the region of interest ROI is set in response to the input from the operation unit 32, and may have a configuration in which the ultrasound image (B-mode image signal) created by the image creation unit 44 of the image generation unit 24 (see FIG. 1) is analyzed and the region of interest ROI is set.

For example, the region-of-interest setting unit 77 may determine that a position (pixel) in which a difference in a brightness value between adjacent pixels in the ultrasound image created by the image creation unit 44 is equal to or greater than a predetermined value is an edge of a structural region (a tissue or a lesion), determine that a region surrounded by the edge or a region including a large number of edges is the structural region, that is, the target portion P, extract the target portion P, and set a region including the target portion P and having a predetermined shape and size as the region of interest ROI.

When the ultrasound image is analyzed and the region of interest ROI is set, the structural region may be considered as a type of region. Alternatively, the structural region may be considered as two or more regions depending on continuity of the edge, a level of the brightness value, or the like, each region may be determined to be the target portion P and extracted, and the region of interest ROI may be set for each target portion P.

The region-of-interest data acquisition unit 78 reads unprocessed element data in a position corresponding to the region of interest ROI from the unprocessed element data stored in the element data storage unit 20 based on information of the region of interest ROI supplied from the region-of-interest setting unit 77, and supplies the unprocessed element data to the optimal sound speed calculation unit 80.

The region-of-interest data acquisition unit 78 is not limited to the configuration in which the unprocessed element data in the position corresponding to the region of interest ROI is read from the element data storage unit 20, and the processed element data in the position corresponding to the region of interest ROI may be supplied from the element data processing unit 22 to the optimal sound speed calculation unit 80. Alternatively, a configuration in which, after the region of interest ROI is set, the probe 36 performs transmission of ultrasonic wave in a state of being focused on the set region of interest ROI, and element data obtained by transmitting ultrasonic waves to the region of interest ROI and receiving ultrasonic echoes is acquired as the element data in the position corresponding to the region of interest ROI may be adopted.

The optimal sound speed calculation unit 80 is a unit that calculates and sets the optimal sound speed value in the set region of interest ROI.

Here, the optimal sound speed value is a set sound speed value in which contrast and/or sharpness of an ultrasound image is highest when the set sound speed is variously changed and reception focus processing is performed based on each of the set sound speeds to form the ultrasound image. For example, a determination of the optimal sound speed value can be performed based on the contrast of the image, a spatial frequency in a scan direction, dispersion or the like, as described in JP 8-317926 A.

The optimal sound speed calculation unit 80 is intended to cyclopedically obtain and set the optimal sound speed value, in which the element data corresponding to the region of interest ROI supplied from the region-of-interest data acquisition unit 78 is an input value, and the optimal sound speed value is an output value.

The optimal sound speed calculation unit 80 may include, for example, an optimal sound speed calculation unit that cyclopedically searches for a predetermined sound speed search range, and sets an optimal sound speed value. The optimal sound speed calculation unit 80 includes a sound speed search range setting unit 82, a sound speed start value setting unit 83, the phasing addition unit 38*d*, a detection processing unit 40*d*, the image creation unit 44*d*, an image quality index calculation unit 84, a sound speed determination unit 85, the comparison determination unit 86, a sound speed value updating unit 87, and the sound speed setting unit 88, as illustrated in FIG. 11.

In the optimal sound speed calculation unit 80, at the time of setting the optimal sound speed, first, the sound speed search range setting unit 82 sets a search range of the sound speed and a sound speed change width when an input value such as element data corresponding to the region of interest ROI is input from the region-of-interest data acquisition unit 78. For example, the sound speed search range setting unit 82 sets a sound speed start value Vst for sound speed search start, a sound speed end value Vend for sound speed search end, and a step width (increment: sound speed change width) $\Delta V$ for change of sound speed value. For example, in the case of a living body or the like, the sound speed start value Vst is set to 1400 m/s, the sound speed end value Vend is set to 1700 m/s, and the sound speed change width $\Delta V$ is set to 10 m/s.

Subsequently, the sound speed start value setting unit 83 sets the set sound speed v to the sound speed start value Vst (for example, 1400 m/s). Then, the phasing addition unit 38*d* performs reception focus processing using the element data corresponding to the region of interest ROI supplied from the region-of-interest data acquisition unit 78 based on the set sound speed v that is the sound speed start value Vst to perform phasing addition and generate a sound ray signal. Then, the detection processing unit 40*d* performs detection processing on the generated sound ray signal to generate a B-mode image signal. Also, the image creation unit 44*d* generates an ultrasound image from the produced B-mode image signal.

Thereafter, the image quality index calculation unit 84 calculates an image quality index at the set sound speed v from the generated ultrasound image, that is, an image quality index such as a brightness value or sharpness of the image, for example, sharpness of the image of the region of interest ROI at each set sound speed v. The calculated image quality index is associated with the set sound speed value v, and held in the image quality index calculation unit 84, such as a memory.

Then, the sound speed determination unit 85 performs a determination as to whether the set sound speed v and the sound speed end value Vend are equal by comparing the set sound speed v with the sound speed end value Vend.

In the determination of the sound speed determination unit 85, when the set sound speed v is equal to the sound speed end value Vend (v=Vend), the process proceeds to the comparison determination unit 86, and when the set sound speed v is not equal to the sound speed end value Vend (v≠Vend), the process proceeds to the sound speed value updating unit 87.

When the process proceeds to the sound speed value updating unit 87, the sound speed value updating unit 87 adds the sound speed change width ΔV to the current set sound speed v to set a new set sound speed v (v=v+ΔV).

Thereafter, the process returns to the phasing addition unit 38*d*. The phasing addition in the phasing addition unit 38*d*, the detection processing in the detection processing unit 40*d*, the image creation in the image creation unit 44*d*, the calculation and holding of the image quality index in the image quality index calculation unit 84, and the determination in the sound speed determination unit 85 are performed based on the new set sound speed v.

When the determination result in the sound speed determination unit 85 is v≠Vend, the process proceeds to the sound speed value updating unit 87, as described above. The setting of the new set sound speed v in the sound speed value updating unit 87, the phasing addition in the phasing addition unit 38*d* based on the new set sound speed v, the detection processing in the detection processing unit 40*d*, the image creation in the image creation unit 44*d*, the calculation and holding of the image quality index in the image quality index calculation unit 84, and the determination in the sound speed determination unit 85 are repeated until v becomes v=Vend. That is, these processing steps are repeatedly performed while changing the value of the set sound speed by ΔV until the sound speed end value Vend of the end of the sound speed range arrives. For example, the set sound speed v is changed with an increment of 10 m/s from 1400 m/s to 1700 m/s.

On the other hand, when the determination result of the sound speed determination unit 85 is v=Vend, the image quality index is obtained for all set sound speeds v in the search range of the sound speed. Accordingly, as described above, the process proceeds to the comparison determination unit 86, and the comparison determination unit 86 reads the image quality index obtained for each sound speed value, which is stored in the image quality index calculation unit 84. The comparison determination unit 86 compares the image quality indexes in the respective set sound speeds v, such as the sharpness (sharpness values) of the ultrasound image, and determines the set sound speed (sound speed value) v when the image quality is highest, for example, when the sharpness (sharpness value) of the ultrasound image is highest. The sound speed setting unit 88 adopts and sets the sound speed (sound speed value) v determined by the comparison determination unit 86 as an optimal sound speed.

Thus, the optimal sound speed calculation unit 80 calculates the optimal sound speed.

In the optimal sound speed calculation unit 80 illustrated in FIG. 11, while the processing of changing the sound speed value is repeatedly performed, the present invention is not limited thereto, and all search sound speed values can be calculated in parallel using multi-thread of a GPU or the like, and the image quality index can be obtained in all the sound speed values at a time.

The element data used in the phasing addition performed by the phasing addition unit 38*d* of the optimal sound speed calculation unit 80 may be the unprocessed element data supplied from the element data storage unit 20 or may be the processed element data supplied from the element data processing unit 22. The unprocessed element data may be the unprocessed element data directly supplied from the element data storage unit 20 or may be unprocessed element data supplied without being processed from the element data processing unit 22.

The optimal sound speed calculation unit 80 supplies the optimal sound speed value calculated and set in this way to the phasing addition unit 38 of the image generation unit 24.

When the ultrasound image is generated, by setting the region of interest in the ultrasound image and obtaining the optimal sound speed value in the region of interest, as described above, can be obtained effects that the spatial resolution of the image of the region of interest, that is, a tissue or a lesion desired to be observed is optimized and the optimal sound speed value is obtained in a short time.

The sound speed correction unit 76 illustrated in FIG. 10A includes the region-of-interest setting unit 77, the region-of-interest data acquisition unit 78, and the optimal sound speed calculation unit 80. However, when the sound speed correction unit 76 sets, as the region for which the same sound speed value is set, the entire subject or the entire inspection target region, as described above, the region-of-interest setting unit 77 may be omitted or the entire subject or the entire inspection target region may be set as the region of interest and the region-of-interest data acquisition unit 78 may acquire all pieces of data of the entire subject or the entire inspection target region. Further, when the subject or the inspection target region is divided into small regions and the sound speed value is set for each small regions, or when the sound speed value is set point by point in units of pixels, the region-of-interest setting unit 77 may set one point of the small region or the pixel unit as the region of interest, and the region-of-interest data acquisition unit 78 may acquire data of the one point of the small region or the pixel unit.

While in the ultrasonic inspection apparatus 70*c* illustrated in FIG. 9, the determination unit 72*a* is provided between the image creation unit 44 and the display unit 28, as in the ultrasonic inspection apparatus 70*a* illustrated in FIG. 8A, the present invention is not limited thereto, and the determination unit 72*b* may be provided between the phasing addition unit 38 and the detection processing unit 40 as in the ultrasonic inspection apparatus 70*b* illustrated in FIG. 8B, like the ultrasonic inspection apparatus 70*d* illustrated in FIG. 12.

The ultrasonic inspection apparatus 70*d* illustrated in FIG. 12 includes the transmission unit 14, the probe 36, the reception unit 16, the element data storage unit 20, the element data processing unit 22, the phasing addition unit 38, a determination unit 72*b*, the sound speed changing unit 74, a sound speed correction unit 76*a*, the phasing addition unit 38*a*, the detection processing unit 40, the image creation unit 44, and the display unit 28.

Here, since the processing in the probe 36, the transmission unit 14, the reception unit 16, and the element data storage unit 20, the processing in the element data processing unit 22, the phasing addition unit 38, the determination unit 72*b* and the sound speed changing unit 74 until the determination result in the determination unit 72*b* is OK, and the processing in the detection processing unit 40, the image creation unit 44, and the display unit 28 after the determination result in the determination unit 72*b* is OK are performed as in the ultrasonic inspection apparatus 70*a* illustrated in FIG. 8B, description thereof will be omitted.

In the ultrasonic inspection apparatus 70*d* of Embodiment 3, the sound speed correction unit 76*a* is provided between the determination unit 72*b* and the phasing addition unit 38*a*, has the same configuration and function as the sound speed correction unit 76 illustrated in FIG. 9 or 10A, and is intended to obtain an optimal sound speed of the reception side, that is, a sound speed optimal for the inspection target region of the subject, and accordingly, a sound speed optimal for the ultrasound image thereof, to be used in the phasing addition unit 38a of the subsequent stage. Naturally, the sound speed correction unit 76a may determine the sound speed value set by the sound speed changing unit 74 and used in the phasing addition unit 38 to be the optimal sound speed as it is, when the determination result in the determination unit 72b is OK.

In the ultrasonic inspection apparatus 70d, the optimal sound speed of the reception side is set by the sound speed correction unit 76a after the determination result in the determination unit 72b is OK.

Then, in the phasing addition unit 38a, a delay is given to the processed element data obtained by the element data processing unit 22, based on the optimal sound speed set by the sound speed correction unit 76a to perform the reception focus processing, and the sound ray signal is generated.

Then, in the detection processing unit 40, the detection processing is performed on the sound ray signal generated by the phasing addition unit 38a, and B-mode image data is generated.

Then, in the image creation unit 44, an ultrasound image is created from the B-mode image data generated by the detection processing unit 40.

Thereafter, the ultrasound image created in this way is displayed on the display unit 28.

Thus, since the ultrasonic inspection apparatuses 70c and 70d of Embodiment 3 of the present invention create an ultrasound image using the processed element data that is processed using an optimal sound speed and in which the ghost signal is attenuated and the true signal is emphasized in the element data processing unit 22, it is possible to obtain a sharp ultrasound image having a high SN ratio and an optimal spatial resolution with high resolution that does not depend on the width of the transmission beam, without using a dedicated ultrasound probe for generating a wide transmission ultrasonic beam and at a frame rate that is not different from the conventional frame rate.

The ultrasonic inspection apparatus of Embodiment 3 of the present invention is basically configured as described above.

Embodiment 4

Next, an ultrasonic inspection apparatus of Embodiment 4 of the present invention will be described based on FIG. 13.

Figure 13:
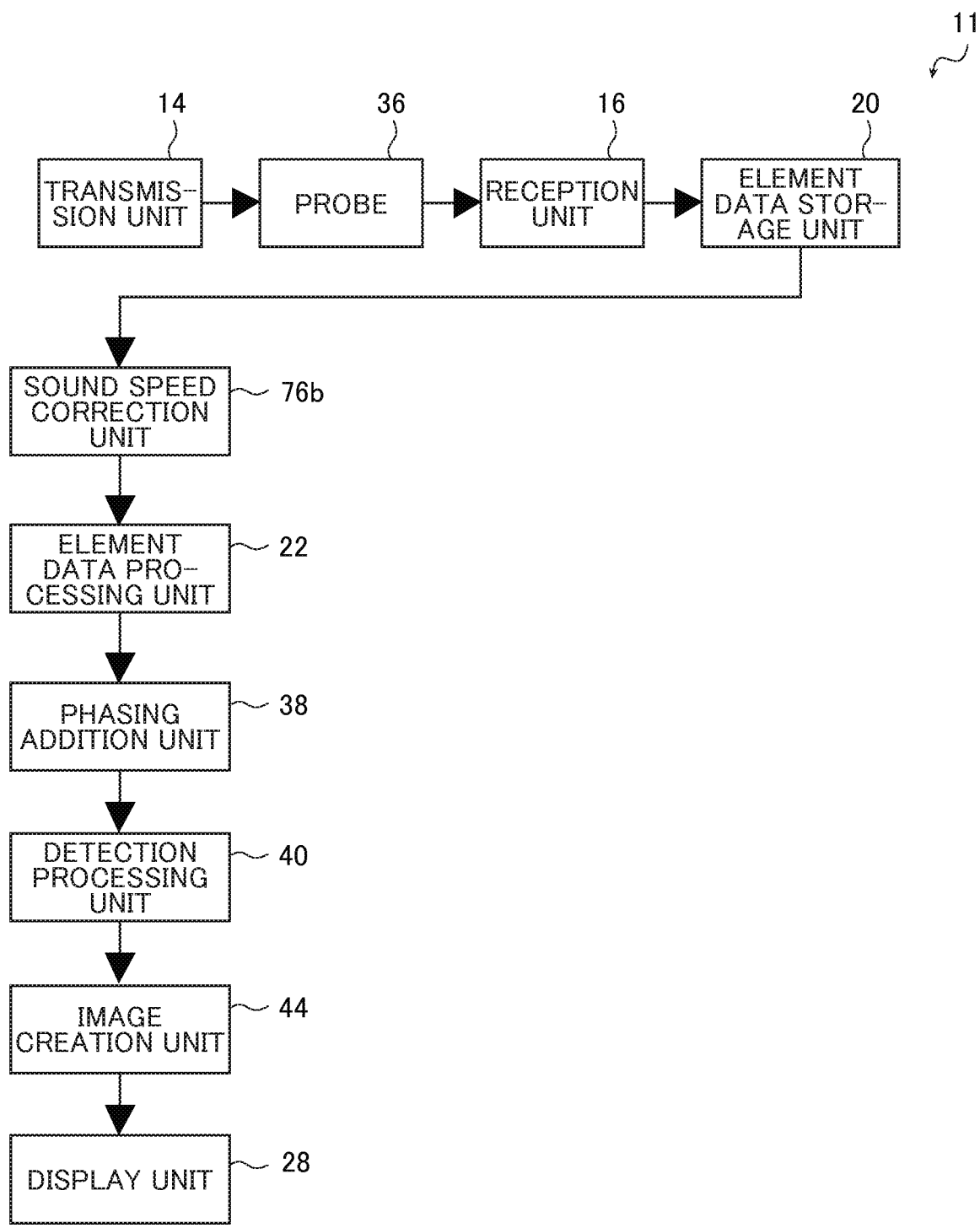
FIG. 13 is a block diagram conceptually illustrating, along a process flow, an example of primary units of an ultrasonic inspection apparatus of Embodiment 4 of the present invention.

FIG. 13 is a block diagram conceptually illustrating, along a process flow, an example of primary units of the ultrasonic inspection apparatus of Embodiment 4 of the present invention.

An ultrasonic inspection apparatus 11 includes the transmission unit 14, the probe 36, the reception unit 16, the element data storage unit 20, a sound speed correction unit 76b, the element data processing unit 22, the phasing addition unit 38, the detection processing unit 40, the image creation unit 44, and the display unit 28, as illustrated in FIG. 13.

Since the ultrasonic inspection apparatus 11 illustrated in FIG. 13 has exactly the same configuration as the ultrasonic inspection apparatus 10 illustrated in FIGS. 1 and 7 except that the sound speed correction unit 76b is included, the same components are denoted with the same reference signs and detailed description thereof will be omitted.

Further, in the ultrasonic inspection apparatus 11, the processing in the probe 36, the transmission unit 14, the reception unit 16, and the element data storage unit 20, and the processing in the phasing addition unit 38, the detection processing unit 40, the image creation unit 44, and the display unit 28 are performed as in the ultrasonic inspection apparatus 10 illustrated in FIG. 7. Accordingly, description thereof will be omitted.

In the ultrasonic inspection apparatus 11 of Embodiment 4, the sound speed correction unit 76b performs sound speed correction on the element data before being subjected to element data processing to obtain an optimal sound speed, and the element data processing unit 22 calculates a delay time based on the obtained optimal sound speed and performs a superposition processing.

The sound speed correction unit 76b is provided between the element data storage unit 20 and the element data processing unit 22, has the same configuration and function as the sound speed correction unit 76 illustrated in FIG. 9 or 10A, and is intended to obtain an optimal sound speed of the reception side, that is, a sound speed optimal for the inspection target region of the subject, to be used to calculate the delay time in the delay time calculation unit 48 of the element data processing unit 22 of the subsequent stage and perform reception focus processing in the phasing addition unit 38 of the subsequent stage.

In the element data processing unit 22, the delay time calculation unit 48 calculates the delay time of neighboring unprocessed element data relative to the element data of the element of interest using the optimal sound speed of the inspection target region of the subject set by the sound speed correction unit 76b and a geometric arrangement of the transmission element, the focal point, the reflection point, and the reception element, as described above.

Then, in the element data processing unit 22, the superposition processing unit 50 phases and superimposes the element data of the element of interest and neighboring unprocessed element data to obtain the processed element data using the delay time calculated by the delay time calculation unit 48, and supplies the processed element data to the phasing addition unit 38.

Then, in the phasing addition unit 38, a delay is given to the processed element data supplied from the element data processing unit 22 based on the optimal sound speed set by sound speed correction unit 76b to perform reception focus processing, and a sound ray signal is generated.

Then, in the detection processing unit 40, the detection processing is performed on the sound ray signal generated by the phasing addition unit 38 to generate B-mode image data, and in the image creation unit 44, an ultrasound image is created from the B-mode image data generated by the detection processing unit 40. The ultrasound image is displayed on the display unit 28.

Thus, in the ultrasonic inspection apparatus 11 of Embodiment 4 of the present invention, an ultrasound image is created using the processed element data in which the ghost signal is attenuated and the true signal is emphasized, which is processed in the element data processing unit 22 using the optimal sound speed set by the sound speed correction unit 76b. Accordingly, it is possible to obtain a sharp ultrasound image having a high SN ratio and an optimal spatial resolution with high resolution that does not depend on the width of the transmission beam, without using a dedicated ultrasound probe for generating a wide transmission ultrasonic beam and at a frame rate that is not different from the conventional frame rate.

The ultrasonic inspection apparatus of Embodiment 4 of the present invention is basically configured as described above.

Embodiment 5

Next, an ultrasonic inspection apparatus of Embodiment 5 of the present invention will be described based on FIGS. 14 to 17.

Each of FIGS. 14 to 17 is a block diagram conceptually illustrating, along a process flow, an example of primary units of the ultrasonic inspection apparatus according to Embodiment 5 of the present invention.

Ultrasonic inspection apparatuses 90a to 90d illustrated in FIGS. 14 to 17 have exactly the same configuration as the ultrasonic inspection apparatus 10 illustrated in FIGS. 1 and 7 except that a sound speed correction unit 76c and determination units 72a and 72b are included. Accordingly, the same components are denoted with the same reference signs and detailed description thereof will be omitted.

Figure 14:
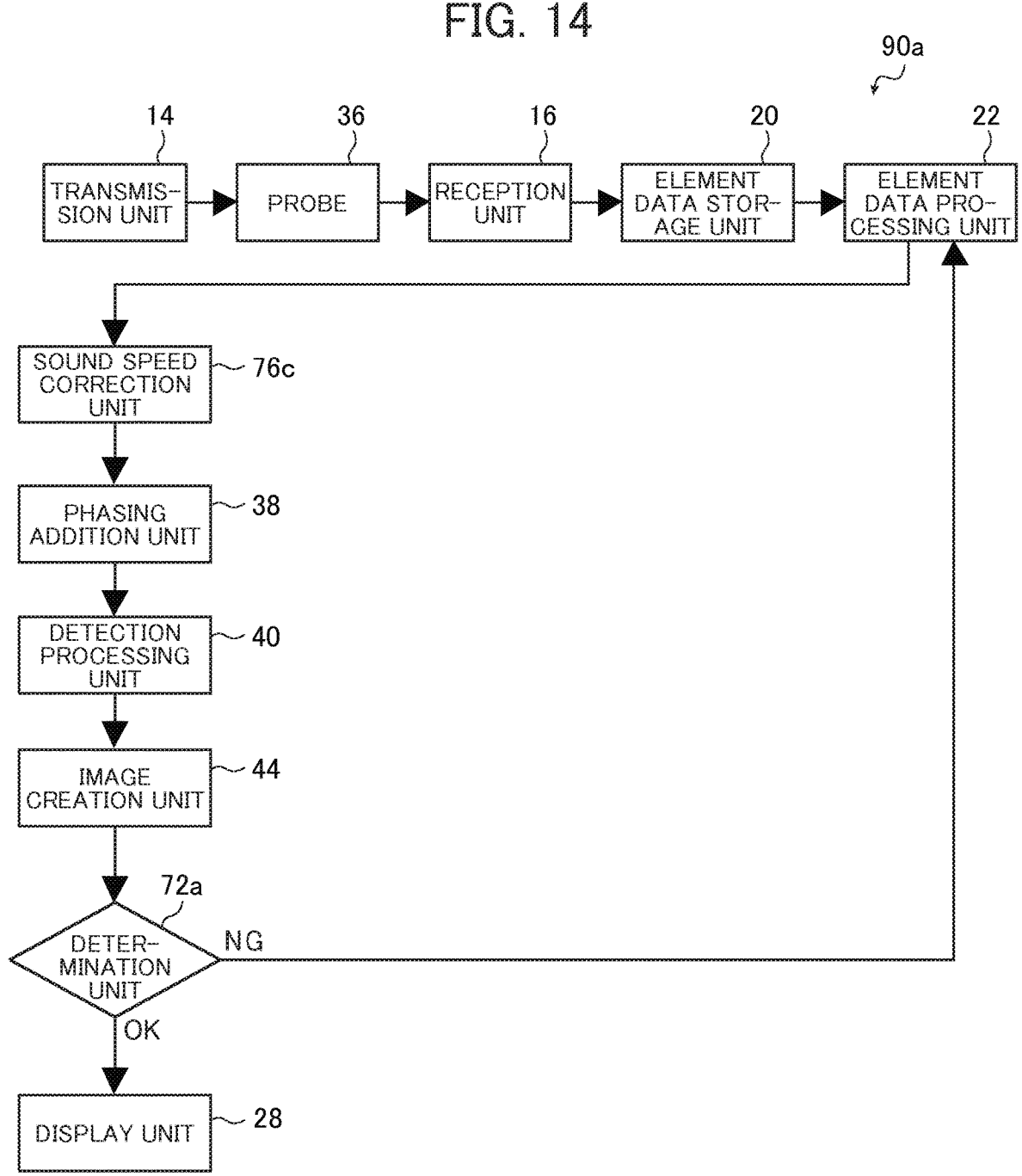
FIG. 14 is a block diagram conceptually illustrating, along a process flow, an example of primary units of an ultrasonic inspection apparatus of Embodiment 5 of the present invention.

First, the ultrasonic inspection apparatus 90a illustrated in FIG. 14 will be described. FIG. 14 illustrates, along a process flow, the primary units of the ultrasonic inspection apparatus 90a, as in FIG. 7.

The ultrasonic inspection apparatus 90a includes the transmission unit 14, the probe 36, the reception unit 16, the element data storage unit 20, the element data processing unit 22, a sound speed correction unit 76c, the phasing addition unit 38, the detection processing unit 40, the image creation unit 44, the determination unit 72a, and the display unit 28, as illustrated in FIG. 14.

Here, the processing in the probe 36, the transmission unit 14, the reception unit 16, and the element data storage unit 20, and the first time processing in the element data processing unit 22, the detection processing unit 40, and the image creation unit 44 are performed as in the ultrasonic inspection apparatus 10 illustrated in FIGS. 1 and 7. Accordingly, description thereof will be omitted.

The sound speed correction unit 76c is provided between the element data processing unit 22 and the phasing addition unit 38 of the image generation unit 24, has the same configuration and function as the sound speed correction unit 76 illustrated in FIG. 9 or 10A, and is intended to obtain an optimal sound speed of the reception side, that is, a sound speed optimal for the inspection target region of the subject, to be used to perform reception focus processing in the phasing addition unit 38 of the subsequent stage on the processed element data obtained by the element data processing unit 22 of the preceding stage. For example, the sound speed correction unit 76c may change the set sound speed v with an increment of 10 m/s from 1400 m/s to 1700 m/s and the determination unit 72a may perform a determination based on the image quality index such as the brightness value or the sharpness of the image or the degree of convergence of the sound speed to obtain the optimal sound speed. Needless to say, the sound speed correction unit 76c may determine an initial value of the sound speed set in advance, which is used to calculate the delay time in the delay time calculation unit 48 of the element data processing unit 22, as an optimal sound speed as it is.

In first time processing, the element data processing unit 22 performs element data processing using an initial value of the sound speed set in advance. That is, in the element data processing unit 22, the delay time calculation unit 48 calculates the delay time using the initial value of the sound speed set in advance, the superposition processing unit 50 performs superposition processing on two or more pieces of unprocessed element data using the calculated delay time to obtain processed element data, and the sound speed correction unit 76c of the subsequent stage obtains the optimal sound speed of the reception side and sends the optimal sound speed to the phasing addition unit 38 of the subsequent stage together with the processed element data.

The phasing addition unit 38 performs reception focus processing in which a delay is given to the processed element data obtained by the element data processing unit 22 based on the optimal sound speed set by the sound speed correction unit 76c and addition is performed, and generates a sound ray signal.

Then, the detection processing unit 40 performs the detection processing on the generated sound ray signal to generate a B-mode image signal, and the image creation unit 44 performs the image processing on the generated B-mode image signal to create an ultrasound image.

The determination unit 72a has the same configuration and function as the determination unit 72a illustrated in FIG. 8A or 9, performs a determination based on the ultrasound image created by the image creation unit 44 using the created ultrasound image to determine "suitable" or OK, for example, when the image quality index such as the sharpness of the brightness value of the ultrasound image is higher than a predetermined value, and otherwise determine "unsuitable" or NG.

When the determination unit 72a determines OK, the ultrasound image created by the image creation unit 44 is sent to the display unit 28 and displayed on the display screen.

On the other hand, when the determination unit 72a determines NG, the process returns to the element data processing unit 22. In second time and subsequent processing, the delay time calculation unit 48 of the element data processing unit 22 calculates the delay time using the optimal sound speed set by the sound speed correction unit 76c again. Thereafter, the superposition processing unit 50 performs the superposition processing on the two or more pieces of unprocessed element data using the delay time calculated using the optimal sound speed to obtain processed element data.

After the element data processing unit 22 obtains the processed element data in this way, the sound speed correction unit 76c newly sets a new optimal sound speed, the phasing addition unit 38 performs reception focus processing on the processed element data obtained by the element data processing unit 22 based on the new optimal sound speed newly set by the sound speed correction unit 76c to generate a sound ray signal (reception data), the detection processing unit 40 performs the detection processing as in the first process, the image creation unit 44 performs image processing to create an ultrasound image, and the determination unit 72a performs the determination.

As described above, in the second time and subsequent processing, the respective processing in the element data processing unit 22, the sound speed correction unit 76c, the phasing addition unit 38, the detection processing unit 40, the image creation unit 44 and the determination unit 72a are repeated until the determination of the determination unit 72a is OK. After the determination of the determination unit 72a is OK, an ultrasound image is displayed on the display unit 28.

Even when the setting of the new optimal sound speed in the sound speed correction unit 76c is all performed in a predetermined sound speed range, for example, even when the setting is performed at predetermined intervals in the predetermined entire sound speed range, if the determination of the determination unit 72a is not OK, for example, a sound speed value when a determination closest to a determination criteria is obtained may be adopted as the optimal sound speed.

Next, the ultrasonic inspection apparatus 90b illustrated in FIG. 15 will be described.

Figure 15:
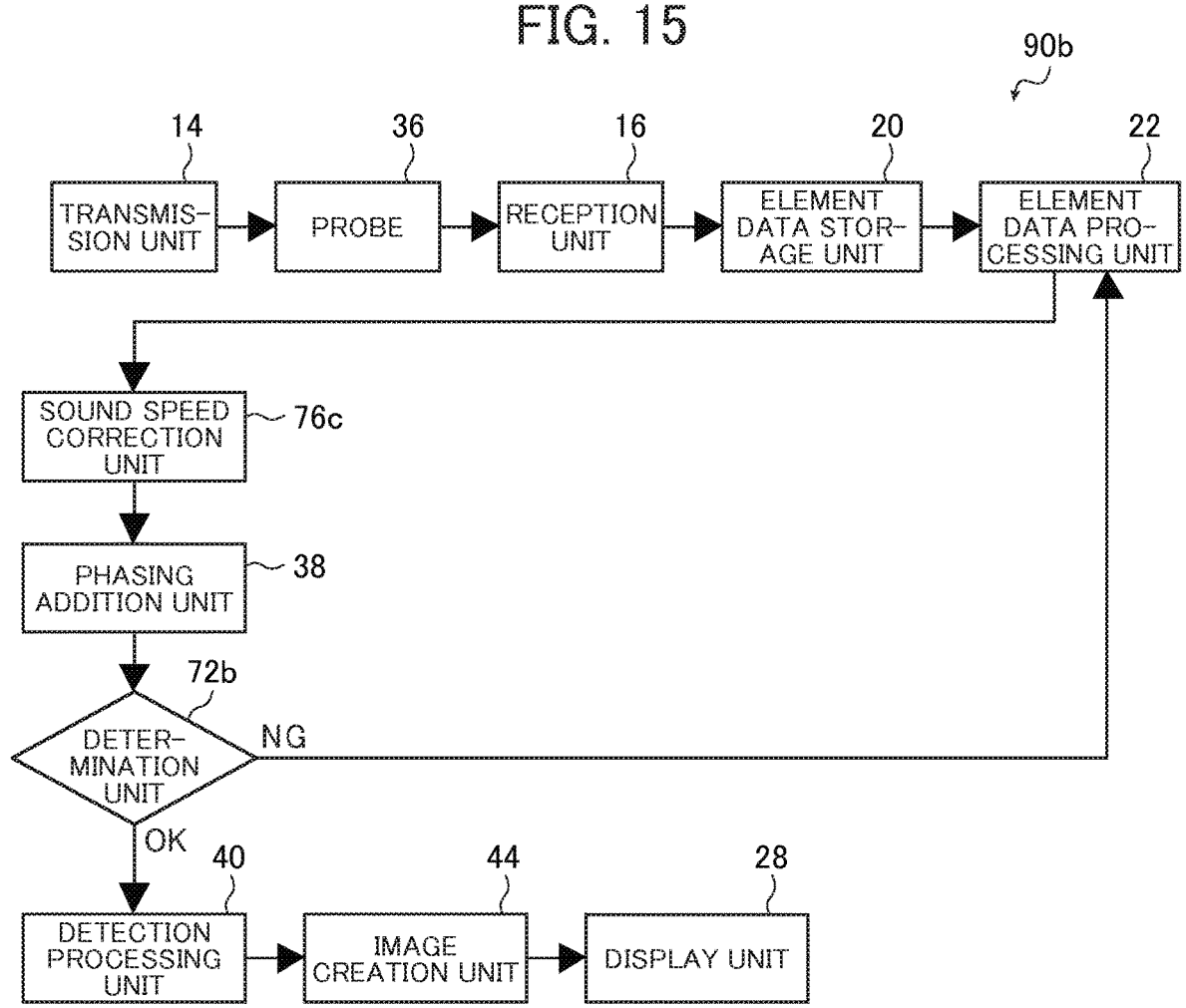
FIG. 15 is a block diagram conceptually illustrating, along a process flow, another example of primary units of an ultrasonic inspection apparatus of Embodiment 5 of the present invention.

The ultrasonic inspection apparatus 90b illustrated in FIG. 15 has exactly the same configuration as the ultrasonic inspection apparatus 90a illustrated in FIG. 14 except that the determination unit 72b is provided between the phasing addition unit 38 and the detection processing unit 40, whereas in the ultrasonic inspection apparatus 90a illustrated in FIG. 14, the determination unit 72a is provided between the image creation unit 44 and the display unit 28. Accordingly, the same components are denoted with the same reference signs and detailed description thereof will be omitted.

The ultrasonic inspection apparatus 90b includes the transmission unit 14, the probe 36, the reception unit 16, the element data storage unit 20, the element data processing unit 22, the sound speed correction unit 76c, the phasing addition unit 38, the determination unit 72b, the detection processing unit 40, the image creation unit 44, and the display unit 28, as illustrated in FIG. 15.

Here, since the processing in the probe 36, the transmission unit 14, the reception unit 16, and the element data storage unit 20, the processing in the detection processing unit 40, the image creation unit 44, and the display unit 28, and the first time processing in the element data processing unit 22, the sound speed correction unit 76c, and the phasing addition unit 38 are performed as in the ultrasonic inspection apparatus 90a illustrated in FIG. 14, description thereof will be omitted.

After the element data processing unit 22 obtains the processed element data, the sound speed correction unit 76c obtains an optimal sound speed of the reception side, that is, a sound speed optimal for the inspection target region of the subject, to be used in the phasing addition unit 38. For example, the sound speed correction unit 76c may change the set sound speed v with a predetermined sound speed increment in a predetermined sound speed range, and the determination unit 72b may obtain the optimal sound speed through a determination based on the image quality index such as the brightness value or the sharpness of the image or the degree of convergence of sound speed.

The phasing addition unit 38 performs reception focus processing in which a delay is given to the processed element data obtained by the element data processing unit 22 based on the optimal sound speed set by the sound speed correction unit 76c and addition is performed, and generates a sound ray signal (reception data).

The determination unit 72b has the same configuration and function as the determination unit 72b illustrated in FIG. 8B or 12, and performs a determination based on the image quality index such as the brightness value or the sharpness of the image, or the sharpness of the brightness value, or the degree of convergence of the sound speed using the sound ray signal generated by the reception focus processing in the phasing addition unit 38. The determination unit 72b determines OK when the image quality index such as the brightness value or the sharpness is highest, and determines NG when the image quality index such as the brightness value or the sharpness does not reach the highest value.

When the determination unit 72b determines OK, the process proceeds to the detection processing unit 40, and the detection processing unit 40 performs an envelope detection processing or the like on the sound ray signal generated by the phasing addition unit 38 to thereby generate B-mode image data that is tomographic image information regarding the tissue of the subject. Therefore, an ultrasound image is created by the image creation unit 44 and displayed on the display unit 28.

On the other hand, when the determination unit 72b determines NG, the process returns to the element data processing unit 22, and the delay time calculation unit 48 of the element data processing unit 22 calculates the delay time again using the optimal sound speed set by the sound speed correction unit 76c. Thereafter, the superposition processing unit 50 performs the superposition processing on the two or more pieces of unprocessed element data using the delay time calculated using the optimal sound speed to obtain processed element data.

After the element data processing unit 22 obtains the processed element data in this way, the sound speed correction unit 76c newly sets an optimal sound speed, the phasing addition unit 38 performs the reception focus processing on the processed element data obtained by the element data processing unit 22 based on the new optimal sound speed newly set by the sound speed correction unit 76c to generate a sound ray signal (reception data), and the determination unit 72b performs the determination based on the image quality index such as the brightness value or the sharpness of the image, or the degree of convergence of sound speed using the sound ray signal generated by the phasing addition unit 38.

If the determination of the determination unit 72b is OK, the generation of the B-mode image data in the detection processing unit 40, the creation of the ultrasound image in the image creation unit 44, and the displaying of the ultrasound image in the display unit 28 are performed.

In contrast, if the determination of the determination unit 72b is NG, the calculation of the delay time in the delay time calculation unit 48 of the element data processing unit 22 using the optimal sound speed set by the sound speed correction unit 76c, the generation of the processed element data in the superposition processing unit 50, the new setting of the sound speed in the sound speed correction unit 76c, and the generation of the sound ray signal for the processed element data obtained by the element data processing unit 22 based on the optimal sound speed newly set by the sound speed correction unit 76c in the phasing addition unit 38 are repeated until the determination is OK, that is, until the optimal sound speed is set.

While the sound speed correction unit 76c is provided in the subsequent stage of the element data processing unit 22 in the ultrasonic inspection apparatuses 90a and 90b illustrated in FIGS. 14 and 15, the present invention is not limited thereto, and the sound speed correction unit 76c may be provided in a preceding stage of the element data processing unit 22.

Figure 16:
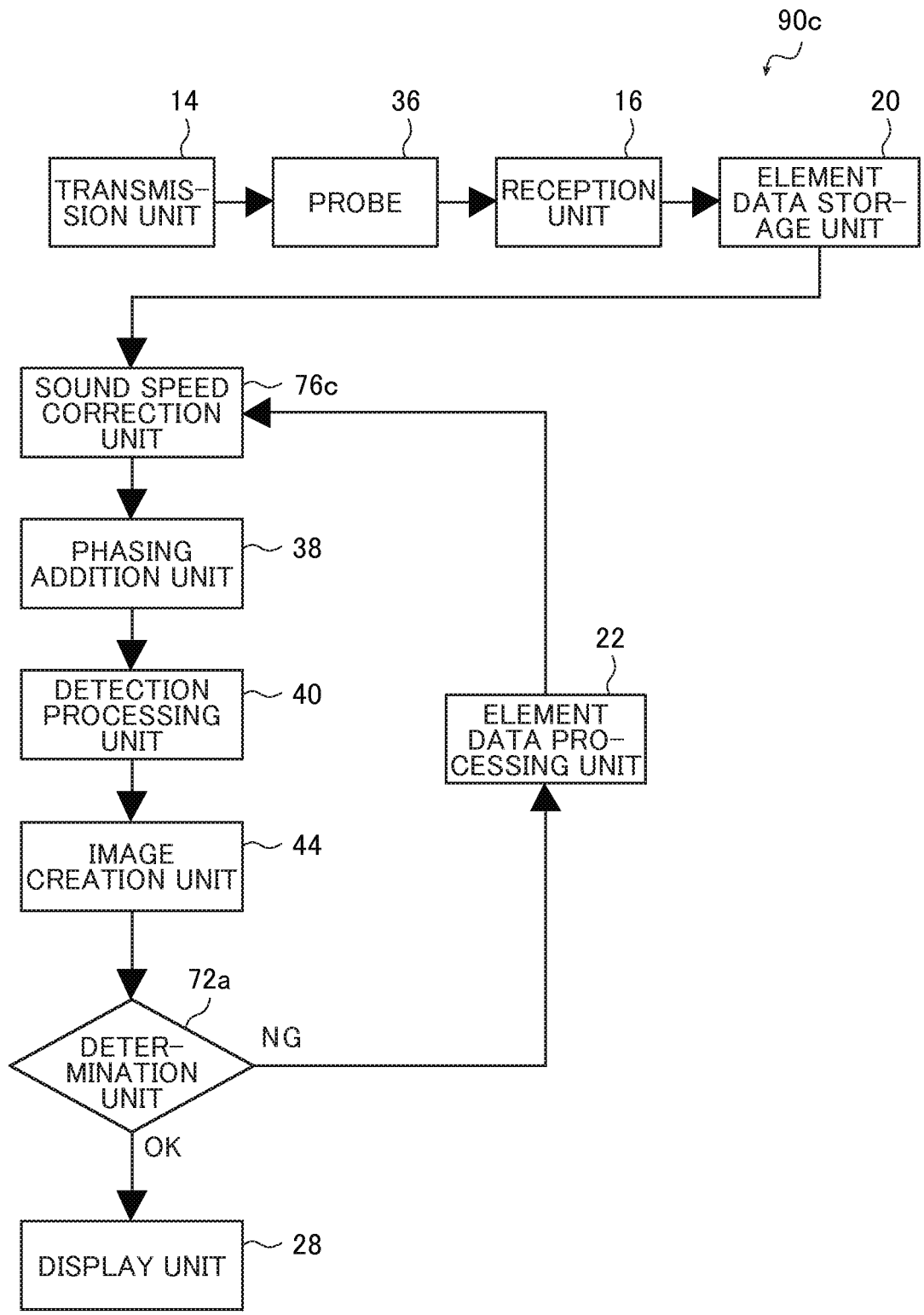
FIG. 16 is a block diagram conceptually illustrating, along a process flow, another example of primary units of an ultrasonic inspection apparatus of Embodiment 5 of the present invention.
Figure 17:
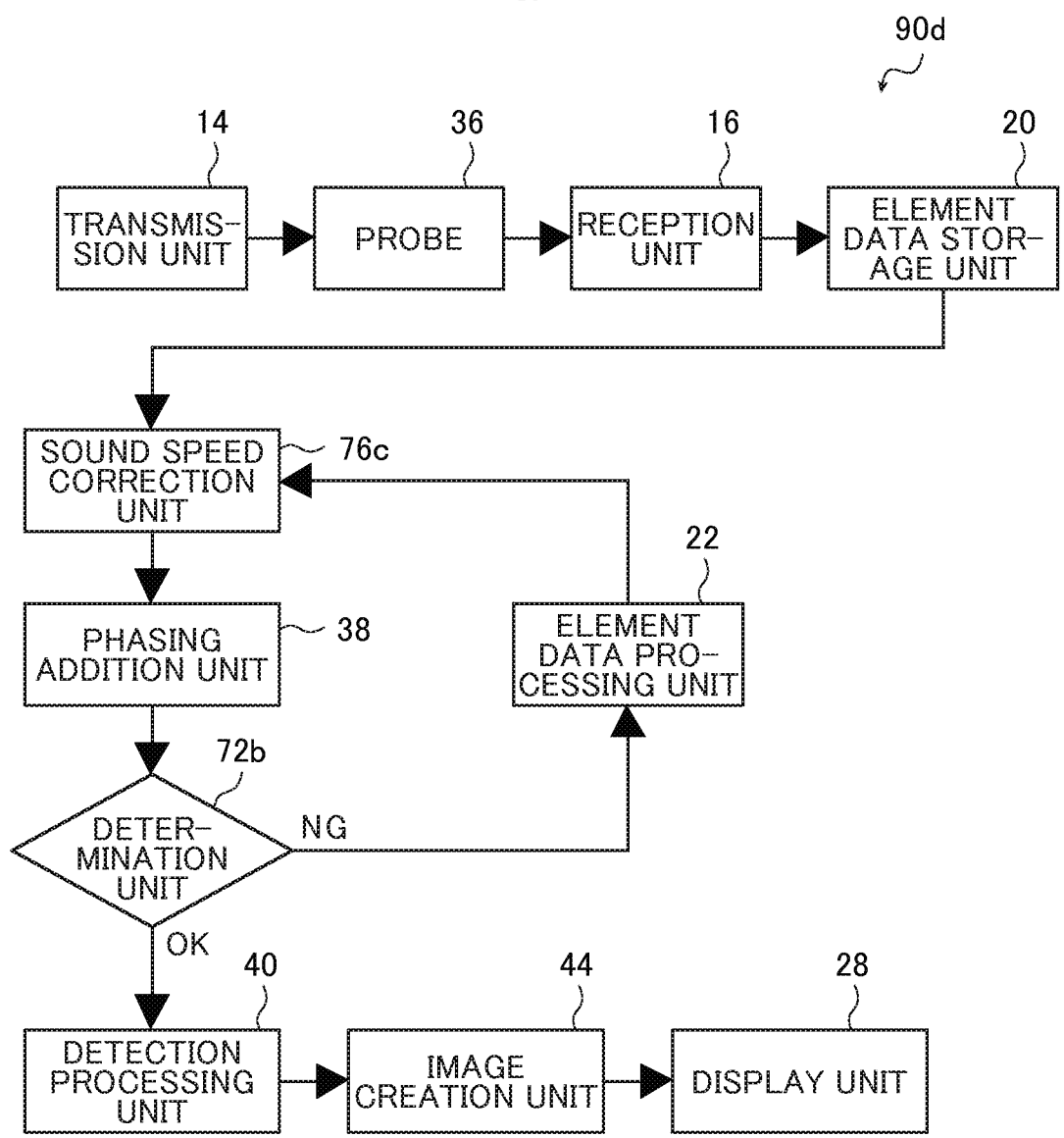
FIG. 17 is a block diagram conceptually illustrating, along a process flow, another example of primary units of an ultrasonic inspection apparatus of Embodiment 5 of the present invention.

FIGS. 16 and 17 are block diagrams illustrating primary units of the ultrasonic inspection apparatuses 90c and 90d along a process flow as in FIGS. 14 and 15. The ultrasonic inspection apparatuses 90c and 90d include the same components as the ultrasonic inspection apparatuses 90a and 90b illustrated in FIGS. 14 and 15 except for the difference of the process flow.

The ultrasonic inspection apparatus 90c illustrated in FIG. 16 includes the probe 36, the transmission unit 14, the reception unit 16, the element data storage unit 20, the sound speed correction unit 76c, the phasing addition unit 38, the element data processing unit 22, the detection processing unit 40, the image creation unit 44, the determination unit 72a, and the display unit 28.

The ultrasonic inspection apparatus 90d illustrated in FIG. 17 includes the probe 36, the transmission unit 14, the reception unit 16, the element data storage unit 20, the sound speed correction unit 76c, the phasing addition unit 38, the determination unit 72b, the element data processing unit 22, the detection processing unit 40, the image creation unit 44, and the display unit 28.

Here, in the ultrasonic inspection apparatuses 90c and 90d illustrated in FIGS. 16 and 17, the processing in the probe 36, the transmission unit 14, the reception unit 16, and the element data storage unit 20 are performed as in the ultrasonic inspection apparatuses 90a and 90b illustrated in FIGS. 14 and 15. Accordingly, description thereof will be omitted.

The sound speed correction unit 76c of the ultrasonic inspection apparatuses 90c and 90d illustrated in FIGS. 16 and 17 is different from the sound speed correction unit 76c of the ultrasonic inspection apparatuses 90a and 90b illustrated in FIGS. 14 and 15 in that the sound speed correction unit 76c is provided between the element data storage unit 20 and the phasing addition unit 38 in the first time processing. However, since the sound speed correction unit 76c is provided between the element data processing unit 22 and the phasing addition unit 38 in the second time and subsequent processing, the sound speed correction unit 76c of the ultrasonic inspection apparatuses 90c and 90d is exactly the same as the sound speed correction unit 76c of the ultrasonic inspection apparatus 90a and 90b illustrated in FIGS. 14 and 15. They are also exactly the same as each other in that the optimal sound speed of the reception side to be used in the phasing addition unit 38, that is, the sound speed optimal for the inspection target region of the subject is obtained. Accordingly, detailed description thereof will be omitted. In the first time processing, the optimal sound speed is initially set in the sound speed correction unit 76c, but naturally, the initial value of the sound speed set in advance may be set as the optimal sound speed as it is.

First, the ultrasonic inspection apparatus 90c illustrated in FIG. 16 will be described.

In the ultrasonic inspection apparatus 90c illustrated in FIG. 16, the sound speed correction unit 76c sets the optimal sound speed of the reception side of the inspection target region of the subject for the unprocessed element data read from the element data storage unit 20, in the first time processing. The phasing addition unit 38 performs reception focus processing in which a delay is given to the unprocessed element data based on the optimal sound speed set by the sound speed correction unit 76c and addition is performed, and generates a sound ray signal (reception data). Then, the detection processing unit 40 performs the detection processing on the generated sound ray signal to generate a B-mode image signal, and the image creation unit 44 performs image processing on the generated B-mode image signal to create an ultrasound image.

The determination unit 72a performs a determination based on the ultrasound image created by the image creation unit 44 using the created ultrasound image and determines "suitable" or OK, for example, when the image quality index such as the sharpness of the brightness value of the ultrasound image is higher than a predetermined value, and otherwise determines "unsuitable" or NG.

When the determination unit 72a determines OK, the ultrasound image created by the image creation unit 44 is sent to the display unit 28 and displayed on the display screen.

On the other hand, when the determination unit 72a determines NG, second time and subsequent processing is performed, and the process returns to the element data processing unit 22. The delay time calculation unit 48 of the element data processing unit 22 calculates the delay time again using the optimal sound speed set by the sound speed correction unit 76c, and the superposition processing unit 50 performs superposition processing on the two or more pieces of unprocessed element data using the delay time calculated using the optimal sound speed to obtain the processed element data.

In the second time and subsequent processing, after the element data processing unit 22 obtains the processed element data in this way, the sound speed correction unit 76c newly sets a new optimal sound speed, the phasing addition unit 38 performs reception focus processing on the processed element data obtained by the element data processing unit 22 based on the new optimal sound speed newly set by the sound speed correction unit 76c to generate a sound ray signal (reception data), the detection processing unit 40 performs the detection processing as in the first time processing, the image creation unit 44 performs image processing to create an ultrasound image, and the determination unit 72a performs the determination.

As described above, in the second time and subsequent processing, the respective processing in the element data processing unit 22, the sound speed correction unit 76c, the phasing addition unit 38, the detection processing unit 40, the image creation unit 44 and the determination unit 72a are repeated until the determination unit 72a determines OK. After the determination unit 72a determines OK, the ultrasound image is displayed on the display unit 28.

Even when the setting of the new optimal sound speed in the sound speed correction unit 76c is all performed in a predetermined sound speed range, for example, even when the setting is performed at predetermined intervals in the predetermined entire sound speed range, if the determination of the determination unit 72a is not OK, for example, a sound speed value when a determination closest to a determination criteria is obtained may be set as the optimal sound speed.

Next, the ultrasonic inspection apparatus 90d illustrated in FIG. 17 will be described.

In the ultrasonic inspection apparatus 90d illustrated in FIG. 17, first, the sound speed correction unit 76c sets the optimal sound speed of the reception side of the inspection target region of the subject for the unprocessed element data read from the element data storage unit 20, in the first time processing.

The phasing addition unit 38 performs reception focus processing of giving a delay based on the optimal sound speed set by the sound speed correction unit 76c and performing addition on the unprocessed element data read from the element data storage unit 20 in the first time processing, and on the processed element data obtained in the element data processing unit 22 in the second time and subsequent processing, to thereby generate a sound ray signal (reception data).

The determination unit 72b is provided between the phasing addition unit 38, and the detection processing unit 40 and the element data processing unit 22. In the first time processing, the determination unit 72b automatically determines NG. In the second time and subsequent processing, the determination unit 72b performs the determination based on the image quality index such as the brightness value or the sharpness of the image, or the degree of convergence of the sound speed using the sound ray signal (reception data) generated by the reception focus processing in the phasing addition unit 38, as in the determination unit 72b of the ultrasonic inspection apparatus 90b illustrated in FIG. 15. The determination unit 72b determines OK when the image quality index such as the brightness value or the sharpness is highest, and determines NG when the image quality index such as the brightness value or the sharpness does not reach the highest value.

When the determination unit 72b determines OK, the process proceeds to the detection processing unit 40 as in the ultrasonic inspection apparatus 90b illustrated in FIG. 15.

The detection processing unit 40 performs processing such as an envelope detection processing or the like on the sound ray signal generated by the phasing addition unit 38 to thereby generate B-mode image data that is tomographic image information regarding the tissue of the subject. Thereafter, the ultrasound image is created by the image creation unit 44 and displayed on the display unit 28.

On the other hand, when the determination unit 72*b* determines NG, the second time and subsequent processing is performed. The process proceeds to the element data processing unit 22. The delay time calculation unit 48 of the element data processing unit 22 calculates the delay time using the optimal sound speed set by the sound speed correction unit 76*c*. Thereafter, the superposition processing unit 50 performs the superposition processing on two or more pieces of unprocessed element data using the delay time calculated using the optimal sound speed to obtain processed element data.

After the processed element data is obtained in the element data processing unit 22 in this way, the process returns to the sound speed correction unit 76*c* and the optimal sound speed is newly set. The phasing addition unit 38 performs the reception focus processing on the processed element data obtained in the element data processing unit 22 based on the optimal sound speed newly set by the sound speed correction unit 76*c* to generate a sound ray signal (reception data), and the determination unit 72*b* performs the determination based on the image quality index such as the brightness value or the sharpness of the image or the degree of convergence of the sound speed using the sound ray signal generated by the phasing addition unit 38.

In the second time and subsequent processing, if the determination of the determination unit 72*b* is OK, the generation of the B-mode image data in the detection processing unit 40, the creation of the ultrasound image in the image creation unit 44, and the displaying of the ultrasound image on the display unit 28 are performed.

In contrast, if the determination of the determination unit 72*b* is NG, the calculation of the delay time in the delay time calculation unit 48 of the element data processing unit 22 using the new optimal sound speed set by the sound speed correction unit 76*c*, the generation of the processed element data in the superposition processing unit 50, the new setting of the optimal sound speed in the sound speed correction unit 76*c*, and the generation of the sound ray signal based on the optimal sound speed newly set by the sound speed correction unit 76*c* for the processed element data obtained by the element data processing unit 22 in the phasing addition unit 38 are repeated until the determination is OK, that is, until the optimal sound speed is set.

The present invention is not limited to the determination unit 72*a* or 72*b* being provided between the phasing addition unit 38 and the detection processing unit 40 in the ultrasonic inspection apparatuses 90*a* to 90*d*, and the determination unit 72*a* or 72*b* may be provided between the detection processing unit 40 and the image creation unit 44. Further, the present invention is not limited to the sound speed correction unit 76*c* being provided between the element data processing unit 22 or the element data storage unit 20 and the phasing addition unit 38, and the sound speed correction unit 76*c* may be provided between (an NG side of) the determination unit 72*a* or 72*b* and the element data processing unit 22.

Thus, in the ultrasonic inspection apparatuses 90*a* to 90*d* of Embodiment 5 of the present invention, since the delay time calculation unit of the element data processing unit 22 calculates the delay time using the optimized optimal sound speed, it is possible to create an ultrasound image using the processed element data in which the ghost signal is most appropriately attenuated and the true signal is most appropriately emphasized, and to obtain a sharp ultrasound image having a high SN ratio and an optimal spatial resolution with high resolution that does not depend on the width of the transmission beam, without using a dedicated ultrasound probe for generating a wide transmission ultrasonic beam and at a frame rate that is not different from the conventional frame rate.

The ultrasonic inspection apparatus of Embodiment 5 of the present invention is basically configured as described above.

Embodiment 6

Next, an ultrasonic inspection apparatus of Embodiment 6 of the present invention will be described based on FIG. 18.

Figure 18:
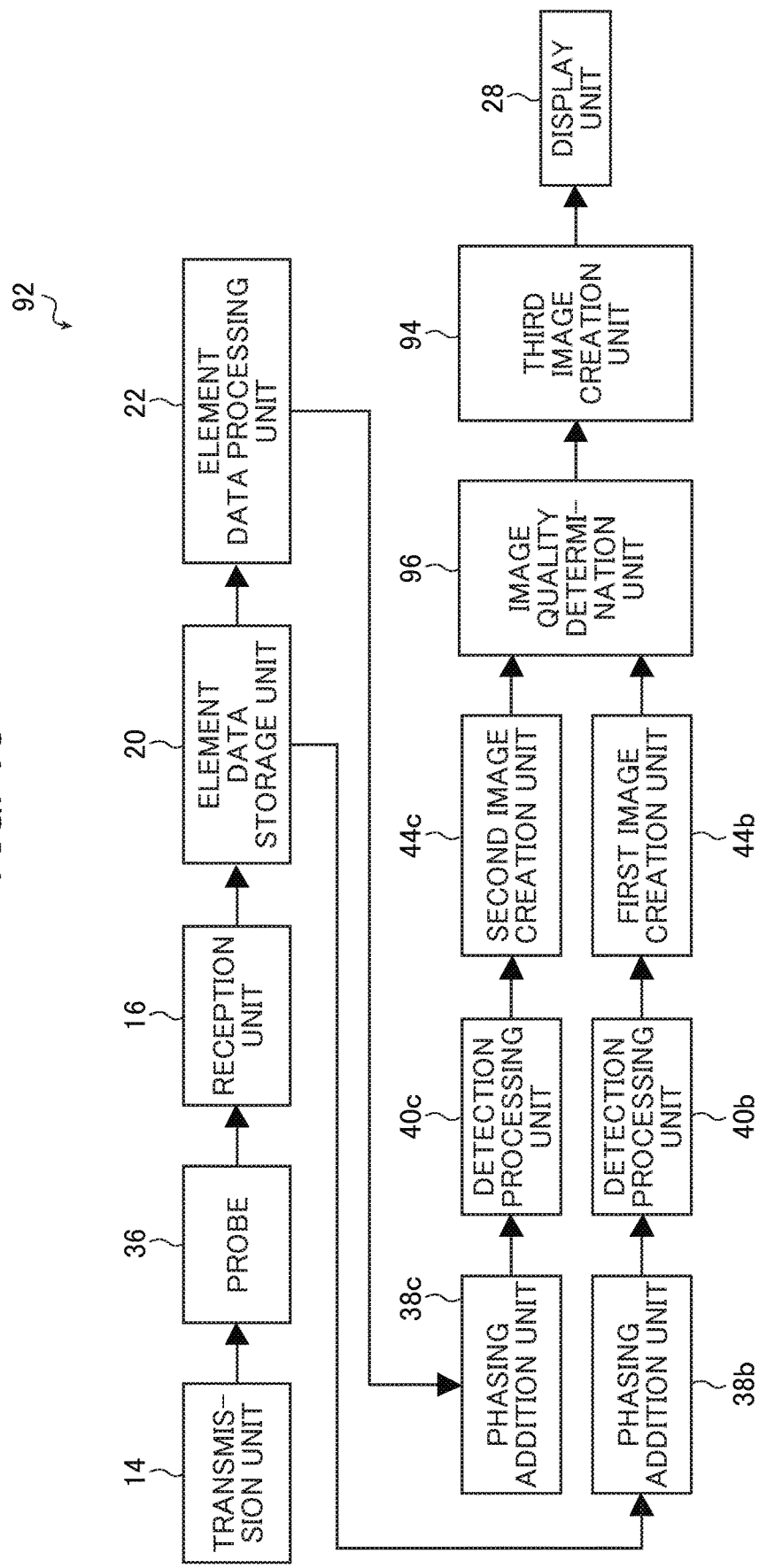
FIG. 18 is a block diagram conceptually illustrating, along a process flow, an example of primary units of an ultrasonic inspection apparatus of Embodiment 6 of the present invention.

FIG. 18 is a block diagram conceptually illustrating, along a process flow, an example of primary units of the ultrasonic inspection apparatus of Embodiment 6 of the present invention.

The ultrasonic inspection apparatus 92 illustrated in FIG. 18 has exactly the same configuration as the ultrasonic inspection apparatus 10 illustrated in FIG. 7 which includes the phasing addition unit 38, the detection processing unit 40, and the image creation unit 44, except that phasing addition units 38*b* and 38*c*, detection processing units 40*b* and 40*c*, first and second image creation units 44*b* and 44*c*, a third image creation unit 94, and an image quality determination unit 96. Accordingly, the same components are denoted with the same reference signs and detailed description thereof will be omitted.

The ultrasonic inspection apparatus 92 includes the transmission unit 14, the probe 36, the reception unit 16, the element data storage unit 20, the element data processing unit 22, the phasing addition units 38*b* and 38*c*, the detection processing units 40*b* and 40*c*, the first image creation unit 44*b*, the second image creation unit 44*c*, the third image creation unit 94, the image quality determination unit 96, and the display unit 28, as illustrated in FIG. 18.

Here, since the phasing addition unit 38*c*, the detection processing unit 40*c*, and the second image creation unit 44*c* respectively have exactly the same configuration as the phasing addition unit 38, the detection processing unit 40, and the image creation unit 44 illustrated in FIG. 7, detailed description thereof will be omitted.

In contrast, the phasing addition unit 38*b*, the detection processing unit 40*b* and the first image creation unit 44*b* are different from the phasing addition unit 38*c*, the detection processing unit 40*c* and the second image creation unit 44*c* in which the processed element data is a processing target in that their processing target is not the processed element data processed in the element data processing unit 22, but the unprocessed element data stored and held in the element data storage unit 20, and they perform the conventional processing thereon. However, they are exactly the same in processing function.

In such ultrasonic inspection apparatus 92, in the superposition processing in the element data processing unit 22, if the unprocessed element data is a right-left symmetric point-like reflection, the element data processing is performed to remove a ghost component, thereby generating processed element data. Then, through the processing in the phasing addition unit 38*c*, the detection processing unit 40*c* and the second image creation unit 44*c*, a sharp ultrasound image of the present invention having a high SN ratio and an optimal spatial resolution with high resolution that does not depend on the width of the transmission beam is generated using the processed element data in which the ghost signal is attenuated and the true signal is emphasized.

In contrast, in the superposition processing in the element data processing unit 22, if the unprocessed element data is right-left asymmetrical, the unprocessed element data is regarded as a speckle. In this case, if the element data processing of the element data processing unit 22 is not desired to be performed, a conventional ultrasound image is generated through the processing in the phasing addition unit 38b, the detection processing unit 40b and the first image creation unit 44b using the unprocessed element data stored and held in the element data storage unit 20, which has not been subjected to the element data processing.

Then, the image quality determination unit 96 compares image quality of a first ultrasound image created by the first image creation unit 44b that performs the conventional image processing on the unprocessed element data with image quality of a second ultrasound image created by the second image creation unit 44c from the processed element data obtained by the element data processing in the element data processing unit 22 of the present invention, based on the symmetry of the unprocessed element data, and performs a determination as to whether the first ultrasound image or the second ultrasound image is to be adopted based on a result of the comparison. Specifically, in the image quality comparison, the image quality determination unit 96 compares the image qualities using any one of a brightness value, contrast and graininess of the image or a combination of two or more of them. For example, when the brightness values are compared, it is determined that an image having a higher brightness is adopted.

Then, the third image creation unit 94 creates an ultrasound image for being displayed on the display unit 28 from the first ultrasound image and the second ultrasound image based on a result of the image quality determination performed by the image quality determination unit 96.

Specifically, the third image creation unit 94 selects any one of the first ultrasound image and the second ultrasound image as the ultrasound image to be displayed on the display unit 28, based on the image quality determination result of the image quality determination unit 96. For example, when the image quality determination unit 96 compares the brightness values of the first ultrasound image and the second ultrasound image, an image having a higher brightness value is adopted.

Alternatively, a region division unit that divides the first ultrasound image and the second ultrasound image into predetermined regions may be further provided, the image quality determination unit 96 may determine the image quality for each divided region at the time of the image quality comparison, and the third image creation unit 94 may select any one of the first ultrasound image and the second ultrasound image for each region based on the image quality determination result, and combine the images selected in the respective regions to generate an ultrasound image for being displayed on the display unit 28.

In the superposition processing in the element data processing unit 22, when an average value is used, a brightness value is likely to be lower in comparison with a case in which the element data processing is not performed. In this case, a high brightness image can be obtained by adopting the first ultrasound image generated in the conventional processing. Therefore, the third image creation unit 94 may compare the first ultrasound image created by the first image creation unit with the second ultrasound image created by the second image creation unit, and may adopt the first ultrasound image if the first ultrasound image created by the first image creation unit has a higher brightness in a distribution of high brightness reflection points. Alternatively, the third image creation unit 94, for example, may take an average value of the brightness values of the first ultrasound image and the second ultrasound image for each pixel for a region of which the image quality determination results are the same to generate the ultrasound image. Alternatively, a weighted average value may be taken depending on the image quality determination result.

It is needless to say that the ultrasonic inspection apparatuses of Embodiments 2 to 5 described above may be applied to this Embodiment 6.

Thus, in the ultrasonic inspection apparatus of Embodiment 6 of the present invention, it is possible to constantly generate an ultrasound image having high brightness.

In Embodiments 1 to 6 described above, the configuration in which the multiline processing is performed using first element data acquired through transmission and reception of ultrasonic waves to generate second element data, and an ultrasound image is generated using the second element data is adopted. However, the present invention is not limited thereto, and a configuration in which a first mode of generating an ultrasound image by use of the first element data and a second mode of generating an ultrasound image by use of the second element data are switchable may be adopted.

Embodiment 7

Next, an ultrasonic inspection apparatus of Embodiment 7 of the present invention will be described based on FIGS. 19 and 20.

Figure 19:
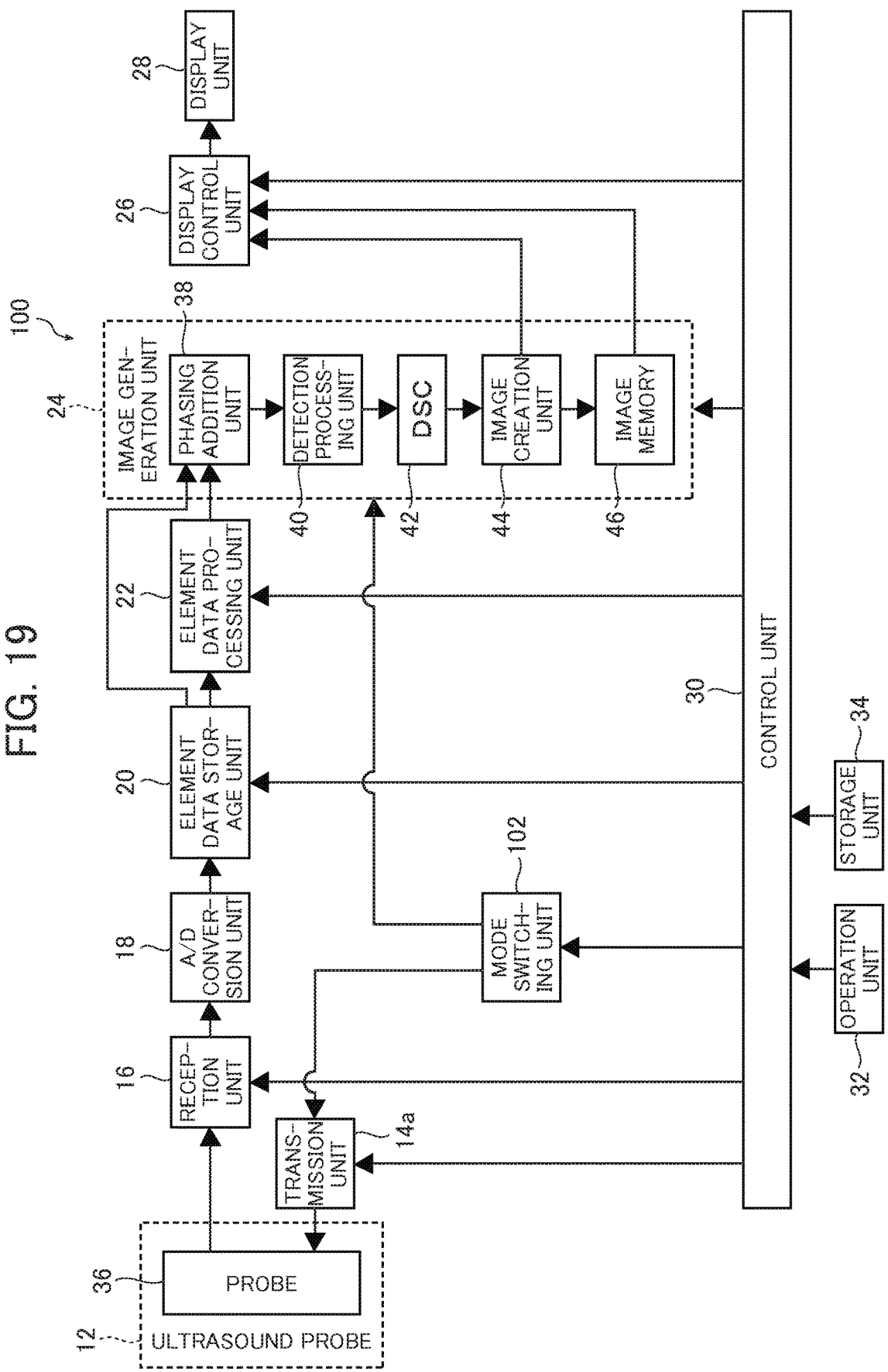
FIG. 19 is a block diagram conceptually illustrating an example of a configuration of an ultrasonic inspection apparatus of Embodiment 7 of the present invention.
Figure 20:
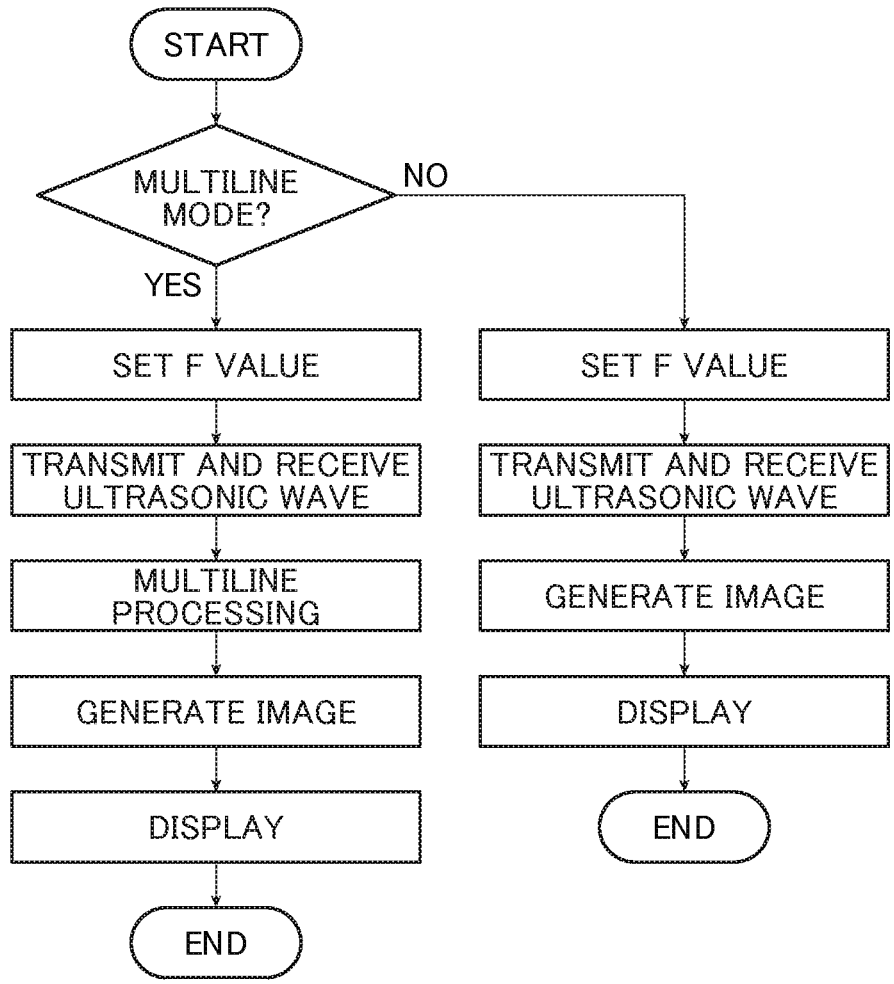
FIG. 20 is a flowchart illustrating an operation of the ultrasonic inspection apparatus illustrated in FIG. 19.

FIG. 19 is a block diagram conceptually illustrating an example of the configuration of the ultrasonic inspection apparatus of Embodiment 7 of the present invention, and FIG. 20 is a flowchart illustrating an operation of the ultrasonic inspection apparatus 100 illustrated in FIG. 19.

The ultrasonic inspection apparatus 100 illustrated in FIG. 19 has exactly the same configuration as the ultrasonic inspection apparatus 10 illustrated in FIG. 1 except that a transmission unit 14a is included instead of the transmission unit 14, and a mode switching unit 102 is included. Accordingly, the same components are denoted with the same reference signs and detailed description thereof will be omitted.

The ultrasonic inspection apparatus 100 illustrated in FIG. 19 has a configuration in which a first mode (normal mode) in which an ultrasound image is generated using first element data and a second mode (multiline processing mode) in which an ultrasound image is generated using second element data are switchable, and in the ultrasonic inspection apparatus 100, an F value when the ultrasonic beam is transmitted, that is, a ratio of depth of focus and numerical aperture is switched in response to switching of the mode.

The ultrasonic inspection apparatus 100 includes the ultrasound probe 12, the transmission unit 14, the reception unit 16, the A/D conversion unit 18, the element data storage unit 20, the element data processing unit 22, the image generation unit 24, the display control unit 26, the display unit 28, the control unit 30, the operation unit 32, the storage unit 34, and the mode switching unit 102, as illustrated in FIG. 19.

The mode switching unit 102 is a unit that switches the first mode (normal mode) in which the ultrasound image is generated in the image generation unit 24 using unprocessed element data (the first element data) that is not subjected to multiline processing and the second mode (multiline processing mode) in which the ultrasound image is generated using processed element data (the second element data) subjected to multiline processing by the element data processing unit 22, based on an instruction input from the operation unit 32 or an instruction from the control unit 30.

The mode switching unit 102 supplies mode information on the selected mode to the image generation unit 24 and the transmission unit 14a.

The transmission unit 14a has basically the same configuration as the transmission unit 14 of the ultrasonic inspection apparatus 10 of Embodiment 1 illustrated in FIG. 1 except that the F value of the ultrasonic beam to be transmitted is switched according to the selected mode based on the mode information supplied from the mode switching unit 102 and the ultrasonic beam is transmitted.

Specifically, when the multiline processing mode is selected, the transmission unit 14a causes the probe 36 to perform transmission of an ultrasonic beam of which the F value is smaller than the F value in the normal mode.

Figure 21A:
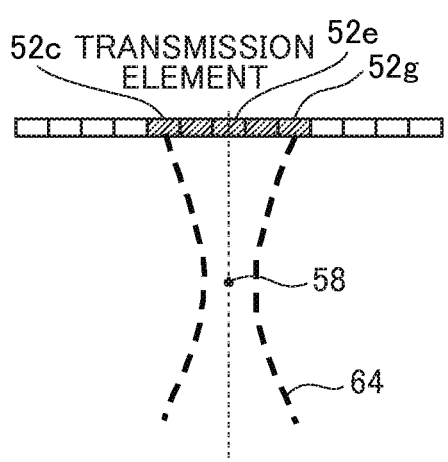
FIGS. 21A and 21B are schematic diagrams illustrating switching of an F value.
Figure 21B:
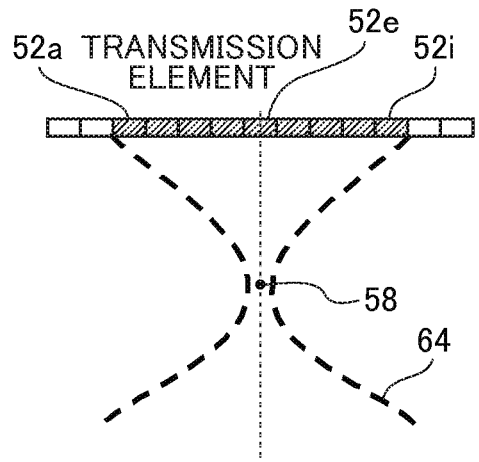

A schematic diagram illustrating an example of the F value in the normal mode is illustrated in FIG. 21A, and a schematic diagram illustrating an example of the F value in the multiline processing mode is illustrated in FIG. 21B.

In the normal mode, the transmission unit 14a transmits a transmission beam (ultrasonic beam) 56 that forms a predetermined focal point 58 using five elements 52c to 52g, including the element 52e that is a central element, as transmission elements, as illustrated in FIG. 21A.

On the other hand, in the multiline processing mode, the transmission unit 14a transmits the transmission beam 56 forming a predetermined focal point 58 using nine elements 52a to 52i, including the element 52e that is a central element, as transmission elements, as illustrated in FIG. 21B. In this case, the depth of the focal point 58 is set to the same depth as in the normal mode. Thus, in the multiline processing mode, the F value, that is, "depth of focus/numerical aperture" is smaller than the F value in the normal mode.

When the F value is great, the transmission beam 64 cannot be sufficiently narrowed down as illustrated in FIG. 21A, and thus, the waveform of the transmission beam 64 becomes similar to a plane wave. In contrast, when the F value is small, the transmission beam 64 can be narrowed down, as illustrated in FIG. 21B. When the transmission beam 64 is narrowed down, the focal point 58 approaches one point, and thus, a state similar to the geometrical model (see FIG. 5) for calculating the delay time in the delay time calculation unit 48 of the element data processing unit 22 can be formed.

That is, the geometrical model used when the delay time is calculated in the delay time calculation unit 48 regards the focal point as one virtual sound source. Therefore, by decreasing the F value and narrowing down the focal point, a state more similar to the model can be formed, and thus, precision of the superposition processing of the element data in the multiline processing can be improved and an image of higher quality can be obtained, compared with the case in which the F value is not switched.

As illustrated in the flow chart of FIG. 20, in the ultrasound diagnostic apparatus 100 of Embodiment 7, when the mode is switched to the multiline processing mode by the mode switching unit 102, the transmission unit 14a sets a small F value and performs transmission and reception of ultrasonic wave. The element data processing unit 22 performs the multiline processing using the first element data obtained through transmission and reception with the small F value to generate the second element data. The image generation unit 24 generates an ultrasound image using the second element data, and the display control unit 26 displays the ultrasound image on the display unit 28.

On the other hand, when the mode is switched to the normal mode by the mode switching unit 102, the transmission unit 14a sets a great F value, performs transmission and reception of ultrasonic wave, and acquires the first element data. The image generation unit 24 generates an ultrasound image using the first element data, and the display control unit 26 displays the ultrasound image on the display unit 28.

Figure 22A:
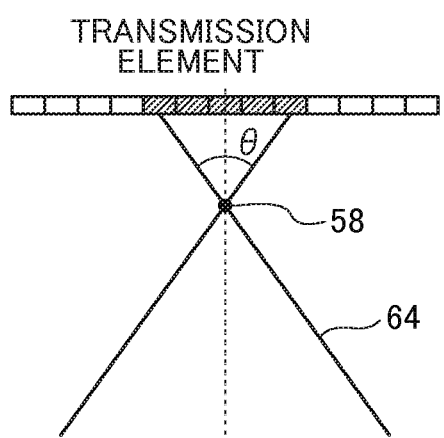
FIGS. 22A and 22B are schematic diagrams illustrating the position of a transmission focal point and a numerical aperture when the F value is constant.
Figure 22B:
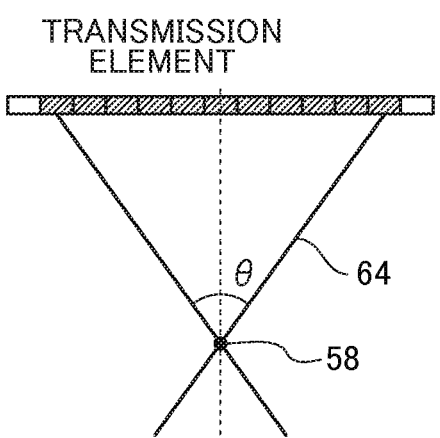

In each mode, it is preferable to set the position of the transmission focal point and the numerical aperture so that the F value is constant regardless of the depth of the focal point position of the ultrasonic beam. That is, it is preferable to set the focal point position and the numerical aperture so that a spread θ of the ultrasonic beam 64 is constant even when plural ultrasonic beams 64 forming different focal points 58 in a depth direction are transmitted, as illustrated in FIGS. 22A and 22B.

Needless to say, the ultrasonic inspection apparatuses of Embodiments 2 to 6 described above may be applied to this Embodiment 7.

While the configuration in which the multiline processing in the element data processing unit 22 is performed using the first element data is adopted in Embodiments 1 to 7 described above, the present invention is not limited thereto, and a configuration in which the multiline processing is performed using first reception data obtained by performing phasing addition on the first element data may be adopted.

Embodiment 8

Next, an ultrasonic inspection apparatus of Embodiment 8 of the present invention will be described based on FIG. 23.

Figure 23:
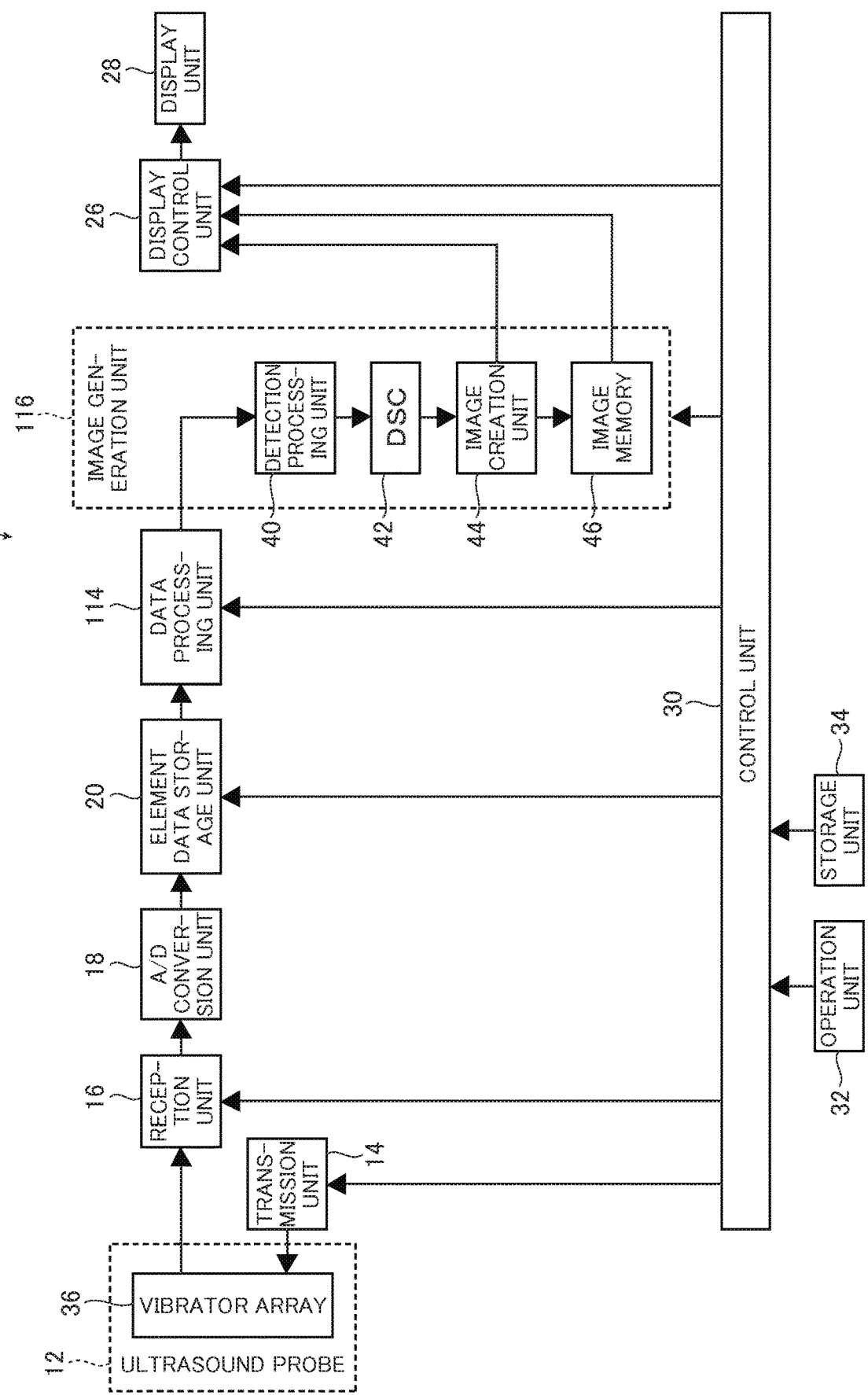
FIG. 23 is a block diagram conceptually illustrating an example of a configuration of an ultrasonic inspection apparatus of Embodiment 8 of the present invention.

FIG. 23 is a block diagram conceptually illustrating an example of the configuration of the ultrasonic inspection apparatus of Embodiment 8 of the present invention.

The ultrasonic inspection apparatus 110 illustrated in FIG. 23 has exactly the same configuration as the ultrasonic inspection apparatus 10 illustrated in FIG. 1 except that a data processing unit 114 is included instead of the element data processing unit 22, and an image generation unit 116 is included instead of the image generation unit 24. Accordingly, the same components are denoted with the same reference signs and detailed description thereof will be omitted.

The ultrasonic inspection apparatus 110 illustrated in FIG. 23 includes the ultrasound probe 12, the transmission unit 14 and the reception unit 16 that are connected to the ultrasound probe 12, the A/D conversion unit 18, the element data storage unit 20, the data processing unit 114, the image generation unit 116, the display control unit 26, the display unit 28, the control unit 30, the operation unit 32, and the storage unit 34.

Figure 24:
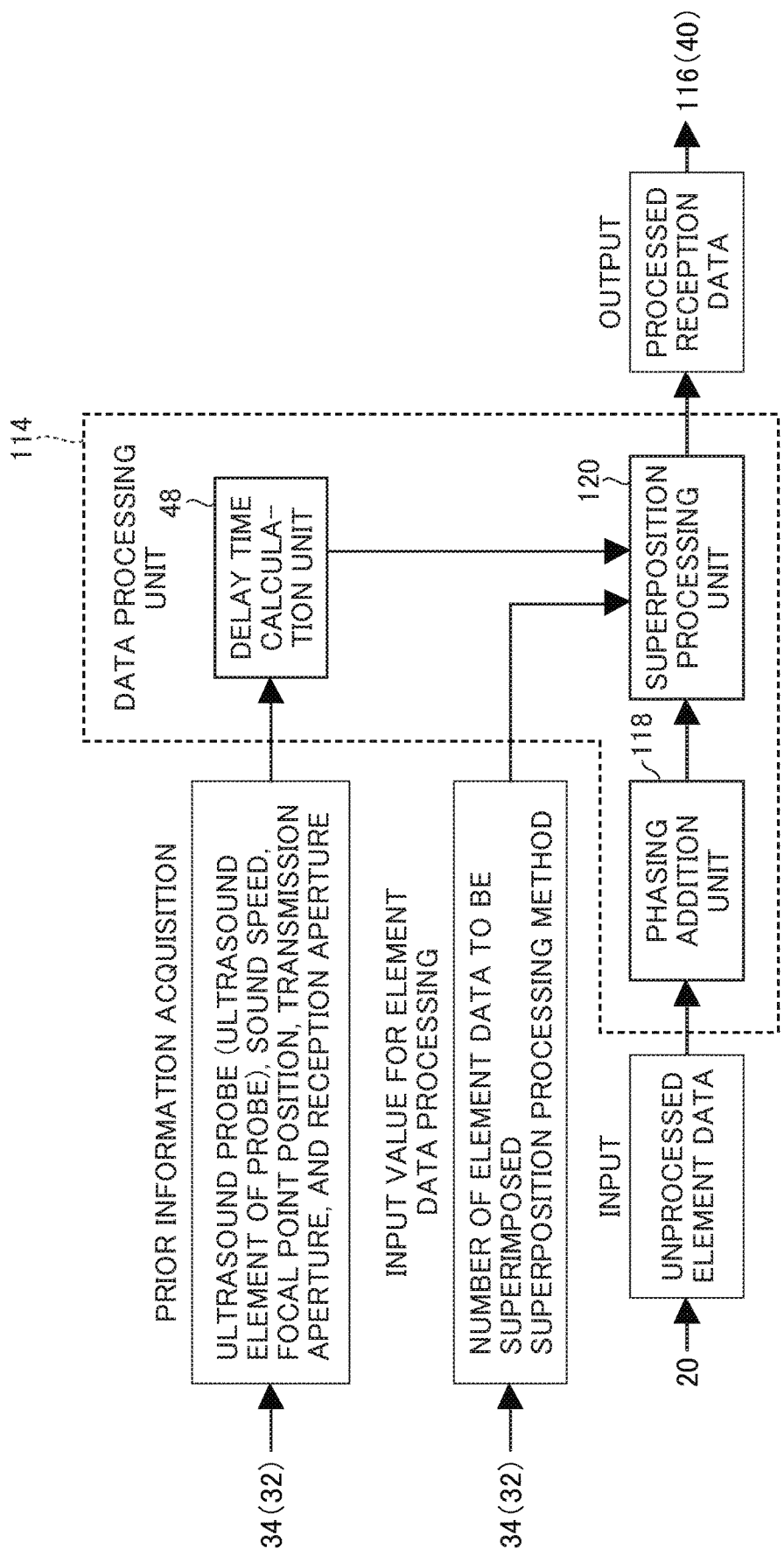
FIG. 24 is a block diagram conceptually illustrating an example of a configuration of a data processing unit of the ultrasonic inspection apparatus illustrated in FIG. 23.

FIG. 24 is a block diagram conceptually illustrating the configuration of the data processing unit 114.

The data processing unit 114 includes a phasing addition unit 118, a delay time calculation unit 48, and a superposition processing unit 120.

The phasing addition unit 118 performs phasing addition on the first element data read from the element data storage unit 20 to perform reception focus processing and generates first reception data.

Here, the phasing addition unit 118 respectively performs phasing addition on a plurality of pieces of element data to be superimposed in the superposition processing unit 120 to be described below, on the basis of the same element (line).

The superposition processing unit 120 causes the phasing addition unit 118 to read the element data from the element data storage unit 20 based on information on data processing such as a number of pieces of data to be superimposed and a superposition processing method, and acquires the first reception data generated by the phasing addition unit 118.

Further, the superposition processing unit 120 superimposes two or more pieces of first reception data while matching time on the reception time based on the delay time corresponding to each piece of reception data calculated by the delay time calculation unit 48 to generate processed (second) reception data.

The phasing addition unit 118 and the superposition processing unit 120 will be described in detail using FIGS. 25 and 26.

Figure 25:
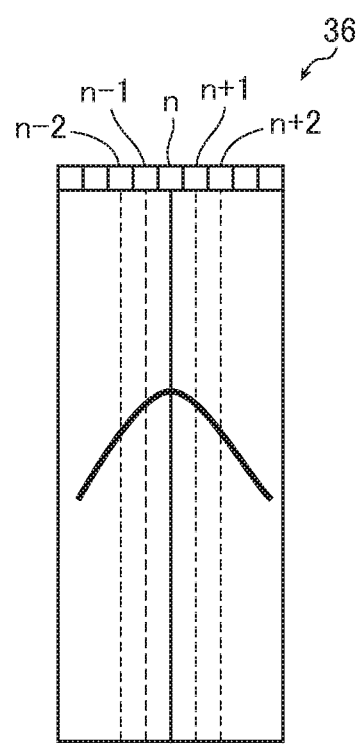
FIG. 25 is a diagram conceptually illustrating element data and an element.

FIG. 25 conceptually illustrates element data, and a vibrator array 36 in a position corresponding thereto.

The element data illustrated in FIG. 25 is (first) element data obtained by performing transmission and reception of ultrasonic wave using an n-th element as a central element. This element data is referred to n-th element data.

In the following description, for example, reception data generated by performing phasing addition on the n-th element data on the basis of an (n−2)-th line is referred to as the (n(n−2))-th reception data. That is, the reception data obtained by performing phasing addition on the n-th element data on the basis of an i-th line is referred to as n(i)-th reception data.

Figure 26C:
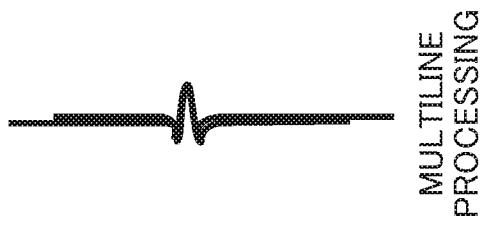
FIGS. 26A to 26C are diagrams illustrating phasing addition and superposition processing of the data processing unit illustrated in FIG. 24.
Figure 26B:
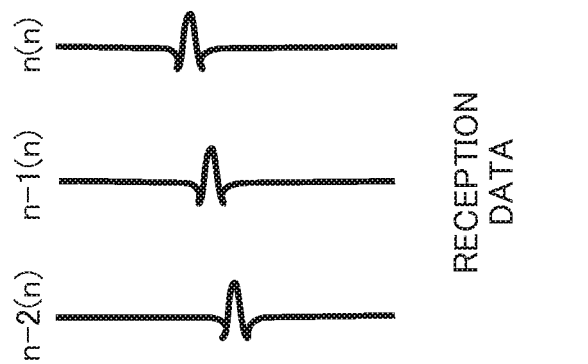
Figure 26A:
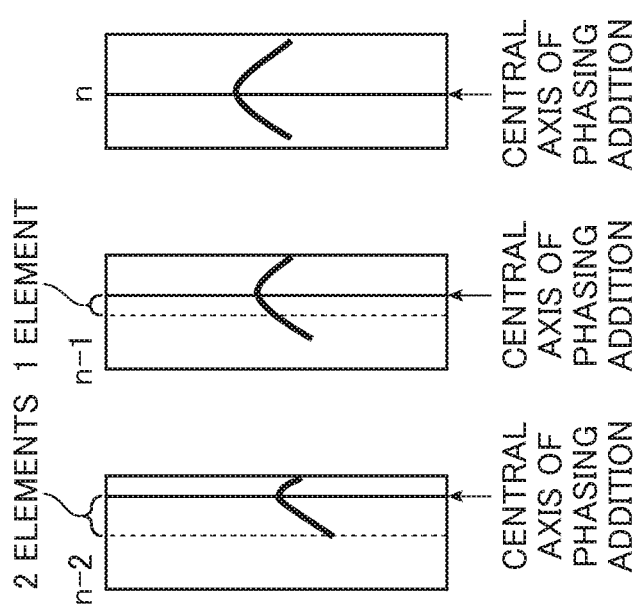

FIGS. 26A to 26C are diagrams illustrating the phasing addition in the phasing addition unit 118 and the superposition processing in the superposition processing unit 120.

FIG. 26A illustrates (n−2)-th element data, (n−1)-th element data, and n-th element data.

As an example, a case of generating the processed reception data corresponding to the n-th reception data using the (n−2)-th, (n−1)-th, and n-th reception data is considered.

When processed reception data corresponding to the n-th reception data is generated, the phasing addition unit 118 performs phasing addition of each piece of element data on the basis of the n-th element. That is, in FIG. 26A, the phasing addition of each piece of element data is performed on the basis of a line indicated by a solid line. The first reception data ((n−2(n))-th reception data, (n−1(n))-th reception data, and n(n)-th reception data) illustrated in FIG. 26B is generated through the phasing addition.

Then, the superposition processing unit 120 superimposes the pieces of first reception data generated by the phasing addition unit 118 while matching time based on the delay time corresponding to each piece of received data calculated by the delay time calculation unit 48 to generate processed received data corresponding to the n-th reception data as illustrated in FIG. 26C.

The data processing unit 114 supplies the processed reception data to the image generation unit 116.

The image generation unit 116 includes a detection processing unit 40, a DSC 42, an image creation unit 44, and an image memory 46.

In the image generation unit 116, the detection processing unit 40 generates B-mode image data by performing attenuation correction and envelope detection processing on the reception data. Further, the DSC 42 raster-converts the B-mode image data into image data corresponding to a scanning system of a normal television signal, and the image creation unit 44 performs a predetermined image processing such as gradation processing.

The image creation unit 44 stores the generated B-mode image data in the image memory 46 and/or sends the generated B-mode image data to the display control unit 26 to display the B-mode image of the subject on the display unit 28.

While the ultrasound diagnostic apparatus 110 illustrated in FIG. 23 has a configuration in which the phasing addition is performed on the first element data received while shifting the central axis to generate the first reception data, and then, the multiline processing is performed on the first reception data to generate the second reception data, the prevent invention is not limited thereto. A configuration in which after only horizontal shifting (see FIG. 6) is performed on each of the pieces of first element data directly before the second reception data is generated, phasing addition is performed to generate the first reception data, and multiline processing is performed on the first reception data to generate the second reception data may be adopted.

Needless to say, the ultrasonic inspection apparatus of Embodiments 2 to 7 described above may be applied to this Embodiment 8.

While the present invention has been described above in detail, naturally, the present invention is not limited to the above-described embodiments and may be improved or modified in various ways within the scope that does depart from the gist of the present invention.

For example, the respective components illustrated in FIGS. 1, 7, 8A, 8B, 9, 11 to 19, and 23 may be configured as hardware or may be configured as software executed by a computer or the like.

Further, the primary units of the ultrasonic inspection apparatus are shown as various processing blocks in the process flow in the embodiments illustrated in FIGS. 7, 8A, 8B, 9, and 12 to 18, and the optimal sound speed calculation unit of the sound speed correction unit of the ultrasonic inspection apparatus is shown as various processing blocks in the process flow in the example illustrated in FIG. 11. Accordingly, the phasing addition unit 38 is denoted with different reference signs 38, 38a, 38b, 38c, and 38d, the detection processing unit 40 is denoted with different reference signs 40, 40a, 40b, 40c, and 40d, and the image creation unit 44 is denoted with different reference signs 44, 44a, 44b, 44c, and 44d. However, the respective phasing addition units 38, 38a, 38b, 38c, and 38d, the respective detection processing units 40, 40a, 40b, 40c, and 40d, and the respective image creation units 44, 44a, 44b, 44c, and 44d may be different hardware or software, or may be the same hardware or software used in different sequences.

What is claimed is:

1. An ultrasonic inspection apparatus that inspects an inspection target using an ultrasonic beam, the ultrasonic inspection apparatus comprising:
   a probe comprising a plurality of elements being arranged in the probe, and uses the plurality of elements to transmit the ultrasonic beam, to receive an ultrasonic echo reflected by the inspection target, and to output an analog element signal according to the received ultrasonic echo; and
   processing circuitry, wherein the processing circuitry comprises:
   a transmission unit configured to cause the plurality of elements of the probe to transmit the ultrasonic beam a plurality of times so as to form a predetermined transmission focal point;

a reception unit configured to receive analog element signals output by the plurality of elements corresponding to the transmission of individual ultrasonic beams- and performs a predetermined processing on the analog element signals;

an analog-to-digital (A/D) conversion unit configured to perform A/D conversion on the analog element signals processed by the reception unit to obtain a plurality of pieces of first element data,
wherein the plurality of pieces of first element data are digital element signals, and the plurality of pieces of first element data indicate signal strength with respect to element position and time;

a data processing unit configured to select two or more pieces of first element data from the plurality of pieces of first element data and to use the two or more pieces of first element data to generate second element data,
wherein the second element data corresponds to any one of the two or more pieces of first element data, and the second element data indicates the signal strength with respect to element position and time, and an image generation unit configured to generate an ultrasound image based on the second element data,
wherein the data processing unit includes:
a delay time calculation unit configured to calculate a delay time of the two or more pieces of the first element data, and
a superposition processing unit configured to perform delay time correction on the two or more pieces of first element data by using the calculated delay time, to shift the two or more pieces of first element data so as to align the two or more pieces of first element data to a reception position of a central element of the probe, and to superimpose the delayed and shifted two or more pieces of first element data to generate the second element data,
wherein the data processing unit is further configured to change conditions of acquisition of the two or more pieces of first element data to be selected from the plurality of pieces of first element data depending on a depth of a position in which the second element data is obtained.

2. The ultrasonic inspection apparatus according to claim 1, wherein the transmission unit performs at least one of changing of a central element and changing of a transmission direction of at least one of the individual ultrasonic beams.

3. The ultrasonic inspection apparatus according to claim 2, wherein the data processing unit generates the second element data using at least one of the plurality of pieces of first element data obtained through the plurality of transmissions of the ultrasonic beam in which their corresponding central elements are different from each other and at least one of the plurality of pieces of first element data obtained through the plurality of transmissions of the ultrasonic beam in which their corresponding transmission directions differ from each other.

4. The ultrasonic inspection apparatus according to claim 1, wherein the data processing unit generates the second element data from the plurality of pieces of first element data obtained through transmissions of the ultrasonic beam in which transmission areas overlap.

5. The ultrasonic inspection apparatus according to claim 1, wherein the superposition processing unit superimposes the delayed and shifted two or more pieces of first element data to generate the second element data based on a position of the plurality of elements and a reception time at which the plurality of elements receive the ultrasonic echo.

6. The ultrasonic inspection apparatus according to claim 1, wherein
the delay time calculation unit calculates the delay time of the two or more pieces of first element data based on at least one of a piece of information acquired in advance regarding the probe, a sound speed of the inspection target, a focal point position of the ultrasonic beam, a transmission aperture of the probe set by the transmission unit, and a reception aperture of the probe set by the reception unit, and
the superposition processing unit superimposes the delayed and shifted two or more pieces of first element data to generate the second element data based on the number of pieces of first element data to be superimposed among the delayed and shifted two or more pieces of first element data and a superposition processing method that are set in advance.

7. The ultrasonic inspection apparatus according to claim 1, wherein the data processing unit generates the second element data from element data of only a superimposed portion when the two or more pieces of first element data are superimposed by the superposition processing unit.

8. The ultrasonic inspection apparatus according to claim 1, wherein the superposition processing unit superimposes the delayed and shifted two or more pieces of first element data after multiplying each of the delayed and shifted pieces of first element data by a weighting coefficient.

9. The ultrasonic inspection apparatus according to claim 1, wherein the superposition processing unit superimposes the delayed and shifted two or more pieces of first element data based on at least two or more different points on a time axis on a reception time of each piece of the delayed and shifted two or more pieces of first element data.

10. The ultrasonic inspection apparatus according to claim 9, wherein the at least two or more different points on the time axis is based on each transmission aperture of the probe set by the transmission unit.

11. The ultrasonic inspection apparatus according to claim 9, wherein the at least two or more different points on the time axis is based on each transmission aperture when the transmission of one of the individual ultrasonic beams is performed in at least two or more transmission apertures for each of the two or more pieces of first element data.

12. The ultrasonic inspection apparatus according to claim 9, wherein the at least two or more different points on the time axis is based on a sound speed of the inspection target.

13. The ultrasonic inspection apparatus according to claim 9, wherein when
the transmission unit transmits the ultrasonic beam for each transmission line to form a transmission focal point of a different depth on the same transmission line, the reception unit acquires the analog element signals corresponding to the same transmission line, and
the data processing unit generates the second element data from the two or more pieces of first element data obtained through transmission and reception of the ultrasonic beam for each depth of the transmission focal point.

14. The ultrasonic inspection apparatus according to claim 1, wherein
the transmission unit determines a transmission focal point depth depending on the depth of the position in which the second element data is obtained, and causes the probe to perform transmission of the ultrasonic beam a plurality of times at the determined transmission focal point depth to acquire the plurality of pieces of first element data, and the data processing unit selects the two or more pieces of the first element data for generating the second element data from among the plurality of pieces of first element data obtained through the transmission of the ultrasonic beam of the determined transmission focal point depth.

15. The ultrasonic inspection apparatus according to claim 1, wherein the transmission unit determines a transmission numerical aperture depending on the depth of the position in which the second element data is obtained, and causes the probe to perform the transmission of the ultrasonic beam using the determined transmission numerical aperture a plurality of times to acquire the plurality of pieces of first element data, and the data processing unit selects the two or more pieces of the first element data for generating the second element data from among the plurality of pieces of first element data obtained through the transmission of the ultrasonic beam using the determined transmission numerical aperture.

16. The ultrasonic inspection apparatus according to claim 1, wherein the transmission unit causes the probe to perform steering transmission.

17. The ultrasonic inspection apparatus according to claim 1, wherein the element data include phase information and amplitude information.

18. The ultrasonic inspection apparatus according to claim 1, further comprising:

an element data storage that stores at least one of the first element data and the second element data.

19. The ultrasonic inspection apparatus according to claim 1, wherein the data processing unit performs phasing addition of each of the plurality of pieces of first element data to generate a plurality of pieces of first reception data directly before generating the second element data from the plurality of pieces of first element data, and generates second reception data corresponding to any one of the pieces of first reception data from the plurality of pieces of first reception data.

20. The ultrasonic inspection apparatus according to claim 1, wherein the data processing unit changes the number of pieces of the first element data to be selected depending on the depth of the position in which the second element data is obtained.

21. The ultrasonic inspection apparatus according to claim 20, wherein the data processing unit changes the number of pieces of the first element data to be selected depending on the depth of the position in which the corresponding second element data is obtained based on a spatial spread of the ultrasonic beam within the inspection target.

22. The ultrasonic inspection apparatus according to claim 20, wherein the data processing unit changes the number of pieces of the first element data to be selected depending on the depth of the position in which the corresponding second element data is obtained based on a signal in a spatial position within the inspection target.

23. The ultrasonic inspection apparatus according to claim 20, wherein the data processing unit obtains an optimal number of pieces of element data based on a signal in the plurality of pieces of second element data created by changing the number of pieces of the first element data to be selected.

24. The ultrasonic inspection apparatus according to claim 1, wherein the data processing unit changes the number of pieces of the first element data to be selected depending on the depth of the position in which the second element data corresponding to the first element data to be selected is obtained based on a result of waveform analysis of the first element data.

25. The ultrasonic inspection apparatus according to claim 24, wherein the waveform analysis includes analyzing relevance or a coherence characteristic of a waveform regarding a candidate of the first element data to be selected.

26. An ultrasonic inspection apparatus that inspects an inspection target using an ultrasonic beam, the ultrasonic inspection apparatus comprising:

a probe comprising a plurality of elements being arranged in the probe, and uses the plurality of elements to transmit the ultrasonic beam, to receive an ultrasonic echo reflected by the inspection target, and to output an analog element signal according to the received ultrasonic echo; and processing circuitry, wherein the processing circuitry comprises:

a transmission unit configured to cause the plurality of elements of the probe to transmit the ultrasonic beam a plurality of times so as to form a predetermined transmission focal point;

a reception unit configured to receive analog element signals output by the plurality of elements corresponding to the transmission of individual ultrasonic beams and performs a predetermined processing on the analog element signals;

an analog-to-digital (A/D) conversion unit configured to perform A/D conversion on the analog element signals processed by the reception unit to obtain a plurality of pieces of first element data, wherein the plurality of pieces of first element data are digital element signals, and the plurality of pieces of first element data indicate signal strength with respect to element position and time;

a phasing addition unit configured to perform phasing addition on the plurality of pieces of first element data around a line corresponding to the same element to generate a plurality of pieces of first reception data indicating signal strength with respect to time;

a data processing unit configured to select two or more pieces of first reception data from the plurality of pieces of first reception data and to use the two or more pieces of first reception data to generate second reception data corresponding to any one of the plurality of pieces of first reception data from the plurality of the pieces of first element data on which phasing addition is performed around the line corresponding to the same element, and an image generation unit configured to generate an ultrasound image based on the second reception data, wherein the data processing unit includes:

a delay time calculation unit configured to calculate a delay time of the two or more pieces of first reception data, and a superposition processing unit configured to perform delay time correction on the two or more pieces of first reception data using the calculated delay time, to shift the two or more pieces of first reception data so as to align the two or more pieces of first reception data to a reception position of a central element of the probe, and to superimpose the delayed and shifted two or more pieces of first reception data to generate the second reception data, wherein the data processing unit is further configured to change conditions of acquisition of the two or more pieces of first reception data to be selected from the plurality of pieces of first reception data depending on a depth of a position in which the second reception data is obtained.

* * * * *